(12) United States Patent
Barlaam et al.

(10) Patent No.: US 7,838,530 B2
(45) Date of Patent: Nov. 23, 2010

(54) QUINAZOLINE DERIVATIVES AS ANTIPROLIFERATIVE AGENTS

(75) Inventors: Bernard Christophe Barlaam, Reims (FR); Laurent Francois Andre Hennequin, Reims (FR); Christopher Thomas Halsall, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 1247 days.

(21) Appl. No.: 10/572,794

(22) PCT Filed: Sep. 22, 2004

(86) PCT No.: PCT/GB2004/004137

§ 371 (c)(1),
(2), (4) Date: Mar. 21, 2006

(87) PCT Pub. No.: WO2005/030765

PCT Pub. Date: Apr. 7, 2005

(65) Prior Publication Data

US 2006/0287295 A1   Dec. 21, 2006

(30) Foreign Application Priority Data

Sep. 25, 2003   (GB) ................. 0322409.4

(51) Int. Cl.
*A61K 31/517* (2006.01)
*C07D 239/72* (2006.01)
(52) U.S. Cl. .................. 514/266.22; 544/293
(58) Field of Classification Search ............ 514/266.22; 544/293
See application file for complete search history.

(56) References Cited

U.S. PATENT DOCUMENTS

| | | | |
|---|---|---|---|
| 4,335,127 A | 6/1982 | Vandenberk et al. ... | 514/266.22 |
| 4,921,863 A | 5/1990 | Sugimoto et al. ........... | 514/319 |
| 5,457,105 A | 10/1995 | Barker ..................... | 514/234.5 |
| 5,616,582 A | 4/1997 | Barker ..................... | 514/234.5 |
| 5,747,498 A | 5/1998 | Schnur et al. ........... | 514/266.4 |
| 5,770,599 A | 6/1998 | Gibson .................... | 514/228.2 |
| 6,297,258 B1 | 10/2001 | Wissner et al. ............ | 514/313 |
| 6,562,319 B2 | 5/2003 | Mishani et al. ........... | 424/1.81 |
| 6,972,288 B1 | 12/2005 | Himmelsbach et al. .. | 514/234.8 |
| 7,049,438 B2 | 5/2006 | Hennequin et al. | |
| 7,148,230 B2 | 12/2006 | Bradbury et al. | |
| 7,569,577 B2 | 8/2009 | Hennequin et al. | |
| 7,625,908 B2 | 12/2009 | Bradbury et al. | |
| 7,632,840 B2 | 12/2009 | Delouvrie et al. | |
| 7,659,279 B2 | 2/2010 | Hennequin et al. | |
| 7,696,214 B2 | 4/2010 | Hennequin et al. | |
| 2002/0082270 A1 | 6/2002 | Himmelsbach et al. .. | 514/266.2 |
| 2002/0128553 A1 | 9/2002 | Mishani et al. ............ | 600/431 |
| 2004/0048880 A1 | 3/2004 | Himmelsbach et al. .. | 514/266.2 |
| 2004/0176361 A1 | 9/2004 | Fujio et al. ............... | 514/224.2 |
| 2005/0043336 A1 | 2/2005 | Hennequin et al. | |
| 2005/0054662 A1 | 3/2005 | Hennequin et al. | |
| 2005/0165035 A1 | 7/2005 | Bradbury et al. ........ | 514/266.22 |
| 2005/0215574 A1 | 9/2005 | Bradbury et al. | |
| 2006/0211714 A1 | 9/2006 | Hennequin et al. | |
| 2006/0258642 A1 | 11/2006 | Hennequin et al. | |
| 2007/0015743 A1 | 1/2007 | Bradbury et al. | |
| 2007/0032508 A1 | 2/2007 | Bradbury et al. | |
| 2007/0032513 A1 | 2/2007 | Hennequin et al. | |
| 2007/0037837 A1 | 2/2007 | Hennequin et al. | |
| 2007/0043009 A1 | 2/2007 | Hennequin et al. | |
| 2007/0043010 A1 | 2/2007 | Bradbury et al. | |
| 2007/0082921 A1 | 4/2007 | Hennequin et al. | |
| 2007/0088044 A1 | 4/2007 | Hennequin et al. | |
| 2007/0099943 A1 | 5/2007 | Bradbury et al. | |
| 2007/0149546 A1 | 6/2007 | Bradbury et al. | |
| 2007/0232607 A1 | 10/2007 | Bradbury et al. | |
| 2007/0244136 A1 | 10/2007 | Hennequin et al. | |
| 2007/0293490 A1 | 12/2007 | Delouvrie et al. | |
| 2008/0096881 A1 | 4/2008 | Bradbury et al. | |
| 2008/0108613 A1 | 5/2008 | Barlaam et al. | |
| 2008/0234263 A1 | 9/2008 | Hennequin et al. | |
| 2008/0269487 A1 | 10/2008 | Bradbury et al. | |
| 2009/0023759 A1 | 1/2009 | Bradbury | |
| 2009/0029968 A1 | 1/2009 | Bradbury et al. | |

(Continued)

FOREIGN PATENT DOCUMENTS

DE   10040527   2/2002

(Continued)

OTHER PUBLICATIONS

Grünwald V. et. al., Review, J. Nat. Can. Inst., vol. 95, No. 12, Jun. 18, 2003, pp. 851-867.*

(Continued)

*Primary Examiner*—James O Wilson
*Assistant Examiner*—Tamthom N Truong
(74) *Attorney, Agent, or Firm*—Morgan, Lewis & Bockius LLP

(57) ABSTRACT

The invention concerns quinazoline derivatives of Formula (I), wherein each of $R^{1a}$, $R^{1b}$, $R^2$, $R^3$ and a have any of the meanings defined in the description; processes for their preparation, pharmaceutical compositions containing them and their use in the manufacture of a medicament for use as an antiproliferative agent in the prevention or treatment of tumours which are sensitive to inhibition of erbB receptor tyrosine kinases.

(I)

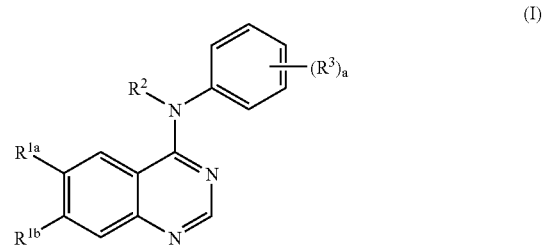

17 Claims, No Drawings

U.S. PATENT DOCUMENTS

| | | |
|---|---|---|
| 2009/0048251 A1 | 2/2009 | Bradbury et al. |
| 2009/0137615 A1 | 5/2009 | Bradbury |
| 2009/0221616 A1 | 9/2009 | Bradbury |
| 2009/0239861 A1 | 9/2009 | Bradbury |
| 2009/0312343 A1 | 12/2009 | Hennequin et al. |
| 2010/0029696 A1 | 2/2010 | Bradbury |

FOREIGN PATENT DOCUMENTS

| | | |
|---|---|---|
| EP | 0 288 563 | 5/1994 |
| EP | 0 566 226 | 11/1995 |
| EP | 0 837 063 | 4/1998 |
| EP | 1 230 919 | 8/2002 |
| EP | 1 369 418 | 12/2003 |
| WO | WO 88/02365 | 4/1988 |
| WO | WO 96/09294 | 3/1996 |
| WO | WO 96/30347 | 10/1996 |
| WO | WO 96/33977 | 10/1996 |
| WO | WO 96/33978 | 10/1996 |
| WO | WO 96/33979 | 10/1996 |
| WO | WO 96/33980 | 10/1996 |
| WO | WO 96/33981 | 10/1996 |
| WO | WO 96/39145 | 12/1996 |
| WO | WO 97/03069 | 1/1997 |
| WO | WO 97/30034 | 8/1997 |
| WO | WO 97/30035 | 8/1997 |
| WO | WO 97/30044 | 8/1997 |
| WO | WO 97/38983 | 10/1997 |
| WO | WO 97/38994 | 10/1997 |
| WO | WO 98/02434 | 1/1998 |
| WO | WO 98/13354 | 4/1998 |
| WO | WO 99/06378 | 2/1999 |
| WO | WO 99/35132 | 7/1999 |
| WO | WO 00/09481 | 2/2000 |
| WO | WO 00/18740 | 4/2000 |
| WO | WO 00/24718 | 5/2000 |
| WO | WO 00/44728 | 8/2000 |
| WO | WO 00/55141 | 9/2000 |
| WO | WO 00/55141 A | 9/2000 |
| WO | WO 00/56720 | 9/2000 |
| WO | WO 01/07432 | 2/2001 |
| WO | WO 01/21596 | 3/2001 |
| WO | WO 01/21597 | 3/2001 |
| WO | WO 01/77085 | 10/2001 |
| WO | WO 01/77085 A | 10/2001 |
| WO | WO 01/94341 | 12/2001 |
| WO | WO 01/98277 | 12/2001 |
| WO | WO 02/24684 | 3/2002 |
| WO | WO 02/30924 | 4/2002 |
| WO | WO 02/34744 | 5/2002 |
| WO | WO 02/41882 | 5/2002 |
| WO | WO 02/44166 | 6/2002 |
| WO | WO 02/48117 | 6/2002 |
| WO | WO 02/056882 | 7/2002 |
| WO | WO 02/062767 | 8/2002 |
| WO | WO 02/066445 | 8/2002 |
| WO | WO 02/068409 | 9/2002 |
| WO | WO 02/073235 | 9/2002 |
| WO | WO 02/076976 | 10/2002 |
| WO | WO 02/092577 | 11/2002 |
| WO | WO 02/092578 | 11/2002 |
| WO | WO 02/097490 | 12/2002 |
| WO | WO 03/002448 A | 3/2003 |
| WO | WO 03/024448 | 3/2003 |
| WO | WO 03/040108 | 5/2003 |
| WO | WO 03/040109 | 5/2003 |
| WO | WO 03/049740 | 6/2003 |
| WO | WO 03/082290 | 10/2003 |
| WO | WO 03/082290 A | 10/2003 |
| WO | WO 03/082831 | 10/2003 |
| WO | WO 2004/006846 | 1/2004 |
| WO | WO 2004/006846 A | 1/2004 |
| WO | WO 2004/064718 | 8/2004 |
| WO | WO 2004/093880 | 11/2004 |
| WO | WO 2004/096226 | 11/2004 |
| WO | WO 2005/012290 | 2/2005 |
| WO | WO 2005/013998 | 2/2005 |
| WO | WO 2005/026150 | 3/2005 |
| WO | WO 2005/026151 | 3/2005 |
| WO | WO 2005/026152 | 3/2005 |
| WO | WO 2005/026156 | 3/2005 |
| WO | WO 2005/026157 | 3/2005 |
| WO | WO 2005/028469 | 3/2005 |
| WO | WO 2005/028470 | 3/2005 |
| WO | WO 2005/030757 | 4/2005 |
| WO | WO 2005/051923 | 6/2005 |
| WO | WO 2005/075439 | 8/2005 |
| WO | WO 2005/118572 | 12/2005 |
| WO | WO 2006/064196 | 6/2006 |
| WO | WO 2006/090163 | 8/2006 |
| WO | WO 2006/092573 | 9/2006 |
| WO | WO 2006/092574 | 9/2006 |
| WO | WO 2006/117521 | 11/2006 |
| WO | WO 2006/117523 | 11/2006 |
| WO | WO 2007/034143 | 3/2007 |
| WO | WO 2007/034144 | 3/2007 |
| WO | WO 2007/063291 | 6/2007 |
| WO | WO 2007/063293 | 6/2007 |

OTHER PUBLICATIONS

Ballard et al. "Inhibitors of epidermal growth factor receptor tyrosine kinase: Novel C-5 substituted anilinoquinazolines designed to target the ribose pocket" Bioorg Med Chem Lett. 16(6):1633-1637 (2006).

Ballard et al. "5-Substituted 4-anilinoquinazolines as potent, selective and orally active inhibitors of erbB2 receptor tyrosine kinase" Bioorg Med Chem Lett. 15(19):4226-4229 (2005).

Ballard et al. "Inhibitors of epidermal growth factor receptor tyrosine kinase: optimisation of potency and in vivo pharmacokinetics" Bioorg Med Chem Lett. 16(18):4908-4912 (2006).

Harris et al. "Facile synthesis of 7-amino anilinoquinazolines via direct amination of the quinazoline core" Tetrahedron letters 46(43): 7381-7384 (2005).

Harris et al. "Selective alkylation of a 6,7-dihydroxyquinazoline" Tetrahedron letters 46(45):7715-7719 (2005).

Hennequin et al. "Novel 4-anilinoquinazolines with C-6 carbon-linked side chains: synthesis and structure-activity relationship of a series of potent, orally active, EGF receptor tyrosine kinase inhibitors" Bioorg Med Chem Lett. 16(10):2672-2676 (2006).

Stamos et al. "Structure of the Epidermal Growth Factor Receptor Kinase Domain Alone and in Complex with a 4-Anilinoquinazoline Inhibitor" J. Biol. Chem. 277(48):46265-46272 (2002).

Traxler et al. "Protein tyrosine kinase inhibitors in cancer treatment" Exp. Opin. Ther. Patents 7(6):571-588 (1997).

Traxler et al. "Tyrosine kinase inhibitors in cancer treatment (Part II)" Exp. Opin. Ther. Patents 8(12):1599-1625 (1998).

Tsou et al. "6-Substituted-4-(3-bromophenylamino)quinazolines as Putative Irreversible Inhibitors of the Epidermal Growth Factor Receptor (EGFR) and Human Epidermal Growth Factor Receptor (HER-2) Tyrosine Kinases with Enhanced Antitumor Activity" J. Med. Chem. 44:2719-2734 (2001).

Vema et al. "Design of EGFR kinase inhibitors: a ligand-based approach and its confirmation with structure-based studies" Bioorg Med Chem. 11(21):4643-4653 (2003).

* cited by examiner

QUINAZOLINE DERIVATIVES AS ANTIPROLIFERATIVE AGENTS

The invention concerns certain novel quinazoline derivatives, or pharmaceutically-acceptable salts thereof, which possess anti-tumour activity and are accordingly useful in methods of treatment of the human or animal body. The invention also concerns processes for the manufacture of said quinazoline derivatives, to pharmaceutical compositions containing them and to their use in therapeutic methods, for example in the manufacture of medicaments for use in the prevention or treatment of solid tumour disease in a warm-blooded animal such as man.

Many of the current treatment regimes for diseases resulting from the abnormal regulation of cellular proliferation such as psoriasis and cancer, utilise compounds that inhibit DNA synthesis and cellular proliferation. To date, compounds used in such treatments are generally toxic to cells however their enhanced effects on rapidly dividing cells such as tumour cells can be beneficial. Alternative approaches to these cytotoxic anti-tumour agents are currently being developed, for example selective inhibitors of cell signalling pathways. These types of inhibitors are likely to have the potential to display an enhanced selectivity of action against tumour cells and so are likely to reduce the probability of the therapy possessing unwanted side effects.

Eukaryotic cells are continually responding to many diverse extracellular signals that enable communication between cells within an organism. These signals regulate a wide variety of physical responses in the cell including proliferation, differentiation, apoptosis and motility. The extracellular signals take the form of a diverse variety of soluble factors including growth factors as well as paracrine and endocrine factors. By binding to specific transmembrane receptors, these ligands integrate the extracellular signal to the intracellular signalling pathways, therefore transducing the signal across the plasma membrane and allowing the individual cell to respond to its extracellular signals. Many of these signal transduction processes utilise the reversible process of the phosphorylation of proteins that are involved in the promotion of these diverse cellular responses. The phosphorylation status of target proteins is regulated by specific kinases and phosphatases that are responsible for the regulation of about one third of all proteins encoded by the mammalian genome. As phosphorylation is such an important regulatory mechanism in the signal transduction process, it is therefore not surprising that aberrations in these intracellular pathways result in abnormal cell growth and differentiation and so promote cellular transformation (reviewed in Cohen et al, *Curr Opin Chem Biol*, 1999, 3, 459-465).

It has been widely shown that a number of these tyrosine kinases are mutated to constitutively active forms and/or when over-expressed result in the transformation of a variety of human cells. These mutated and over-expressed forms of the kinase are present in a large proportion of human tumours (reviewed in Kolibaba et al, Biochimica et Biophysica Acta, 1997, 133, F217-F248). As tyrosine kinases play fundamental roles in the proliferation and differentiation of a variety of tissues, much focus has centred on these enzymes in the development of novel anti-cancer therapies. This family of enzymes is divided into two groups—receptor and non-receptor tyrosine kinases e.g. EGF Receptors and the SRC family respectively. From the results of a large number of studies including the Human Genome Project, about 90 tyrosine kinase have been identified in the human genome, of this 58 are of the receptor type and 32 are of the non-receptor type. These can be compartmentalised in to 20 receptor tyrosine kinase and 10 non-receptor tyrosine kinase subfamilies (Robinson et al, *Oncogene,* 2000, 19, 5548-5557).

The receptor tyrosine kinases are of particular importance in the transmission of mitogenic signals that initiate cellular replication. These large glycoproteins, which span the plasma membrane of the cell, possess an extracellular binding domain for their specific ligands (such as Epidermal Growth Factor (EGF) for the EGF Receptor). Binding of a ligand results in the activation of the receptor's kinase enzymatic activity that is encoded by the intracellular portion of the receptor. This activity phosphorylates key tyrosine amino acids in target proteins, resulting in the transduction of proliferative signals across the plasma membrane of the cell.

It is known that the erbB family of receptor tyrosine kinases, which include EGFR, erbB2, erbB3 and erbB4, are frequently involved in driving the proliferation and survival of tumour cells (reviewed in Olayioye et al., *EMBO J.,* 2000, 19, 3159). One mechanism in which this can be accomplished is by over expression of the receptor at the protein level, generally as a result of gene amplification. This has been observed in many common human cancers (reviewed in Klapper et al., *Adv. Cancer Res.* 2000, 77, 25) such as breast cancer (Sainsbury et al, *Brit. J. Cancer,* 1988, 58, 458; Guerin et al., *Oncogene Res.,* 1988, 3, 21; Slamon et al., *Science,* 1989, 244, 707; Klijn et al., *Breast Cancer Res. Treat.,* 1994, 29, 73 and reviewed in Salomon et al., *Crit. Rev. Oncol. Hematol.,* 1995, 19, 183), non-small cell lung cancers NSCLCs) including adenocarcinomas (Cerny et al., *Brit. J. Cancer,* 1986, 54, 265; Reubi et al., *Int. J. Cancer,* 1990, 45, 269; Rusch et al, *Cancer Research,* 1993, 53, 2379; Brabender et al, *Clin. Cancer Res.,* 2001, 7, 1850) as well as other cancers of the lung (Hendler et al., *Cancer Cells,* 1989, 7, 347; Ohsaki et al., *Oncol. Rep.,* 2000, 2, 603), bladder cancer (Neal et al., *Lancet,* 1985, 366; Chow et al., *Clin. Cancer Res.,* 2001, 7, 1957, Zhau et al., *Mol Carcinog.,* 3, 254), oesophageal cancer (Mukaida et al., *Cancer,* 1991, 68, 142), gastrointestinal cancer such as colon, rectal or stomach cancer (Bolen et al., *Oncogene Res.,* 1987, 1, 149; Kapitanovic et al., *Gastroenterology,* 2000, 112, 1103; Ross et al, *Cancer Invest.,* 2001, 19, 554), cancer of the prostate (Visakorpi et al., *Histochem. J.,* 1992, 24, 481; Kumar et al., 2000, 32, 73; Scher et al., *J. Natl. Cancer Inst.,* 2000, 92, 1866), leukaemia (Konaka et al., *Cell* 1984, 37, 1035, Martin-Subero et al. *Cancer Genet Cytogenet.,* 2001, 127, 174), ovarian (Hellstrom et al., *Cancer Res.,* 2001, 61, 2420), head and neck (Shiga et al., *Head Neck,* 2000, 22, 599) or pancreatic cancer (Ovotny et al., *Neoplasma,* 2001, 48, 188). As more human tumour tissues are tested for expression of the erbB family of receptor tyrosine kinases it is expected that their widespread prevalence and importance will be further enhanced in the future.

As a consequence of the mis-regulation of one or more of these receptors, it is widely believed that many tumours become clinically more aggressive and so correlate with a poorer prognosis for the patient (Brabender et al, *Clin. Cancer Res.,* 2001, 7, 1850; Ross et al, *Cancer Investigation,* 2001, 19, 554, Yu et al, *Bioassays,* 2000, 22.7, 673). In addition to these clinical findings, a wealth of pre-clinical information suggests that the erbB family of receptor tyrosine kinases are involved in cellular transformation. This includes the observations that many tumour cell lines over express one or more of the erbB receptors and that EGFR or erbB2 when transfected into non-tumour cells have the ability to transform these cells. This tumourigenic potential has been further verified as transgenic mice that over express erbB2 spontaneously develop tumours in the mammary gland. In addition to this, a number of pre-clinical studies have demonstrated that antiproliferative effects can be induced by knocking out one or more erbB activities by small molecule inhibitors, dominant negatives or inhibitory antibodies (reviewed in Mendelsohn et al., *Oncogene*, 2000, 19, 6550). Thus it has been recognised that inhibitors of these receptor tyrosine kinases should be of value as a selective inhibitor of the proliferation of mammalian cancer cells (Yaish et al. *Science*, 1988, 242, 933, Kolibaba et al, Biochimica et Biophysica Acta, 1997, 133, F217-F248; Al-Obeidi et al, 2000, *Oncogene*, 19, 5690-5701; Mendelsohn et al, 2000, *Oncogene*, 19, 6550-6565). In addition to this pre-clinical data, findings using inhibitory antibodies against EGFR and erbB2 (c-225 and trastuzumab respectively) have proven to be beneficial in the clinic for the treatment of selected solid tumours (reviewed in Mendelsohn et al, 2000, *Oncogene*, 19, 6550-6565).

Amplification and/or activity of members of the erbB type receptor tyrosine kinases have been detected and so have been implicated to play a role in a number of non-malignant proliferative disorders such as psoriasis (Ben-Bassat, *Curr. Pharm. Des.*, 2000, 6, 933; Elder et al., Science, 1989, 243, 811), benign prostatic hyperplasia (BPH) (Kumar et al, *Int. Urol. Nephrol.*, 2000, 32, 73), atherosclerosis and restenosis (Bokemeyer et al., *Kidney Int.*, 2000, 58, 549). It is therefore expected that inhibitors of erbB type receptor tyrosine kinases will be useful in the treatment of these and other non-malignant disorders of excessive cellular proliferation.

European patent application publication number EP 566 226 discloses certain 4-anilinoquinazolines that are receptor tyrosine kinase inhibitors.

International patent application publication numbers WO 96/33977, WO 96/33978, WO 96/33979, WO 96/33980, WO 96/33981, WO 97/30034, WO 97/38994 disclose that certain quinazoline derivatives, which bear an anilino substituent at the 4-position and a substituent at the 6- and/or 7-position, possess receptor tyrosine kinase inhibitory activity.

European patent application publication number EP 837 063 discloses aryl substituted 4-anilinoquinazoline derivatives carrying moiety containing an aryl or heteroaryl group at the 6- or 7-position on the quinazoline ring. The compounds are stated to be useful for treating hyperproliferative disorders.

International patent application publication numbers WO 97/30035 and WO 98/13354 disclose certain 4-anilinoquinazolines substituted at the 7-position are vascular endothelial growth factor receptor tyrosine kinase inhibitors.

WO 00/55141 discloses 6,7-substituted 4-anilinoquinazoline compounds characterised in that the substituents at the 6- and/or 7-position carry an ester-linked moiety (RO—CO).

WO 00/56720 discloses 6,7-dialkoxy-4-anilinoquinazoline compounds for the treatment of cancer or allergic reactions.

WO 02/41882 discloses 4-anilinoquinazoline compounds substituted at the 6- and/or 7-positions by a substituted pyrrolidinyl-alkoxy or piperidinyl-alkoxy group.

International patent application publication number WO 2004/006846 discloses that certain quinazoline derivatives, which bear an anilino substituent at the 4-position and a substituent at the 6- and 7-positions, are capable of modulating tyrosine kinase activity, particularly ephrin and EGFR. Particular compounds disclosed in WO 2004/006846 are: N-(3,4-dichlorophenyl)-7-[({4-[(3,5-dimethylisoxazol-4-yl)carbonyl]morpholin-2-yl}methyl)oxy]-6-(methyloxy)quinazolin-4-amine; N-(3,4-dichlorophenyl)-7-({[4-(furan-3-ylcarbonyl)morpholin-2-yl]methyl}oxy)-6-(methyloxy)quinazolin-4-amine; 7-[({4-[(2-chloropyridin-3-yl)carbonyl]morpholin-2-yl}methyl)oxy]-N-(3,4-dichlorophenyl)-6-(methyloxy)quinazolin-4-amine; and 7-[({4-[(6-chloropyridin-3-yl)carbonyl]morpholin-2-yl}methyl)oxy]-N-(3,4-dichlorophenyl)-6-(methyloxy)quinazolinamine.

We have now surprisingly found that other 4-(anilino)quinazoline derivatives possess potent anti-tumour activity. Without wishing to imply that the compounds disclosed in the present invention possess pharmacological activity only by virtue of an effect on a single biological process, it is believed that the compounds provide an anti-tumour effect by way of inhibition of one or more of the erbB family of receptor tyrosine kinases that are involved in the signal transduction steps which lead to the proliferation of tumour cells. In particular, it is believed that the compounds of the present invention provide an anti-tumour effect by way of inhibition of EGFR and/or erbB2 receptor tyrosine kinases.

Generally the compounds of the present invention possess potent inhibitory activity against the erbB receptor tyrosine kinase family, for example by inhibition of EGFR and/or erbB2 and/or erbB4 receptor tyrosine kinases, whilst possessing less potent inhibitory activity against other kinases. Furthermore, certain compounds of the present invention possess substantially better potency against the EGFR over that of the erbB2 tyrosine kinase. The invention also includes compounds that are active against all or a combination of EGFR, erbB2 and erbB4 receptor tyrosine kinases, thus potentially providing treatments for conditions mediated by one or more of these receptor tyrosine kinases.

Generally the compounds of the present invention exhibit favourable physical properties such as a high solubility whilst retaining high antiproliferative activity. Furthermore, many of the compounds according to the present invention are inactive or only weakly active in a hERG assay.

According to a first aspect of the invention there is provided a quinazoline derivative of the Formula I:

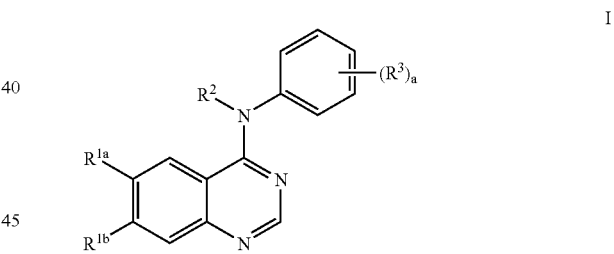

I wherein:

one of $R^{1a}$ or $R^{1b}$ is a group of sub-formula (i)

$$Q^2\text{-}X^1\text{—}Z\text{-}Q^1\text{-}X^2\text{—}O\text{—} \qquad (i)$$

where $X^2$ and $X^1$ are independently selected from a direct bond or a group —$[CR^4R^5]_m$—, wherein m is an integer from 1 to 6, Z is C(O), $SO_2$, —C(O)$NR^{10}$—, —$N(R^{10})$C(O)—, —C(O)O— or —OC(O)— where $R^{10}$ is hydrogen or (1-6C)alkyl, and each of $R^4$ and $R^5$ is independently selected from hydrogen, hydroxy, (1-4C)alkyl, halo(1-4C)alkyl, hydroxy(1-4C)alkyl, (1-4C)alkoxy(1-4C)alkyl, or $R^4$ and $R^5$ together with the carbon atom(s) to which they are attached form a (3-7) cycloalkyl ring, provided that when a group $R^4$ or $R^5$ is hydroxy, m is at least 2 and the carbon atom to which the hydroxy group is attached is not also attached to another oxygen or a nitrogen atom;

Q¹ is (3-7C)cycloalkylene or heterocyclyl group, which is optionally substituted by one or two substituents selected from halogeno, trifluoromethyl, trifluoromethoxy, cyano, nitro, hydroxy, amino, carboxy, carbamoyl, acryloyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (2-6C)alkenylthio, (2-6C)alkynylthio, (1-6C)alkylsulfinyl, (2-6C)alkenylsulfinyl, (2-6C)alkynylsulfinyl, (1-6C)alkylsulfonyl, (2-6C)alkenylsulfonyl, (2-6C)alkynylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, sulfamoyl, N-(1-6C)alkylsulfamoyl, N,N-di-[(1-6C)alkyl]sulfamoyl, (1-6C)alkanesulfonylamino,
N-(1-6C)alkyl-(1-6C)alkanesulfonylamino, carbamoyl(1-6C)alkyl, N-(1-6C)alkylcarbamoyl(1-6C)alkyl, N,N-di-[(1-6C)alkyl]carbamoyl(1-6C)alkyl, sulfamoyl(1-6C)alkyl, N-(1-6C)alkylsulfamoyl(1-6C)alkyl, N,N-di-[(1-6C)alkyl]sulfamoyl(1-6C)alkyl, (2-6C)alkanoyl(1-6C)alkyl, (2-6C)alkanoyloxy(1-6C)alkyl, (2-6C)alkanoylamino(1-6C)alkyl,
N-(1-6C)alkyl-(2-6C)alkanoylamino(1-6C)alkyl and (1-6C)alkoxycarbonyl(1-6C)alkyl;

Q² is an aryl or heteroaryl group, said aryl or heteroaryl group being optionally substituted by one of more substituents selected from halogeno, trifluoromethyl, trifluoromethoxy, cyano, nitro, hydroxy, amino, carboxy, carbamoyl, acryloyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (2-6C)alkenylthio, (2-6C)alkynylthio, (1-6C)alkylsulfinyl, (2-6C)alkenylsulfinyl, (2-6C)alkynylsulfinyl, (1-6C)alkylsulfonyl, (2-6C)alkenylsulfonyl, (2-6C)alkynylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, sulfamoyl, N-(1-6C)alkylsulfamoyl, N,N-di-[(1-6C)alkyl]sulfamoyl, (1-6C)alkanesulfonylamino,
N-(1-6C)alkyl-(1-6C)alkanesulfonylamino, carbamoyl(1-6C)alkyl, N-(1-6C)alkylcarbamoyl(1-6C)alkyl, N,N-di-[(1-6C)alkyl]carbamoyl(1-6C)alkyl, sulfamoyl(1-6C)alkyl, N-(1-6C)alkylsulfamoyl(1-6C)alkyl, N,N-di-[(1-6C)alkyl]sulfamoyl(1-6C)alkyl, (2-6C)alkanoyl(1-6C)alkyl, (2-6C)alkanoyloxy(1-6C)alkyl, (2-6C)alkanoylamino(1-6C)alkyl,
N-(1-6C)alkyl-(2-6C)alkanoylamino(1-6C)alkyl and (1-6C)alkoxycarbonyl(1-6C)alkyl, and wherein any (1-6C)alkyl, (2-8C)alkenyl, (2-8C)alkynyl and (2-6C)alkanoyl substituent on Q¹ or Q² optionally bears one or more substituents (for example 1, 2 or 3) which may be the same or different selected from halogeno, hydroxy and (1-6C)alkyl and/or optionally a substituent selected from cyano, nitro, carboxy, (2-8C)alkenyl, (2-8C)alkynyl, (1-6C)alkoxy, hydroxy(1-6C)alkoxy, (1-4C)alkoxy(1-6C)alkoxy, (2-6C)alkanoyl, (2-6C)alkanoyloxy and NR$^a$R$^b$, wherein is hydrogen or (1-4C)alkyl and R$^b$ is hydrogen or (1-4C)alkyl, and wherein any (1-4C)alkyl in R$^a$ or R$^b$ optionally bears one or more substituents (for example 1, 2 or 3) which may be the same or different selected from halogen and hydroxy and/or optionally a substituent selected from cyano, nitro, (2-4C)alkenyl, (2-4C)alkynyl, (1-4C)alkoxy, hydroxy(1-4C)alkoxy and (1-2C)alkoxy(1-4C)alkoxy, or R$^a$ and R$^b$ together with the nitrogen atom to which they are attached form a 4, 5 or 6 membered ring, which optionally bears 1 or 2 substituents, which may be the same or different, on an available ring carbon atom selected from halogeno, hydroxy, (1-4C)alkyl and (1-3C)alkylenedioxy, and may optionally bear on any available ring nitrogen a substituent (provided the ring is not thereby quaternised) selected from (1-4C)alkyl, (2-4C)alkanoyl and (1-4C)alkylsulfonyl, and wherein any (1-4C)alkyl or (2-4C)alkanoyl group present as a substituent on the ring formed by R$^a$ and R$^b$ together with the nitrogen atom to which they are attached, optionally bears one or more substituents (for example 1, 2 or 3) which may be the same or different selected from halogeno and hydroxy and/or optionally a substituent selected from (1-4C)alkyl and (1-4C)alkoxy;

and wherein any heterocyclyl group Q¹-group optionally bears 1 or 2 oxo (=O) or thioxo (=S) substituents;

and the other of R$^{1a}$ or R$^{1b}$ is a group R¹ which is selected from hydrogen, hydroxy, (1-6C)alkoxy, (2-6C)alkenyloxy, (2-6C)alkynyloxy, or a group of the formula:

Q⁴-X³— wherein X³ is a direct bond or is selected from O or S, and Q⁴ is (3-7C)cycloalkyl, (3-7C)cycloalkyl-(1-6C)alkyl, (3-7C)cycloalkenyl, (3-7C)cycloalkenyl-(1-6C)alkyl, heterocyclyl or heterocyclyl-(1-6C)alkyl, and wherein adjacent carbon atoms in any (2-6C)alkylene chain within a R¹ substituent are optionally separated by the insertion into the chain of a group selected from O, S, SO, SO₂, N(R⁴), CO, CH(OR⁴), CON(R⁴), N(R⁴)CO, SO₂N(R⁴), N(R⁴)SO₂, CH=CH and C≡C wherein R⁴ is hydrogen or (1-6C)alkyl, and wherein any CH₂=CH— or HC≡C— group within a R¹ substituent optionally bears at the terminal CH₂= or HC≡ position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

Q⁵-X⁴— wherein X⁴ is a direct bond or is selected from CO and N(R⁵)CO, wherein R⁵ is hydrogen or (1-6C)alkyl, and Q⁵ is heterocyclyl or heterocyclyl-(1-6C)alkyl, and wherein any alkyl or alkylene group within a R¹ substituent optionally bears one or more halogeno, (1-6C)alkyl, hydroxy, cyano, amino, carboxy, carbamoyl, sulfamoyl, (1-6C)alkoxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino,
N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

—X⁵-Q⁶ wherein X⁵ is a direct bond or is selected from O, S, SO, SO₂, N(R⁶), CO, CH(OR⁶), CON(R⁶), N(R⁶)CO, SO₂N(R⁶), N(R⁶)SO₂, C(R⁶)₂O, C(R⁶)₂S and C(R⁶)₂N(R⁶), wherein R⁶ is hydrogen or (1-6C)alkyl, and Q⁶ is (3-7C)cycloalkyl, (3-7C)cycloalkyl-(1-6C)alkyl, (3-7C)cycloalkenyl, (3-7C)cycloalkenyl-(1-6C)alkyl, heterocyclyl or heterocyclyl-(1-6C)alkyl, and wherein any heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, formyl, mercapto, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino, and N-(1-6C)alkyl-(1-6C)alkanesulfonylamino, or from a group of the formula:

$$-X^6-R^7$$

wherein $X^6$ is a direct bond or is selected from O, N($R^8$) and C(O), wherein $R^8$ is hydrogen or (1-6C)alkyl, and $R^7$ is halogeno-(1-6C)alkyl, hydroxy-(1-6C)alkyl, carboxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, (1-6C)alkoxycarbonylamino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (2-6C)alkanoyl-(1-6C)alkyl or (1-6C)alkoxycarbonyl-(1-6C)alkyl, and wherein any heterocyclyl group within a substituent on $R^1$ optionally bears 1 or 2 oxo or thioxo substituents;

$R^2$ is selected from hydrogen and (1-6C)alkyl;

each $R^3$, which may be the same or different, is selected from halogeno, cyano, nitro, hydroxy, amino, carboxy, carbamoyl, sulfamoyl, trifluoromethyl, (1-6C)alkyl, (2-8C)alkenyl, 2-8C)alkynyl, (1-6C)alkoxy, (2-6C)alkenyloxy, (2-6C)alkynyloxy, (1-6C)alkylthio, 1-6C)alkylsulfinyl, (1-6C)alkylsulfonyl, (1-6C)alkylamino, di-[(1-6C)alkyl]amino, 1-6C)alkoxycarbonyl, N-(1-6C)alkylcarbamoyl, N,N-di-[(1-6C)alkyl]carbamoyl, N-(1-6C)alkylsulfamoyl, and N,N-di-[(1-6C)alkyl]sulfamoyl a is 1, 2, 3, 4 or 5;

or a pharmaceutically acceptable salt thereof;

subject to the following provisos:
(i) when $Q^2$ is aryl, then $R^{1a}$ is a group of sub-formula (i) defined above and $R^{1b}$ is the group $R^1$ defined above; and
(ii) the compound of formula I is not one of the following:
N-(3,4-dichlorophenyl)-7-[({4-[(3,5-dimethylisoxazol-4-yl)carbonyl]morpholin-2-yl}methyl)oxy]-6-(methyloxy)quinazolin-4-amine;
N-(3,4-dichlorophenyl)-7-({[4-(furan-3-ylcarbonyl)morpholin-2-yl]methyl}oxy)-6-(methyloxy)quinazolin-4-amine;
7-[({4-[(2-chloropyridin-3-yl)carbonyl]morpholin-2-yl}methyl)oxy]-N-(3,4-dichlorophenyl)-6-(methyloxy)quinazolin-4-amine; or
7-[({4-[(6-chloropyridin-3-yl)carbonyl]morpholin-2-yl}methyl)oxy]-N-(3,4-dichlorophenyl)-6-(methyloxy)quinazolin-4-amine.

In this specification the generic term "alkyl" includes both straight-chain and branched-chain alkyl groups such as propyl, isopropyl and tert-butyl, and (3-8C)cycloalkyl groups such as cyclopropyl, cyclobutyl, cyclopentyl, cyclohexyl and cycloheptyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1-6C)alkoxy includes methoxy, ethoxy, cyclopropyloxy and cyclopentyloxy, (1-6C)alkylamino includes methylamino, ethylamino, cyclobutylamino and cyclohexylamino, and di-[(1-6Calkyl]amino includes dimethylamino, diethylamino, N-cyclobutyl-N-methylamino and N-cyclohexyl-N-ethylamino.

The term "aryl" refers to aromatic hydrocarbon ring systems and includes, for example, phenyl, indenyl, indanyl, naphthyl and fluorenyl. Particular values of aryl are phenyl and naphthyl, preferably phenyl.

The terms "heterocyclic" or "heterocyclyl" include ring structures that may be mono- or bicyclic and contain from 3 to 15 atoms, at least one of which, and suitably from 1 to 4 of which, is a heteroatom such as oxygen, sulphur or nitrogen. Rings may be aromatic, on-aromatic or partially aromatic in the sense that one ring of a fused ring system may be aromatic and the other non-aromatic. Particular examples of such ring systems include furyl, benzofuranyl, tetrahydrofuryl, chromanyl, thienyl, benzothienyl, pyridyl, piperidinyl, quinolyl, 1,2,3,4-tetrahydroquinolinyl, isoquinolyl, 1,2,3,4-tetrahydroisoquinolinyl, pyrazinyl, piperazinyl, pyrimidinyl, pyridazinyl, isoquinolinyl, phthalazinyl, purinyl, quinoxalinyl, quinazolinyl, cinnolinyl, pyrrolyl, pyrrolidinyl, indolyl, indolinyl, isoindolyl, imidazolyl, benzimidazolyl, pyrazolyl, indazolyl, oxazolyl, benzoxazolyl, isoxazolyl, thiazolyl, benzothiazolyl, isothiazolyl, morpholinyl, 4H-1,4-benzoxazinyl, 4H-1,4-benzothiazinyl, 1,2,3-triazolyl, 1,2,4-triazolyl, oxadiazolyl, furazanyl, thiadiazolyl, tetrazolyl, dibenzofuranyl, dibenzothienyl oxiranyl, oxetanyl, azetidinyl, tetrahydropyranyl, oxepanyl, oxazepanyl, tetrahydro-1,4-thiazinyl, 1,1-dioxotetrahydro-1,4-thiazinyl, homopiperidinyl, homopiperazinyl, dihydropyridinyl, tetrahydropyridinyl, dihydropyrimidinyl, tetrahydropyrimidinyl, tetrahydrothienyl, tetrahydrothiopyranyl or thiomorpholinyl.

Where rings include nitrogen atoms, these may carry a hydrogen atom or a substituent group such as an (C1-6)alkyl group if required to fulfil the bonding requirements of nitrogen, or they may be linked to the rest of the structure by way of the nitrogen atom. A nitrogen atom within a heterocyclyl group may be oxidized to give the corresponding N oxide.

The term "heteroaryl" however refers to heterocyclic groups which are completely aromatic in nature. Particular examples of such ring systems include furyl, benzofuranyl, thienyl, benzothienyl, pyridyl, quinolyl, isoquinolyl, phthalazinyl, purinyl, pyrazinyl, pyrimidinyl, pyridazinyl, quinoxalinyl, quinazolinyl, cinnolinyl, pyrrolyl, indolyl, indolinyl, isoindolyl, imidazolyl, benzimidazolyl, pyrazolyl, indazolyl, oxazolyl, benzoxazolyl, isoxazolyl, thiazolyl, benzothiazolyl, isothiazolyl, 1,2,3-triazolyl, 1,2,4-triazolyl, oxadiazolyl, furazanyl, thiadiazolyl, tetrazolyl, dibenzofuranyl or dibenzothienyl.

In an embodiment of the invention, $R^{1a}$ is a group of sub-formula (i) and $R^{1b}$ is a group $R^1$.

In a further embodiment, $R^{1a}$ is a group $R^1$ and $R^{1b}$ is a group of sub-formula (i).

Particular examples of groups $R^1$ are hydrogen, hydroxy, (1-6C)alkoxy, (2-6C)alkenyloxy, (2-6C)alkynyloxy, or a group of the formula:

$$Q^4-X^3-$$

wherein $X^3$ is a direct bond or is O or S (particularly a direct bond or 0), and $Q^4$ is (3-7C)cycloalkyl, (3-7C)cycloalkyl-(1-6C)alkyl, (3-7C)cycloalkenyl, (3-7C)cycloalkenyl-(1-6C)

alkyl, heterocyclyl or heterocyclyl-(1-6C)alkyl, and wherein any alkyl or alkylene group within a $R^1$ substituent optionally bears one or more halogeno, (1-6C)alkyl, hydroxy, cyano, amino, carboxy, carbamoyl, sulfamoyl, (1-6C)alkoxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino.

In particular $R^1$—is selected from hydrogen, (1-6C)alkoxy and (1-6C)alkoxy(1-6C)alkoxy, wherein any (1-6C)alkoxy group in $R^1$ optionally bears one or more hydroxy substituents (suitably 1 or 2) and/or a substituent selected from amino, (1-4C)alkylamino, di-[(1-4C)alkyl]amino, carbamoyl, N-(1-4C)alkylcarbamoyl and N,N-di-[(1-4C)alkyl]carbamoyl, sulfamoyl, N-(1-4C)alkylsulfamoyl and N,N-di-[(1-4C)alkyl]sulfamoyl.

For instance, $R^1$ is selected from hydrogen, (1-6C)alkoxy and (1-4C)alkoxy(1-6C)alkoxy, and wherein any (1-6C)alkoxy group within $R^1$ optionally bears 1, 2 or 3 substituents, which may be the same or different, selected from hydroxy, fluoro and chloro, for example $R^1$ is selected from methoxy, ethoxy, isopropyloxy, cyclopropylmethoxy, 2-hydroxyethoxy, 2-fluoroethoxy, 2-methoxyethoxy, 2,2-difluoroethoxy, 2,2,2-trifluoroethoxy or 3-hydroxy-3-methylbutoxy.

In particular $R^1$ is selected from hydrogen, (1-4C)alkoxy and (1-4C)alkoxy(1-4C)alkoxy. For instance, $R^1$ is selected from hydrogen, methoxy, ethoxy and 2-methoxyethoxy and 2-hydroxyethoxy. A particular example of a group $R^1$ is methoxy.

In a particular embodiment, $X^2$ or $X^1$ is a group $C(R^4R^5)_m$, wherein $R^4$ and $R^5$, which may be the same or different, are selected from hydrogen, (1-4C)alkyl, hydroxymethyl, hydroxyethyl or halo(C1-2)alkyl, such as $CH_2CH_2F$, $CH_2CHF_2$ or $CH_2CF_3$. Where $R^4$ and $R^5$ together with the carbon atom(s) to which they are attached form a (3-7C) cycloalkyl ring, it is preferably that both $R^4$ and $R^5$ groups are on the same carbon atom. Thus a particular example of such a group is a cyclopropyl group.

In particular, $R^4$ and $R^5$ are hydrogen. The value of m is suitably 0, 1 or 2. In particular, m is 1 or 0.

In a particular embodiment, $X^2$ is a direct bond.

$X^1$ is suitably a direct bond or an (1-6C)alkylene group such as methyl or ethyl, and in particular is a direct bond.

Z is suitably selected from C(O), $SO_2$, —C(O)$NR^{10}$—, —$NR^{10}$—C(O)—, —O—C(O)— or —C(O)O—, where $R^{10}$ is hydrogen or (1-3C)alkyl such as methyl.

Preferably any $R^{10}$ group is hydrogen.

In particular compounds of Formula (I), Z is selected from C(O), —$NR^{10}$—C(O)—, and —O—C(O)—.

In an embodiment, Z is —$NR^{10}$—C(O)—, wherein $R^{10}$ is H.

In a further embodiment, Z is —O—C(O)—.

Preferably, Z is C(O).

A suitable value for $Q^1$ when it is (3-7C)cycloalkyl is, for example, cyclopropyl, cyclobutyl, cyclopentyl, cyclohexyl, cycloheptyl or bicyclo[2.2.1]heptyl.

When $Q^1$ is heterocyclyl it is suitably a non-aromatic saturated (i.e. with the maximum degree of saturation) or partially saturated (i.e. ring systems retaining some, but not the full, degree of unsaturation) 3 to 10 membered monocyclic ring with up to five heteroatoms selected from oxygen, nitrogen and sulfur (but not containing any O—O, O—S or S—S bonds), and linked via a ring carbon atom, or a ring nitrogen atom (provided the ring is not thereby quaternised). Suitable values for $Q^1$ include for example, oxiranyl, oxetanyl, azetidinyl, tetrahydrofuranyl, tetrahydropyranyl, oxepanyl, oxazepanyl, pyrrolinyl, pyrrolidinyl, morpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl, tetrahydropyrimidinyl, tetrahydrothienyl, tetrahydrothiopyranyl, thiomorpholinyl, more specifically including for example, tetrahydrofuran-3-yl, tetrahydrofuran-2-yl-, tetrahydropyran-4-yl, tetrahydrothien-3-yl, tetrahydrothiopyran-4-yl, pyrrolidin-3-yl, pyrrolidin-2-yl, 3-pyrrolin-3-yl-, morpholino, 1,1-dioxotetrahydro-4H-1,4-thiazin-4-yl, piperidino, piperidin-4-yl, piperidin-3-yl, piperidin-2-yl, homopiperidin-3-yl, homopiperidin-4-yl, piperazin-1-yl, 1,4-oxazepanyl, or 1,2,3,6-tetrahydropyridin-4-yl. A nitrogen or sulfur atom within a heterocyclyl group may be oxidized to give the corresponding N or S oxide(s), for example 1,1-dioxotetrahydrothienyl, 1-oxotetrahydrothienyl, 1,1-dioxotetrahydrothiopyranyl or 1-oxotetrahydrothiopyranyl. A suitable value for such a group which bears 1 or 2 oxo or thioxo substituents is, for example, 2-oxopyrrolidinyl, 2-oxopiperazinyl, 2-thioxopyrrolidinyl, 2-oxopiperidinyl, 2,5-dioxopyrrolidinyl or 2,6-dioxopiperidinyl.

Particular values for $Q^1$ include, for example, non-aromatic saturated or partially saturated 3 to 7 membered monocyclic heterocyclyl rings with 1 ring nitrogen or sulfur heteroatom and optionally 1 or 2 heteroatoms selected from nitrogen, oxygen and sulfur. Examples of such rings include azetidinyl, oxazepanyl, pyrrolinyl, pyrrolidinyl, morpholinyl, tetrahydro-1,4-thiazinyl, piperidinyl, homopiperidinyl, piperazinyl, homopiperazinyl, dihydropyridinyl, tetrahydropyridinyl, dihydropyrimidinyl, tetrahydropyrimidinyl, tetrahydrothienyl, tetrahydrothiopyranyl or thiomorpholinyl.

Further particular values for $Q^1$ include, for example, non-aromatic saturated or partially saturated 3 to 7 membered monocyclic heterocyclyl rings with 1 ring nitrogen heteroatom and optionally 1 or 2 heteroatoms selected from nitrogen and sulfur, which rings are linked to $X^2$—O by a ring carbon atom, such as, for example, azetidinyl, pyrrolinyl, pyrrolidinyl, tetrahydro-1,4-thiazinyl, piperidinyl, homopiperidinyl, piperazinyl, homopiperazinyl, dihydropyridinyl, tetrahydropyridinyl, dihydropyrimidinyl, tetrahydropyrimidinyl, tetrahydrothiopyranyl or thiomorpholinyl. More particularly $Q^1$ is a non-aromatic saturated or partially saturated 4, 5 or 6 membered monocyclic heterocyclyl ring with 1 or 2 ring nitrogen heteroatom(s), which ring is linked to the group $X^2$—O— by a ring carbon atom, more particularly pyrrolidin-3-yl, pyrrolidin-2-yl, 3-pyrrolin-3-yl-, piperidin-4-yl, piperidin-3-yl, piperidin-2-yl, homopiperidin-3-yl, homopiperidin-4-yl, piperazin-2-yl, piperazin-3-yl, or 1,2,3,6-tetrahydropyridin-4-yl. A nitrogen atom within a heterocyclyl group may be oxidized to give the corresponding N oxide.

In a particular embodiment, $Q^1$ is piperidin-4-yl.

In a further embodiment, $Q^1$ is piperidin-3-yl.

Suitably, the group $Q^2$-$X^1$—Z— is linked to a nitrogen atom on a heterocyclic $Q^1$, in particular when the group Z is a carbonyl group C(O).

The group $Q^1$ optionally carries further substituents.

In one embodiment, any available nitrogen in a heterocyclic $Q^1$ optionally bears a substituent (where such substitution does not result in quaternization) selected from trifluoromethyl, cyano, carbamoyl, trifluoromethyl, (1-6C)alkyl, (2-8C)alkenyl, (2-8C)alkynyl, (1-6C)alkylthio, (1-6C)alkylsulfinyl, (1-6C)alkylsulfonyl, (1-6C)alkoxycarbonyl, N-(1-6C)alkylcarbamoyl, N,N-di-[(1-6C)alkyl]carbamoyl, (2-6C)alkanoyl, sulfamoyl, N-(1-6C)alkylsulfamoyl, N,N-di-[(1-6C)alkyl]sulfamoyl, carbamoyl(1-6C)alkyl, N-(1-6C)alkylcarbamoyl(1-6C)alkyl, N,N-di-[(1-6C)alkyl]carbamoyl(1-6C)alkyl, (2-6C)alkanoyl(1-6C)alkyl, (2-6C)alkanoyloxy(1-6C)alkyl, (2-6C)alkanoylamino(1-6C)alkyl, N-(1-6C)alkyl-(2-6C)alkanoylamino(1-6C)alkyl and (1-6C)alkoxycarbonyl(1-6C)alkyl, wherein any (1-6C)alkyl, (2-8C)alkenyl, (2-8C)alkynyl and (2-6C)alkanoyl group within an optional substituent on an available nitrogen is optionally substituted by one or more substituents, which maybe the same or different, selected from fluoro, chloro, hydroxy and (1-4C)alkyl, and/or optionally a substituent selected from cyano, nitro, carboxy, (1-4C)alkoxy, hydroxy(1-4C)alkoxy and $NR^aR^b$, wherein $R^a$ is hydrogen or (1-4C)alkyl and Rb is hydrogen or (1-4C)alkyl.

$Q^1$ optionally bears on any available carbon atom in the ring 1 or 2 (suitably 1) substituents selected from halogeno, trifluoromethyl, cyano, nitro, hydroxy, amino, carboxy, carbamoyl, (1-4C)alkyl, (2-6C)alkenyl, (2-6C)alkynyl, (1-6C)alkoxy, (1-6C)alkylamino, di-[(1-6C)alkyl]amino, (2-6C)alkanoylamino, N-(1-6C)alkyl-(2-6C)alkanoylamino, hydroxy(1-6C)alkyl, cyano(1-6C)alkyl, amino(1-6C)alkyl, (1-6C)alkylamino(1-6C)alkyl, di-[(1-6C)alkyl]amino(1-6C)alkyl and (1-6C)alkoxy(1-6C)alkyl.

$Q^1$ optionally also bears 1 or 2 oxo or thioxo substituents.

In particular however, $Q^1$ carries no substituents other than the group $Q^2-X^1-Z-$.

Where $Q^2$ is heteroaryl, it is suitably a 5 or 6-membered heteroaryl ring which optionally contains one or more heteroatoms selected from oxygen, nitrogen or sulphur. In particular, $Q^2$ is selected from furyl, thienyl, pyridyl, pyrazinyl, pyrimidinyl, pyridazinyl, pyrrolyl, imidazolyl, pyrazolyl, oxazolyl, isoxazolyl, thiazolyl, isothiazolyl, 1,2,3-triazolyl, 1,2,4-triazolyl, oxadiazolyl, furazanyl, thiadiazolyl, tetrazolyl, or a 9 or 10 membered bicyclic heteroaryl ring system such as quinolinyl, isoquinolinyl, cinnolinyl, quinazolinyl, phthalazinyl, quinoxalinyl, indolyl, isoindolyl, benzofuranyl, benzothienyl, benzimidazolyl, benzothiazolyl or purinyl.

Particular examples include 5-membered rings such as furyl, thienyl, pyrrolyl, pyrazolyl, imidazolyl, oxazolyl, isoxazolyl, thiazolyl, isothiazolyl, 1,2,3-triazolyl, 1,2,4-triazolyl, oxadiazolyl, furazanyl, thiadiazolyl or tetrazolyl.

Further examples include 9- or 10-membered bicyclic ring systems such as indolyl, quinolinyl, benzofuranyl, or benzothienyl.

More particularly, $Q^2$ is selected from isoxazolyl, furyl, thienyl, pyridyl, pyrazolyl, pyrrolyl, indolyl, quinolinyl, benzofuranyl, or benzothienyl.

Where $Q^2$ is aryl, it is suitably selected from phenyl and naphthyl, particularly phenyl.

Suitable substituents for group $Q^2$ include $Q^2$ optionally bearing 1 or 2 substituents, which may be the same or different, selected from halogeno, hydroxy, nitro, amino, cyano, carbamoyl, (1-4C)alkyl, (1-4C)alkoxy, (2-4C)alkanoyl and (1-4C)alkylsulfonyl, (1-4C)alkylamino, di[(1-4C)alkyl]amino, N-[(1-4C)alkyl]carbamoyl, and N,N-di[(1-4C)alkyl]carbamoyl.

and wherein any (1-4C)alkyl, or (2-4C)alkanoyl group within $Q^2$ optionally bears 1 or 2 substituents, which may be the same or different, selected from halogeno, hydroxy and (1-6C)alkyl and/or optionally a substituent selected from cyano, (2-8C)alkenyl, (2-8C)alkynyl, (1-6C)alkoxy, (2-6C)alkanoyl, (2-6C)alkanoyloxy and $NR^aR^b$, wherein $R^a$ is hydrogen or (1-4C)alkyl and $R^b$ is hydrogen or (1-4C)alkyl, and wherein any (1-4C)alkyl in $R^a$ or $R^b$ optionally bears one or more substituents (for example 1, 2 or 3) which may be the same or different selected from halogeno and hydroxy and/or optionally a substituent selected from cyano, and (1-4C)alkoxy, or $R^a$ and $R^b$ together with the nitrogen atom to which they are attached form a 4, 5 or 6 membered ring which does not contain oxygen, which ring optionally bears 1 or 2 substituents, which may be the same or different, on an available ring carbon atom selected from halogeno, hydroxy, (1-4C)alkyl and (1-3C)alkylenedioxy, and may optionally bear on any available ring nitrogen a substituent (provided the ring is not thereby quaternised) selected from (1-4C)alkyl, (2-4C)alkanoyl and (1-4C)alkylsulfonyl, and wherein any (1-4C)alkyl or (2-4C)alkanoyl group present as a substituent on the ring formed by $R^a$ and $R^b$ together with the nitrogen atom to which they are attached optionally bears one or more substituents (for example 1, 2 or 3), which may be the same or different, selected from halogeno and hydroxy and/or optionally a substituent selected from (1-4C)alkyl and (1-4C)alkoxy.

Particular examples of substituents for $Q^2$ include one or two groups, which may be the same or different, selected from halogeno (particularly chloro and bromo and fluoro), hydroxy, nitro, amino, cyano, carbamoyl, (1-4C)alkyl, (1-4C)alkoxy, (2-4C)alkanoyl and (1-4C)alkylsulfonyl, [(1-4C)alkyl]amino, di[(1-4C)alkyl]amino, N-[(1-4C)alkyl]carbamoyl, and N,N-di[(1-4C)alkyl]carbamoyl.

and wherein any (2-4C)alkanoyl group in a substituent on $Q^2$ optionally bears one or two substituents, which may be the same or different, selected from hydroxy and (1-3C)alkyl, and wherein any (1-4C)alkyl group in a substituent on $Q^2$ optionally bears one or two substituents, which may be the same or different, selected from hydroxy, (1-4C)alkoxy and halogeno (particularly chloro and more particularly fluoro).

Suitably $Q^2$ is unsubstituted or substituted by a (1-4C)alkyl group such as methyl, a (1-4C)alkoxy group such as methoxy, halogeno (particularly bromo, chloro or fluoro), amino, nitro, cyano, carbamoyl, di-[(1-4C)alkyl]amino such as dimethylamino, and N,N-di[(1-4C)alkyl]carbamoyl such as N,N-dimethylcarbamoyl.

Suitably $Q^2$ is a heteroaryl group optionally substituted by a (1-4C)alkyl group such as methyl, halogeno (particularly bromo, chloro or fluoro), amino, nitro, cyano, [(1-4C)alkyl]amino, di-[(1-4C)alkyl]amino such as dimethylamino, N-[(1-4C)alkyl]carbamoyl, and N,N-di[(1-4C)alkyl]carbamoyl such as N,N-dimethylcarbamoyl.

Suitably $Q^2$ is an aryl group optionally substituted by a (1-4C)alkyl group such as methyl, halogeno (particularly bromo, chloro or fluoro), amino, nitro, [(1-4C)alkyl]amino, di-[(1-4C)alkyl]amino such as dimethylamino, N-[(1-4C)alkyl]carbamoyl, and N,N-di[(1-4C)alkyl]carbamoyl such as N,N-dimethylcarbamoyl.

$R^2$ is suitably hydrogen or (1-3C)alkyl such as methyl, but in particular is hydrogen.

In an embodiment of the invention, a is 1, 2 or 3.

Examples of suitable $R^3$ substituents are halogeno, carbamoyl, trifluoromethyl, (1-6C)alkyl, (2-8C)alkenyl, (2-8C)alkynyl, N-(1-6C)alkylcarbamoyl, or N,N-di-[(1-6C)alkyl]carbamoyl.

In a particular embodiment, when $R^3$ is in the para position on the anilino ring it is selected from halogeno, cyano, nitro, hydroxy, amino, trifluoromethyl, (1-6C)alkyl, (2-8C)alkenyl, (2-8C)alknyl, (1-6C)alkoxy, (2-6C)alkenyloxy, (2-6C)alkynyloxy, (1-6C)alkylthio, (1-6C)alkylamino and di-[(1-6C)alkyl]amino.

In a particular embodiment at least one $R^3$, and suitable all $R^3$ groups are halogeno, such as chloro or fluoro.

Particular examples of the group of sub-formula (ii)

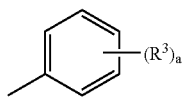

in formula (I) are groups of sub-formula in formula (I) are groups of sub-formula (iii)

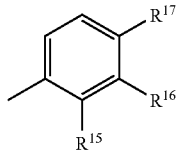

where one of $R^{15}$ or $R^{17}$ is hydrogen and the other is halogeno, such as chloro or fluoro, and preferably fluoro, and $R^{16}$ is halogeno such as chloro or fluoro and particularly chloro.

Particular examples of such groups are 3-chloro-2-fluorophenyl, or 3-chloro-4-fluorophenyl, especially 3-chloro-2-fluorophenyl.

In a preferred embodiment of the invention, the compounds have the general structural formula (A) shown below:

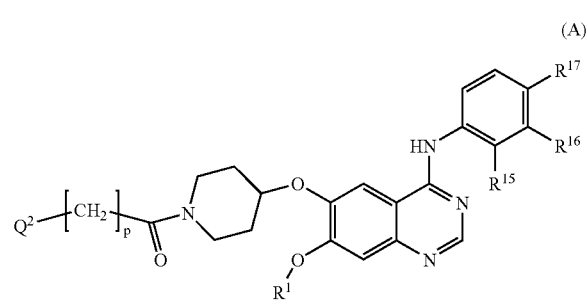

wherein $R^{15}$, $R^{16}$, and $R^{17}$ are as hereinbefore defined;
$R^1$ is (1-4C)alkyl;
p is 0, 1 or 2; and
$Q^2$ is aryl or heteroaryl as hereinbefore defined, which may be optionally substituted as hereinbefore defined;
or a pharmaceutically acceptable salt thereof.

In the compounds of formula (A), or a pharmaceutically acceptable salt thereof, $R^1$, $R^{15}$, $R^{16}$, $R^{17}$, p and $Q^2$ may have any of the meanings hereinbefore defined, or as defined in any one of paragraphs (a) to (n) hereinafter:

(a) $R^1$ is methyl;
(b) $R^{15}$ is hydrogen, fluoro or chloro;
(c) $R^{15}$ is fluoro;
(d) $R^{16}$ is fluoro or chloro;
(e) $R^{16}$ is fluoro;
(f) $R^{17}$ is hydrogen, fluoro or chloro;
(g) $R^{17}$ is hydrogen;
(h) p is 0 or 1;
(i) p is 0;
(j) p is 1;
(k) $Q^2$ is an optionally substituted 5- or 6-membered or 9- or 10-membered heteraryl ring (as hereinbefore defined);
(l) $Q^2$ is a heteroaryl ring selected from the group consisting of isoxazolyl, furyl, thienyl, pyridyl, pyrazolyl, pyrrolyl, indolyl, quinolinyl, benzofuranyl, and benzothienyl, and wherein said ring may be optionally substituted by halogeno (particularly bromo, chloro or fluoro), amino, nitro, cyano, (1-4C)alkyl, [(1-4C)alkyl]amino, di-[(1-4C)alkyl]amino such as dimethylamino, N-[(1-4C)alkyl]carbamoyl and N,N-di[(1-4C)alkyl]carbamoyl such as N,N-dimethylcarbamoyl;
(m) $Q^2$ is phenyl optionally substituted by halogeno (particularly bromo, chloro or fluoro), amino, nitro, cyano, (14C)alkyl, [(1-4C)alkyl]amino, di-[(1-4C)alkyl]amino such as dimethylamino, N-[(1-4C)alkyl]carbamoyl and N,N-di[(1-4C)alkyl]carbamoyl such as N,N-dimethylcarbamoyl;
(n) $Q^2$ is phenyl.

In particular compounds of formula (A) above, $R^1$ is methyl, $R^{15}$ is fluoro, $R^{16}$ is chloro, $R^{17}$ is hydrogen, p is 0 or 1, and $Q^2$ is aryl or heteroaryl as hereinbefore defined or as defined in any one of paragraphs (k) to (n) above.

In a further preferred embodiment of the invention, the compounds have the general structural formula (B) shown below:

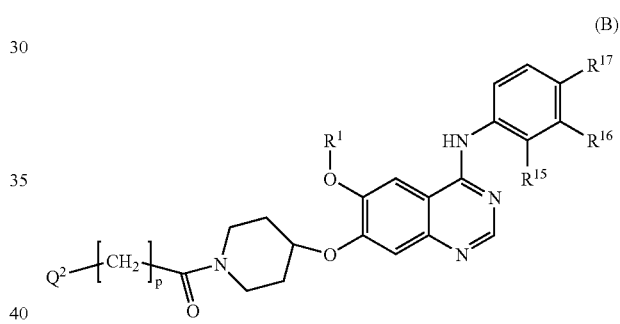

wherein
$R^{15}$, $R^{16}$, and $R^{17}$ are as hereinbefore defined;
$R^1$ is (1-4C)alkyl;
p is 0, 1 or 2; and
$Q^2$ is heteroaryl as hereinbefore defined, which may be optionally substituted as hereinbefore defined;
or a pharmaceutically acceptable salt thereof.

In the compounds of formula (B), or a pharmaceutically acceptable salt thereof, $R^1$, $R^{15}$, $R^{16}$, $R^{17}$, p and $Q^2$ may have any of the meanings hereinbefore defined, or as defined in any one of paragraphs (a) to (l) hereinafter:

(a) $R^1$ is methyl;
(b) $R^{15}$ is hydrogen, fluoro or chloro;
(c) $R^{15}$ is fluoro;
(d) $R^{16}$ is fluoro or chloro;
(e) $R^{16}$ is fluoro;
(f) $R^{17}$ is hydrogen, fluoro or chloro;
(g) $R^{17}$ is hydrogen;
(h) p is 0 or 1;
(i) p is 0;
(j) p is 1;
(k) $Q^2$ is an optionally substituted 5- or 6-membered or 9- or 10-membered heteraryl ring (as hereinbefore defined);

(l) $Q^2$ is a heteroaryl ring selected from the group consisting of isoxazolyl, furyl, thienyl, pyridyl, pyrazolyl, pyrrolyl, indolyl, quinolinyl, benzofuranyl, and benzothienyl, and wherein said ring may be optionally substituted by halogeno (particularly bromo, chloro or fluoro), amino, nitro, cyano, (14C)alkyl, [(1-4C)alkyl]amino, di-[(1-4C)alkyl]amino such as dimethylamino, N-[(1-4C)alkyl]carbamoyl and N,N-di[(1-4C)alkyl]carbamoyl such as N,N-dimethylcarbamoyl.

In particular compounds of formula (B) above, $R^1$ is methyl, $R^{15}$ is fluoro, $R^{16}$ is chloro, $R^{17}$ is hydrogen, p is 0 or 1, and $Q^2$ is heteroaryl as hereinbefore defined or as defined in either paragraphs (k) and (l) above.

In a further preferred embodiment of the invention, the compounds have the general structural formula (C) shown below:

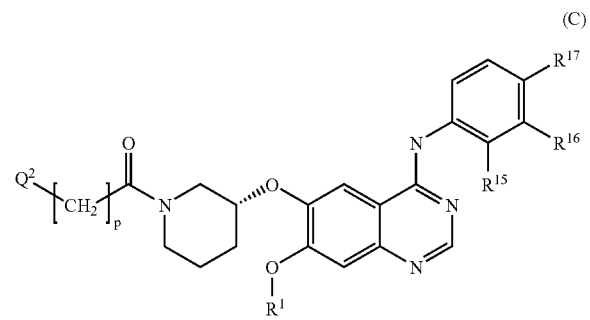

(C)

wherein
$R^{15}$, $R^{16}$, and $R^{17}$ are as hereinbefore defined;
$R^1$ is (1-4C)alkyl;
p is 0, 1 or 2; and
$Q^2$ is aryl or heteroaryl as hereinbefore defined, which may be optionally substituted as hereinbefore defined;
or a pharmaceutically acceptable salt thereof.

In the compounds of formula (C), or a pharmaceutically acceptable salt thereof, $R^1$, $R^{15}$, $R^{16}$, $R^{17}$, p and $Q^2$ may have any of the meanings hereinbefore defined, or as defined in any one of paragraphs (a) to (n) hereinafter:
(a) $R^1$ is methyl;
(b) $R^{15}$ is hydrogen, fluoro or chloro;
(c) $R^{15}$ is fluoro;
(d) $R^{16}$ is fluoro or chloro;
(e) $R^{16}$ is fluoro;
(f) $R^{17}$ is hydrogen, fluoro or chloro;
(g) $R^{17}$ is hydrogen;
(h) p is 0 or 1;
(i) p is 0;
(j) p is 1;
(k) $Q^2$ is an optionally substituted 5- or 6-membered or 9- or 10-membered heteraryl ring (as hereinbefore defined);
(l) $Q^2$ is a heteroaryl ring selected from the group consisting of isoxazolyl, furyl, thienyl, pyridyl, pyrazolyl, pyrrolyl, indolyl, quinolinyl, benzofuranyl, and benzothienyl, and wherein said ring may be optionally substituted by halogeno (particularly bromo, chloro or fluoro), amino, nitro, cyano, (1-4C)alkyl, [(1-4C)alkyl]amino, di-[(1-4C)alkyl]amino such as dimethylamino, N-[(1-4C)alkyl]carbamoyl and N,N-di[(1-4C)alkyl]carbamoyl such as N,N-dimethylcarbamoyl;
(m) $Q^2$ is phenyl optionally substituted by halogeno (particularly bromo, chloro or fluoro), amino, nitro, cyano, (1-4C)alkyl, [(1-4C)alkyl]amino, di-[(1-4C)alkyl]amino such as dimethylamino, N-[(1-4C)alkyl]carbamoyl and N,N-di[(1-4C)alkyl]carbamoyl such as N,N-dimethylcarbamoyl;
(n) $Q^2$ is phenyl.

In particular compounds of formula (C) above, $R^1$ is methyl, $R^{15}$ is fluoro, $R^{16}$ is chloro, $R^{17}$ is hydrogen, p is 0 or 1, and $Q^2$ is aryl or heteroaryl as hereinbefore defined or as defined in any one of paragraphs (k) to (n) above.

In a further preferred embodiment of the invention, the compounds have the general structural formula (D) shown below:

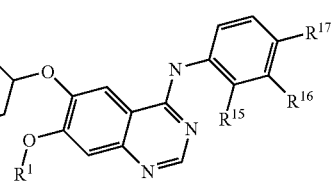

(D)

wherein
$R^{15}$, $R^{16}$, and $R^{17}$ are as hereinbefore defined;
$R^1$ is (1-4C)alkyl;
p is 0, 1 or 2; and
$Q^2$ is aryl or heteroaryl as hereinbefore defined, which may be optionally substituted as hereinbefore defined;
or a pharmaceutically acceptable salt thereof.

In the compounds of formula (D), or a pharmaceutically acceptable salt thereof, $R^1$, $R^{15}$, $R^{16}$, $R^{17}$, p and $Q^2$ may have any of the meanings hereinbefore defined, or as defined in any one of paragraphs (a) to (O) hereinafter:
(a) $R^1$ is methyl;
(b) $R^{15}$ is hydrogen, fluoro or chloro;
(c) $R^{15}$ is fluoro;
(d) $R^{16}$ is fluoro or chloro;
(e) $R^{16}$ is fluoro;
(f) $R^{17}$ is hydrogen, fluoro or chloro;
(g) $R^{17}$ is hydrogen;
(h) p is 0, 1 or 2;
(i) p is 0;
(j) p is 1;
(k) p is 2;
(l) $Q^2$ is an optionally substituted 5- or 6-membered or 9- or 10-membered heteraryl ring (as hereinbefore defined);
(m) $Q^2$ is a heteroaryl ring selected from the group consisting of isoxazolyl, furyl, thienyl, pyridyl, pyrazolyl, pyrrolyl, indolyl, quinolinyl, benzofuranyl, and benzothienyl, and wherein said ring may be optionally substituted by halogeno (particularly bromo, chloro or fluoro), amino, nitro, cyano, (1-4C)alkyl, [(1-4C)alkyl]amino, di-[(1-4C)alkyl]amino such as dimethylamino, N-[(1-4C)alkyl]carbamoyl and N,N-di[(1-4C)alkyl]carbamoyl such as N,N-dimethylcarbamoyl;
(n) $Q^2$ is phenyl optionally substituted by halogeno (particularly bromo, chloro or fluoro), amino, nitro, cyano, (1-4C)alkyl, [(1-4C)alkyl]amino, di-[(1-4C)alkyl]amino such as dimethylamino, N-[(1-4C)alkyl]carbamoyl and N,N-di[(1-4C)alkyl]carbamoyl such as N,N-dimethylcarbamoyl;
(o) $Q^2$ is phenyl.

In particular compounds of formula (D) above, $R^1$ is methyl, $R^{15}$ is fluoro, $R^{16}$ is chloro, $R^{17}$ is hydrogen, p is 0, 1 or 2, and $Q^2$ is aryl or heteroaryl as hereinbefore defined or as defined in any one of paragraphs (1) to (O) above.

Suitable values for any of the various groups within formula (I) as defined hereinbefore or hereafter in this specification include: — for halogeno fluoro, chloro, bromo and iodo;

for (1-6C)alkyl: methyl, ethyl, propyl, isopropyl, tert-butyl, pentyl and hexyl;

for (1-4C)alkyl: methyl, ethyl, propyl, isopropyl and tert-butyl;

for (1-6C)alkoxy: methoxy, ethoxy, propoxy, isopropoxy and butoxy;

for (2-8C)alkenyl: vinyl, isopropenyl, alkyl and but-2-enyl;

for (2-8C)alkynyl: ethynyl, 2-propynyl and but-2-ynyl;

for (2-6C)alkenyloxy: vinyloxy and allyloxy;

for (2-6C)alkynyloxy: ethynyloxy and 2-propynyloxy;

for (1-6C)alkylthio: methylthio, ethylthio and propylthio;

for (2-6C)alkenylthio: vinylthio and allylthio;

for (2-6C)alkynylthio: ethynylthio and 2-propynylthio for (1-6C)alkylsulfinyl: methylsulfinyl and ethylsulfinyl;

for (2-6C)alkenylsulfinyl: vinylsulfinyl and allylsulfinyl;

for (2-6C)alkynylsulfinyl: ethynylsulfinyl and 2-propynylsulfinyl for (1-6C)alkylsulfonyl: methylsulfonyl and ethylsulfonyl;

for (2-6C)alkenylsulfonyl: vinylsulfonyl and allylsulfonyl;

for (2-6C)alkynylsulfonyl: ethynylsulfonyl and 2-propynylsulfonyl;

for (1-6C)alkylamino: methylamino, ethylamino, propylamino, isopropylamino and butylamino;

for di-[(1-6C)alkyl]amino: dimethylamino, diethylamino, N-ethyl-N-methylamino and diisopropylamino;

for (1-6C)alkoxycarbonyl: methoxycarbonyl, ethoxycarbonyl, propoxycarbonyl and tert-butoxycarbonyl;

for N-(1-6C)alkylcarbamoyl: N-methylcarbamoyl, N-ethylcarbamoyl, N-propylcarbamoyl and N-isopropylcarbamoyl;

for N,N-di-[(1-6C)alkyl]carbamoyl: N,N-dimethylcarbamoyl, N-ethyl-N-methylcarbamoyl and N,N-diethylcarbamoyl;

for (2-6C)alkanoyl: acetyl, propionyl and isobutyryl;

for (2-6C)alkanoyloxy: acetoxy and propionyloxy;

for (2-6C)alkanoylamino: acetamido and propionamido;

for N-(1-6C)alkyl-(2-6C)alkanoylamino: N-methylacetamido and N-methylpropionamido;

for N-(1-6C)alkylsulfamoyl: N-methylsulfamoyl, N-ethylsulfamoyl and N-isopropylsulfamoyl;

for N,N-di-[(1-6C)alkyl]sulfamoyl: N,N-dimethylsulfamoyl and N-methyl-N-ethylsulfamoyl;

for (1-6C)alkanesulfonylamino: methanesulfonylamino and ethanesulfonylamino;

for N-(1-6C)alkyl-(1-6C)alkanesulfonylamino: N-methylmethanesulfonylamino and N-methylethanesulfonylamino;

or amino-(1-6C)alkyl: aminomethyl, 2-aminoethyl, 1-aminoethyl and 3-aminopropyl;

for (1-6C)alkylamino-(1-6C)alkyl: methylaminomethyl, ethylaminomethyl, 1-methylaminoethyl, 2-methylaminoethyl, 2-ethylaminoethyl and 3-methylaminopropyl;

for di-[(1-6C)alkyl]amino-(1-6C)alkyl: dimethylaminomethyl, diethylaminomethyl, 1-dimethylaminoethyl, 2-dimethylaminoethyl and 3-dimethylaminopropyl;

for halogeno-(1-6C)alkyl: chloromethyl, 2-chloroethyl, 1-chloroethyl and 3-chloropropyl;

for hydroxy-(1-6C)alkyl: hydroxymethyl, 2-hydroxyethyl, 1-hydroxyethyl and 3-hydroxypropyl;

for hydroxy-(1-6C)alkoxy: hydroxymethoxy, 2-hydroxyethoxy, 1-hydroxyethoxy and 3-hydroxypropoxy;

for (1-6C)alkoxy-(1-6C)alkyl: methoxymethyl, ethoxymethyl, 1-methoxyethyl, 2-methoxyethyl, 2-ethoxyethyl and 3-methoxypropyl;

for cyano-(1-6C)alkyl: cyanomethyl, 2-cyanoethyl, 1-cyanoethyl and 3-cyanopropyl;

for amino(2-6C)alkanoyl: aminoacetyl and 2-aminopropionyl;

for (1-6C)alkylamino-(2-6C)alkanoyl: methylaminoacetyl and 3-(methylamino)propionyl;

for N,N-di-[(1-6C)alkyl]amino-(2-6C)alkanoyl: di-methylaminoacetyl and 3-(di-methylamino)propionyl;

for (2-6C)alkanoylamino-(1-6C)alkyl: acetamidomethyl, propionamidomethyl and 2-acetamidoethyl;

for N-(1-6C)alkyl-(2-6C)alkanoylamino(1-6C)alkyl: N-methylacetamidomethyl, N-methylpropionamidomethyl, 2-(N-methylacetamido)ethyl and 2-(N-methylpropionamido)ethyl;

for (1-6C)alkoxycarbonylamino-(1-6C)alkyl: methoxycarbonylaminomethyl, ethoxycarbonylaminomethyl, tert-butoxycarbonylaminomethyl and 2-methoxycarbonylaminoethyl;

for carbamoyl(1-6C)alkyl: carbamoylmethyl, 1-carbamoylethyl, 2-carbamoylethyl and 3-carbamoylpropyl;

for N-(1-6C)alkylcarbamoyl(1-6C)alkyl: N-methylcarbamoylmethyl, N-ethylcarbamoylmethyl, N-propylcarbamoylmethyl, 1-(N-methylcarbamoyl)ethyl, 2-(N-methylcarbamoyl)ethyl and 3-(N-methylcarbamoyl)propyl;

for N,N di-(1-6C)alkylcarbamoyl(1-6C)alkyl: N,N-dimethylcarbamoylmethyl, N,N-diethylcarbamoylmethyl, N methyl, N-ethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl and 3-(N,N-dimethylcarbamoyl)propyl;

for sulfamoyl(1-6C)alkyl: sulfamoylmethyl, 1-sulfamoylethyl, 2-sulfamoylethyl and 3-sulfamoylpropyl;

for N-(1-6C)alkylsulfamoyl(1-6C)alkyl: N-methylsulfamoylmethyl, N-ethylsulfamoylmethyl, N-propylsulfamoylmethyl, 1-(N-methylsulfamoyl)ethyl, 2-(N-methylsulfamoyl)ethyl and 3-(N-methylsulfamoyl)propyl;

for N,Ndi-(1-6C)alkylsulfamoyl(1-6C)alkyl: N,N-dimethylsulfamoylmethyl, N,N-diethylsulfamoylmethyl, N methyl, N-ethylsulfamoylmethyl, 1-(N,N-dimethylsulfamoyl)ethyl, 1-(N,N-diethylsulfamoyl)ethyl, 2-(N,N-dimethylsulfamoyl)ethyl, 2-(N,N-diethylsulfamoyl)ethyl and 3-(N,N-dimethylsulfamoyl)propyl;

for (2-6C)alkanoyl(1-6C)alkyl: acetylmethyl, propionylmethyl, 2-acetylethyl and 2-propionylethyl;

for (2-6C)alkanoyloxy(1-6C)alkyl: acetoxymethyl, propionyloxymethyl, 2-acetoxyethyl and 3-acetoxypropyl;

for (1-6C)alkoxy(1-6C)alkylS(O)$_q$: 2-methoxyethylsulfonyl, 2-methoxyethylsulpinyl and 2-methoxyethylthio;

for amino(1-6C)alkylS(O)$_q$: 2-aminoethylsulfonyl, 2-aminoethylsulfinyl and 2-aminoethylthio;

for N-(1-6C)alkylamino(1-6C)alkylS(O)$_q$: 2-(methylamino)ethylsulfonyl, 2-(ethylamino)ethylsulfinyl and 2-(methylamino)ethylthio; and for N,N-di[(1-6C)alkyl]amino(1-6C)alkylS(O)$_q$: 2-(dimethylamino)ethylsulfonyl, 3-(dimethylamino)propylsulfonyl, 2-(di-ethylamino)ethylsulfinyl and 2-(N-methyl-N-ethylamino)ethylthio.

It is to be understood that when, R$^1$ is a group (1-6C)alkoxy substituted by, for example amino to give for example a 2-aminoethoxy group, it is the (1-6C)alkoxy group that is attached to the quinazoline ring. An analogous convention applies to the other groups defined herein.

When in this specification reference is made to a (1-4C) alkyl group it is to be understood that such groups refer to alkyl groups containing up to 4 carbon atoms. A skilled person will realise that representative examples of such groups are those listed above under (1-6C)alkyl that contain up to 4 carbon atoms, such as methyl, ethyl, propyl, isopropyl, butyl and tert-butyl. Similarly, reference to a (1-3C)alkyl group refers to alkyl groups containing up to 3 carbon atoms such as methyl, ethyl, propyl and isopropyl. A similar convention is adopted for the other groups listed above such as (1-4C) alkoxy, (2-4C)alkenyl, (2-4C)alkynyl and (2-4C)alkanoyl.

In the compound of Formula I hydrogen atoms are present at the 2, 5 and 8 positions on the quinazoline ring.

It is to be understood that, insofar as certain of the compounds of Formula I defined above may exist in optically active or racemic forms by virtue of one or more asymmetrically substituted carbon and/or sulfur atoms, and accordingly may exist in, and be isolated as enantiomerically pure, a mixture of diastereoisomers or as a racemate. The present invention includes in its definition any racemic, optically-active, enantiomerically pure, mixture of diastereoisomers, stereoisomeric form of the compound of Formula (I), or mixtures thereof, which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

The invention relates to all tautomeric forms of the compounds of the Formula I that possess antiproliferative activity.

It is also to be understood that certain compounds of the Formula I may exist in solvated as well as unsolvated forms such as, for example, hydrated forms. It is to be understood that the invention encompasses all such solvated forms which possess antiproliferative activity.

It is also to be understood that certain compounds of the Formula I may exhibit polymorphism, and that the invention encompasses all such forms which possess antiproliferative activity.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulfuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

A preferred compound of the invention is, for example, a quinazoline derivative of the Formula I selected from the compounds illustrated in Tables I to V below.

TABLE I

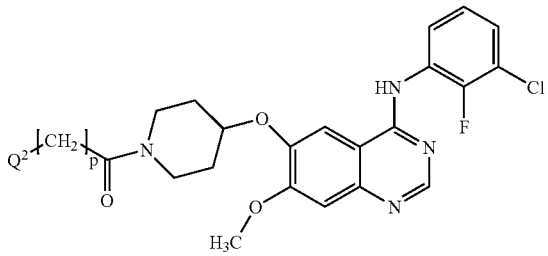

| Compound No. | Q$^2$ | p |
|---|---|---|
| 1 | (5-isoxazolyl) | 0 |
| 2 | (3-methyl-5-isoxazolyl) | 1 |
| 3 | (3-methyl-5-isoxazolyl) | 0 |
| 4 | (3-methyl-5-methyl-isoxazolyl) | 0 |
| 5 | (3-methyl-4-methyl-5-isoxazolyl) | 0 |
| 6 | (3-methyl-4-isoxazolyl) | 0 |
| 7 | (3-methyl-4-methyl-5-methylisoxazolyl) | 0 |
| 8 | (3-pyridyl) | 0 |
| 9 | (2-thienyl) | 1 |
| 10 | (2-pyridyl) | 0 |

TABLE I-continued

| Compound No. | Q² | p |
|---|---|---|
| 11 | 4-pyridyl | 0 |
| 12 | 2-amino-3-pyridyl | 0 |
| 13 | 2-furyl | 0 |
| 14 | 3-furyl | 0 |
| 15 | 5-bromo-2-methylfuran-yl | 0 |
| 16 | 3-thienyl | 0 |
| 17 | 3-amino-4-methyl-1H-pyrazol-yl | 0 |
| 18 | 2-quinolinyl | 0 |
| 19 | 2-benzofuranyl | 0 |
| 20 | 2-benzothienyl | 0 |
| 21 | 3-quinolinyl | 0 |
| 22 | 3-(1H-indolyl) | 0 |
| 23 | 3-thienyl | 1 |
| 24 | 5-bromo-2-thienyl | 0 |
| 25 | 2,6-dichloro-4-methylpyridin-yl | 0 |
| 26 | 5-methyl-2-thienyl | 0 |
| 27 | 1-methyl-2-pyrrolyl | 0 |
| 28 | 1-methyl-2-indolyl | 0 |
| 29 | 2-chloro-4-pyridyl | 0 |
| 30 | 1-methyl-4-nitro-pyrazol-yl | 1 |
| 31 | 3-nitro-5-methyl-1H-pyrazol-yl | 0 |

TABLE II
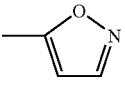
| Compound No. | Q² | p |
|---|---|---|
| 32 | 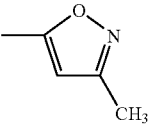 | 0 |
| 33 | 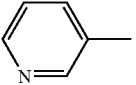 | 1 |
| 34 | 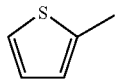 | 0 |
| 35 | 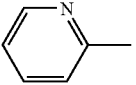 | 1 |
| 36 | 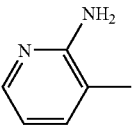 | 0 |
| 37 | 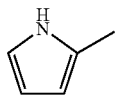 | 0 |
| 38 | 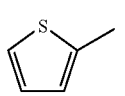 | 0 |
| 39 | 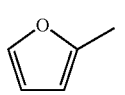 | 0 |
| 40 | 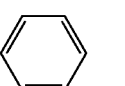 | 0 |
| 41 | 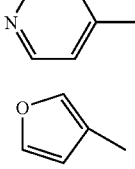 | 0 |
| 42 | 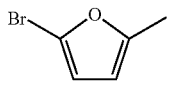 | 0 |
TABLE II-continued
| Compound No. | Q² | p |
|---|---|---|
| 43 | 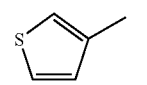 | 0 |
| 44 | 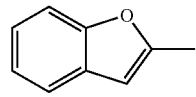 | 0 |
| 45 | 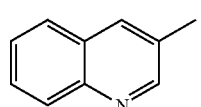 | 0 |
| 46 | 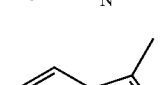 | 0 |
| 47 | 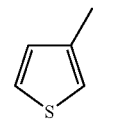 | 0 |
| 48 |  | 1 |
| 49 | 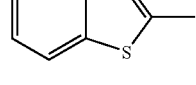 | 0 |
| 50 | 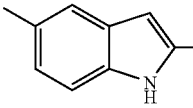 | 0 |
| 51 | 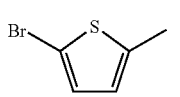 | 0 |
| 52 | | 0 |

TABLE II-continued

Structure: 4-[(3-chloro-2-fluorophenyl)amino]-6-methoxy-7-[(1-acyl-piperidin-4-yl)oxy]quinazoline with acyl = -C(=O)-(CH₂)ₚ-Q²

| Compound No. | Q² | p |
|---|---|---|
| 53 | 2,5-dimethylthiophen-3-yl (H₃C-thiophene-CH₃) | 0 |
| 54 | 1,2-dimethyl-1H-pyrrol-5-yl | 0 |
| 55 | 1,2-dimethyl-1H-indol-3-yl | 0 |
| 56 | 2-chloro-4-methylpyridin-5-yl | 0 |
| 57 | 1-methyl-4-nitro-1H-pyrazol-3-yl | 1 |
| 58 | 3-methyl-5-nitro-1H-pyrazol-4-yl | 0 |

TABLE III

Structure: 4-[(3-chloro-2-fluorophenyl)amino]-7-methoxy-6-[((3R)-1-acyl-piperidin-3-yl)oxy]quinazoline with acyl = -C(=O)-(CH₂)ₚ-Q²

| Compound No. | Q² | p |
|---|---|---|
| 59 | pyridin-3-yl | 0 |

TABLE III-continued

| Compound No. | Q² | p |
|---|---|---|
| 60 | thiophen-2-yl | 1 |
| 61 | pyridin-2-yl | 0 |
| 62 | pyridin-4-yl | 0 |
| 63 | 2-amino-pyridin-3-yl | 0 |
| 64 | 1H-pyrrol-2-yl | 0 |
| 65 | thiophen-2-yl | 0 |
| 66 | furan-2-yl | 0 |
| 67 | furan-3-yl | 0 |
| 68 | 5-bromo-furan-2-yl | 0 |
| 69 | thiophen-3-yl | 0 |
| 70 | benzofuran-2-yl | 0 |
| 71 | benzo[b]thiophen-2-yl | 0 |

TABLE III-continued
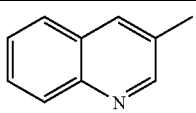
| Compound No. | Q² | p |
|---|---|---|
| 72 | 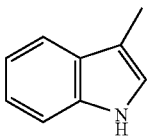 | 0 |
| 73 | 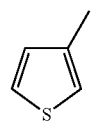 | 0 |
| 74 | 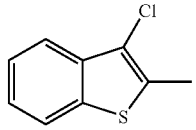 | 1 |
| 75 | 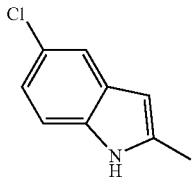 | 0 |
| 76 | 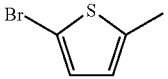 | 0 |
| 77 | 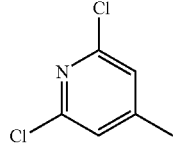 | 0 |
| 78 | 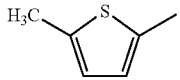 | 0 |
| 79 | 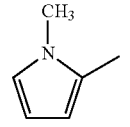 | 0 |
| 80 | 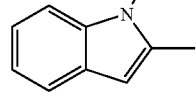 | 0 |
TABLE III-continued
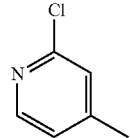
| Compound No. | Q² | p |
|---|---|---|
| 81 | 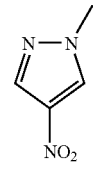 | 0 |
| 82 | 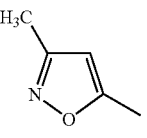 | 0 |
| 83 | 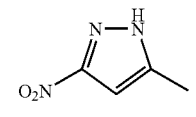 | 1 |
| 84 | 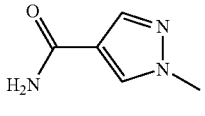 | 1 |
| 85 | 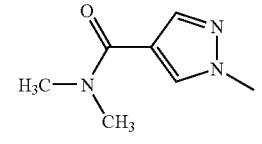 | 0 |
| 86 | 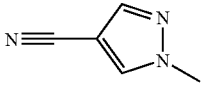 | 1 |
| 87 | | 1 |
| 88 | | 1 |

TABLE IV

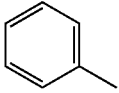

| Compound No. | Q² | p |
|---|---|---|
| 89 | (phenyl) | 0 |

TABLE V (same quinazoline core with urea linker)

| Compound No. | Q² | p |
|---|---|---|
| 90 | phenyl | 0 |
| 91 | phenyl | 1 |
| 92 | 4-(dimethylamino)phenyl | 0 |
| 93 | phenyl | 2 |
| 94 | 3,4-dimethoxyphenyl | 0 |
| 95 | 3-fluorophenyl | 0 |

TABLE V-continued

| Compound No. | Q² | p |
|---|---|---|
| 96 | 3,5-dimethylisoxazol-4-yl | 0 |
| 97 | thiophen-2-yl | 0 |
| 98 | thiophen-3-yl | 0 |

In a further aspect, the present invention provides a compound selected from one of the following:

(1) N-(3-chloro-2-fluorophenyl)-6-{[1-(isoxazol-5-ylcarbonyl)piperidin-4-yl]oxy}-7-methoxyquinazolin-4-amine;

(2) N-(3-chloro-2-fluorophenyl)-7-methoxy-6-({1-[(3-methylisoxazol-5-yl)acetyl]piperidin-4-yl}oxy)quinazolin-4-amine;

(3) N-(3-chloro-2-fluorophenyl)-7-methoxy-6-({1-[(3-methylisoxazol-5-yl)carbonyl]piperidin-4-yl}oxy)quinazolin-4-amine;

(4) N-(3-chloro-2-fluorophenyl)-7-methoxy-6-({1-[(5-methylisoxazol-3-yl)carbonyl]piperidin-4-yl}oxy)quinazolin-4-amine;

(5) N-(3-chloro-2-fluorophenyl)-7-methoxy-6-({1-[(5-methylisoxazol-4-yl)carbonyl]piperidin-4-yl}oxy)quinazolin-4-amine;

(6) N-(3-chloro-2-fluorophenyl)-7-methoxy-6-({1-[(3-methylisoxazol-4-yl)carbonyl]piperidin-4-yl}oxy)quinazolin-4-amine;

(7) N-(3-chloro-2-fluorophenyl)-6-({1-[(3,5-dimethylisoxazol-4-yl)carbonyl]piperidin-4-yl}oxy)-7-methoxyquinazolin-4-amine;

(8) N-(3-chloro-2-fluorophenyl)-7-methoxy-6-{[1-(pyridin-3-ylcarbonyl)piperidin-4-yl]oxy}quinazolin-4-amine;

(9) N-(3-chloro-2-fluorophenyl)-7-methoxy-6-{[1-(pyridin-2-ylcarbonyl)piperidin-4-yl]oxy}quinazolin-4-amine;

(10) N-(3-chloro-2-fluorophenyl)-6-{[1-(2-furoyl)piperidin-4-yl]oxy}-7-methoxyquinazolin-4-amine;

(11) N-(3-chloro-2-fluorophenyl)-7-{[1-(isoxazol-5-ylcarbonyl)piperidin-4-yl]oxy}-6-methoxyquinazolin-4-amine;

(12) N-(3-chloro-2-fluorophenyl)-6-methoxy-7-({1-[(3-methylisoxazol-5-yl)acetyl]piperidin-4-yl}oxy)quinazolin-4-amine;

(13) N-(3-chloro-2-fluorophenyl)-7-{[1-(pyridin-3-ylcarbonyl)piperidin-4-yl]oxy}-6-methoxyquinazolin-4-amine;

(14) N-(3-chloro-2-fluorophenyl)-7-{[1-(2-furoyl)piperidin-4-yl]oxy}-6-methoxyquinazolin-4-amine;

(15) N-(3-chloro-2-fluorophenyl)-7-methoxy-6-{[(3R)-1-(2-thienylacetyl)piperidin-3-yl]oxy}quinazolin-4-amine;
(16) N-(3-chloro-2-fluorophenyl)-6-{[(3R)-1-isonicotinoylpiperidin-3-yl]oxy}-7-methoxyquinazolin-4-amine;
(17) 6-({(3R)-1-[(2-aminopyridin-3-yl)carbonyl]piperidin-3-yl}oxy)-N-(3-chloro-2-fluorophenyl)-7-methoxyquinazolin-4-amine;
(18) N-(3-chloro-2-fluorophenyl)-7-methoxy-6-{[(3R)-1-(1H-pyrrol-2-ylcarbonyl)piperidin-3-yl]oxy}quinazolin-4-amine;
(19) N-(3-chloro-2-fluorophenyl)-7-methoxy-6-{[(3R)-1-(2-thienylcarbonyl)piperidin-3-yl]oxy}quinazolinamine;
(20) N-(3-chloro-2-fluorophenyl)-6-{[(3R)-1-(2-furoyl)piperidin-3-yl]oxy}-7-methoxyquinazolin-4-amine;
(21) N-(3-chloro-2-fluorophenyl)-6-{[(3R)-1-(3-furoyl)piperidin-3-yl]oxy}-7-methoxyquinazolin-4-amine;
(22) N-(3-chloro-2-fluorophenyl)-7-methoxy-6-{[(3R)-1-(3-thienylcarbonyl)piperidin-3-yl]oxy}quinazolin-4-amine;
(23) N-(3-chloro-2-fluorophenyl)-7-methoxy-6-{[(3R)-1-(3-thienylacetyl)piperidin-3-yl]oxy}quinazolin-4-amine;
(24) N-(3-chloro-2-fluorophenyl)-7-methoxy-6-({(3R)-1-[(1-methyl-1H-pyrrol-2-yl)carbonyl]piperidin-3-yl}oxy)quinazolin-4-amine;
(25) N-(3-chloro-2-fluorophenyl)-7-methoxy-6-({(3R)-1-[(4-nitro-1H-pyrazol-1-yl)acetyl]piperidin-3-yl}oxy)quinazolinamine;
(26) N-(3-chloro-2-fluorophenyl)-7-methoxy-6-({(3R)-1-[(3-methylisoxazol-5-yl)acetyl]piperidin-3-yl}oxy)quinazolin-4-amine;
(27) N-(3-chloro-2-fluorophenyl)-7-methoxy-6-{[(3R)-1-(4-{N,N-dimethylcarbamoyl}-1H-pyrazol-1-ylacetyl)piperidin-3-yl]oxy}quinazolin-4-amine;
(28) N-(3-chloro-2-fluorophenyl)-7-methoxy-6-{[(3R)-1-(4-cyano-1H-pyrazol-1-ylacetyl)piperidin-3-yl]oxy}quinazolin-4-amine;
(29) 4-({4-[(3-Chloro-2-fluorophenyl)amino]-7-methoxyquinazolin-6-yl}oxy)-N-phenylpiperidine-1-carboxamide;
(30) N-Benzyl-4-({4-[(3-chloro-2-fluorophenyl)amino]-7-methoxyquinazolin-6-yl}oxy)piperidine-1-carboxamide;
(31) 4-({4-[(3-Chloro-2-fluorophenyl)amino]-7-methoxyquinazolin-6-yl}oxy)-N-[4-(dimethylamino)phenyl]piperidine-1-carboxamide;
(32) 4-({4-[(3-Chloro-2-fluorophenyl)amino]-7-methoxyquinazolin-6-yl}oxy)-N-(2-phenylethyl)piperidine-1-carboxamide;
(33) 4-({4-[(3-Chloro-2-fluorophenyl)amino]-7-methoxyquinazolin-6-yl}oxy)-N-(3,4-dimethoxyphenyl)piperidine-1-carboxamide;
(34) 4-({4-[(3-Chloro-2-fluorophenyl)amino]-7-methoxyquinazolin-6-yl}oxy)-N-(3-fluorophenyl)piperidine-1-carboxamide;
(35) 4-({4-[(3-Chloro-2-fluorophenyl)amino]-7-methoxyquinazolin-6-yl}oxy)-N-(3,5-dimethylisoxazol-4-yl)piperidine-1-carboxamide;
(36) 4-({4-[(3-Chloro-2-fluorophenyl)amino]-7-methoxyquinazolin-6-yl}oxy)-N-2-thienylpiperidine-1-carboxamide;
(37) 4-({4-[(3-chloro-2-fluorophenyl)amino]-7-methoxyquinazolin-6-yl}oxy)-N-3-thienylpiperidine-1-carboxamide.

A further aspect the present invention provides a process for preparing a quinazoline derivative of Formula I or a pharmaceutically-acceptable salt thereof. It will be appreciated that during certain of the following processes certain substituents may require protection to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The protecting groups may be removed at any convenient stage in the synthesis using conventional techniques well known in the chemical art.

A quinazoline derivative of the Formula I, or a pharmaceutically-acceptable salt thereof, may be prepared by any process known to be applicable to the preparation of chemicallyrelated compounds. Such processes, when used to prepare a quinazoline derivative of the Formula I, or a pharmaceutically-acceptable salt thereof, are provided as a further feature of the invention and are illustrated by the following representative examples. Necessary starting materials may be obtained by standard procedures of organic chemistry (see, for example, Advanced Organic Chemistry (Wiley-Interscience), Jerry March). The preparation of such starting materials is described within the accompanying non-limiting Examples. Alternatively, necessary starting materials are obtainable by analogous procedures to those illustrated which are within the ordinary skill of an organic chemist. Information on the preparation of necessary starting materials or related compounds (which may be adapted to form necessary starting materials) may also be found in the following Patent and Application Publications, the contents of the relevant process sections of which are hereby incorporated herein by reference: WO94/27965, WO 95/03283, WO 96/33977, WO 96/33978, WO 96/33979, WO 96/33980, WO 96/33981, WO 97/30034, WO 97/38994, WO01/66099, U.S. Pat. No. 5,252,586, EP 520 722, EP 566 226, EP 602 851 and EP 635 507.

The present invention also provides that quinazoline derivatives of the Formula I, or pharmaceutically acceptable salts thereof, can be prepared by a process (a) to (i) as follows (wherein the variables are as defined above unless otherwise stated):

Process (a) By reacting a compound of the Formula II:

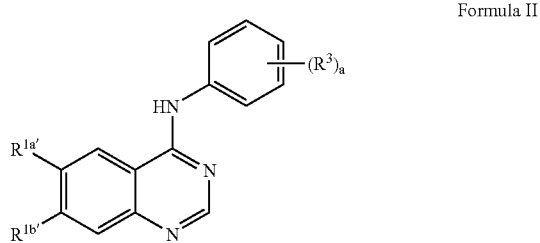

Formula II wherein $R^3$ and a are as defined in relation to formula (I), one of $R^{1a'}$ or $R^{1b'}$ is hydroxy and the other is a group $R^1$ as defined in relation to formula (I), except that any functional group is protected if necessary, with a compound of the Formula III:

$Q^2\text{-}X^1\text{—}Z\text{-}Q^1\text{-}X^2\text{-}Lg$      Formula III wherein $Q^1$, $Q^2$, Z, $X^2$ and $X^1$ have any of the meanings defined hereinbefore except that any functional group is protected if necessary and Lg is a displaceable group, wherein the reaction is conveniently performed in the presence of a suitable base, and whereafter any protecting group that is present is removed by conventional means.

A convenient displaceable group Lg is, for example, a halogeno, alkanesulfonyloxy or arylsulfonyloxy group, for example a chloro, bromo, methanesulfonyloxy, 4-nitrobenzenesulfonyloxy or toluenesulfonyloxy group (suitably a methanesulfonyloxy, 4-nitrobenzenesulfonyloxy or toluene-4-sulfonyloxy group).

The reaction is advantageously carried out in the presence of base. A suitable base is, for example, an organic amine base such as, for example, pyridine, 2,6-lutidine, collidine, 4-dimethylaminopyridine, triethylamine, N-methylmorpholine or diazabicyclo[5.4.0]undec-7-ene, or for example, an alkali metal or alkaline earth metal carbonate or hydroxide, for example sodium carbonate, potassium carbonate, cesium carbonate, calcium carbonate, sodium hydroxide or potassium hydroxide. Alternatively such a base is, for example, an alkali metal hydride, for example sodium hydride, an alkali metal or alkaline earth metal amide, for example sodium amide or sodium bis(trimethylsilyl)amide, or a sufficiently basic alkali metal halide, for example cesium fluoride or sodium iodide. The reaction is suitably effected in the presence of an inert solvent or diluent, for example an alkanol or ester such as methanol, ethanol, 2-propanol or ethyl acetate, a halogenated solvent such as methylene chloride, trichloromethane or carbon tetrachloride, an ether such as tetrahydrofuran or 1,4-dioxan, an aromatic hydrocarbon solvent such as toluene, or (suitably) a dipolar aprotic solvent such as N,N-dimethylformamide, N,N-dimethylacetamide, N-methylpyrrolidin-2-one or dimethylsulfoxide. The reaction is conveniently effected at a temperature in the range, for example, 10 to 150° C. (or the boiling point of the solvent), suitably in the range 20 to 90° C.

When $X^2$ is a direct bond a particularly suitable base is cesium fluoride. This reaction is suitably performed in an inert dipolar aprotic solvent such as N,N-dimethylacetamide or N,N-dimethylformamide. The reaction is suitably carried out at a temperature of from 25 to 85° C.

Process (b) By modifying a substituent in or introducing a substituent into another quinazoline derivative of Formula I or a pharmaceutically acceptable salt thereof, as hereinbefore defined except that any functional group is protected if necessary, and whereafter any protecting group that is present is removed by conventional means.

Methods for converting substituents into other substituents are known in the art. For example an alkylthio group may be oxidised to an alkylsulfinyl or alkylsulfonyl group, a carbamoyl group may be converted to cyano group (for example by reacting the carbamoyl substituent with trifluoroacetic anhydride in the presence of a suitable base, such as triethylamine), a cyano group reduced to an amino group, a nitro group reduced to an amino group, a hydroxy group alkylated to a methoxy group, a carbonyl group converted to a thiocarbonyl group (e.g. using Lawsson's reagent), a bromo group converted to an alkylthio group, an amino group may be acylated to give an alkanoylamino group (for example by reaction with a suitable acid chloride or acid anhydride) or an alkanoyloxy group may be hydrolysed to a hydroxy group (for example an acetyloxyacetyl group may be converted to a hydroxyacetyl group) Conveniently, one $R^1$ group may be converted into another $R^1$ group as a final step in the preparation of a compound of the Formula I. It is also possible to introduce a substituent onto the group $Q^1$ as a final step in the preparation of a compound of the Formula I. For example when the compound of Formula I contains primary or secondary amino group, for example an NH group in the ring $Q^1$, a substituent may be added to the nitrogen atom of the primary or secondary amino group by reacting the compound of the Formula I containing a primary or secondary amino group with a compound of the formula R-Lg, wherein Lg is a displaceable group (for example halogeno such as chloro or bromo) and R is the required substituent (for example (1-6C) alkyl, (2-6C)alkanoyl, cyano, cyano(1-6C)alkyl, (1-6C) alkylsulfonyl, carbamoyl, N-(1-6C)alkylcarbamoyl, N,N-di-[(1-6C)alkyl]carbamoyl, carbamoyl(1-6C)alkyl, N-(1-6C)alkylcarbamoyl(1-6C)alkyl, N,N-di-[(1-6C)alkyl]carbamoyl(1-6C)alkyl sulfamoyl, N-(1-6C)alkylsulfamoyl, N,N-di-[(1-6C)alkyl]sulfamoyl or a group $Q^2\text{-}X^3\text{—}$, wherein $Q^2\text{-}X^3\text{—}$ are as hereinbefore defined, which groups may be optionally substituted as hereinbefore defined). The reactions described above are conveniently performed in the presence of a suitable base (such as those described above in process (a), for example potassium carbonate, sodium iodide or di-isopropylethylamine) and conveniently in the presence of an inert solvent or diluent (for example the inert solvents and diluents described in process (a) such as N,N-dimethylacetamide, methanol, ethanol or methylene chloride). Conveniently, when $Q^1$ or $Q^2$ carries, for example an (2-6C)alkanoyl or (1-6C)alkylsulfonyl group, which is substituted by a group $NR^aR^b$, as hereinbefore defined, the $NR^aR^b$ group may be introduced by reaction of a compound of the Formula I wherein $Q^1$ or $Q^2$ carries a group of the formula Lg-(2-6C)alkanoyl or Lg-(1-6C)alkylsulfonyl, wherein Lg is a suitable displaceable group such as chloro, with a compound of the formula $NHR^aR^b$; wherein the reaction is conveniently performed in the presence of a suitable base and optionally in a suitable inert solvent or diluent. For example a pyrrolidin-1-ylacetyl group on $Q^1$ or $Q^2$ may be prepared by reacting a compound of the Formula I wherein $Q^1$ or $Q^2$ is substituted by a chloroacetyl group with pyrrolidine, analogous procedures may be used to prepare substituents on $Q^1$ or $Q^2$ such as morpholinoacetyl, N-methylaminoacetyl, N,N-dimethylaminoacetyl. Similarly, for example a 3-(N,N-dimethylamino)propylsulfonyl substituent on $Q^1$ or $Q^2$ may be prepared by reacting a compound of the Formula I wherein $Q^1$ or $Q^2$ carries a 3-chloropropylsulfonyl substituent with di-methylamine. Further examples of modifying or converting substituents into other substituents are well known to those skilled in the art and further methods are contained in the accompanying non-limiting Examples.

Process (c) By reacting a compound of the Formula II as hereinbefore defined with a compound of the Formula III as defined hereinbefore except Lg is OH under Mitsunobu conditions, and whereafter any protecting group that is present is removed by conventional means.

Suitable Mitsunobu conditions include, for example, reaction in the presence of a suitable tertiary phosphine and a di-alkylazodicarboxylate in an organic solvent such as THF, or suitably dichloromethane and in the temperature range 0° C.-60° C., but suitably at ambient temperature. A suitable tertiary phosphine includes for example tri-n-butylphosphine or suitably tri-phenylphosphine. A suitable di-alkylazodicarboxylate includes for example diethyl azodicarboxylate (DEAD) or suitably di-tert-butyl azodicarboxylate. Details of Mitsunobu reactions are contained in Tet. Letts., 31, 699, (1990); The Mitsunobu Reaction, D. L. Hughes, Organic Reactions, 1992, Vol. 42, 335-656 and Progress in the Mitsunobu Reaction, D. L. Hughes, Organic Preparations and Procedures International, 1996, Vol. 28, 127-164.

Process (d) For the preparation of those compounds of the Formula I wherein the group $R^1$ is a hydroxy group formed by the cleavage of a quinazoline derivative of the Formula I wherein $R^1$ is a (1-6C)alkoxy group.

The cleavage reaction may conveniently be carried out by any of the many procedures known for such a transformation. The cleavage reaction of a compound of the Formula I wherein $R^1$ is a (1-6C)alkoxy group may be carried out, for example, by treatment of the quinazoline derivative with an alkali metal (1-6C)alkylsulfide such as sodium ethanethiolate or, for example, by treatment with an alkali metal diarylphosphide such as lithium diphenylphosphide. Alternatively the cleavage reaction may conveniently be carried out, for example, by treatment of the quinazoline derivative with a boron or aluminium trihalide such as boron tribromide, or by reaction with an organic or inorganic acid, for example trifluoroacetic acid. Such reactions are suitably carried out in the presence of a suitable inert solvent or diluent as defined hereinbefore. A preferred cleavage reaction is the treatment of a quinazoline derivative of the Formula I with pyridine hydrochloride. The cleavage reactions are suitably carried out at a temperature in the range, for example, of from 10 to 150° C., for example from 25 to 80° C.

Process (e) For the preparation of those compounds of the Formula I wherein $R^1$ is a (1-6C)alkoxy, (2-6C)alkenyloxy, (2-6C)alkynyloxy, or a group of the formula:

$$Q^4\text{-}X^3\text{—}$$

wherein $X^3$ is 0 and $Q^4$ is as defined above, by the reaction of a compound of the Formula I wherein $R^1$ is OH, except that any functional group is protected if necessary, with a compound of the formula $R^{1'}$-Lg, wherein $R^{1'}$ is a (1-6C)alkyl, (2-6C)alkenyl, (2-6C)alkynyl, or a group $Q^4$ where $Q^4$ is as defined above, and Lg is a displaceable group, wherein the reaction is conveniently performed in the presence of a suitable base;

and whereafter any protecting group that is present is removed by conventional means. Suitable displaceable groups, Lg, are as hereinbefore defined for process a, for example chloro or bromo. The reaction is suitably performed in the presence of a suitable base. Suitable solvents, diluents and bases include, for example those hereinbefore described in relation to process (a).

Process (f) For the preparation of those compounds of the Formula I wherein $Q^1$, $Q^2$ or $R^1$ contains a (1-6C)alkoxy or substituted (1-6C)alkoxy group or a (1-6C)alkylamino or substituted (1-6C)alkylamino group, the alkylation, conveniently in the presence of a suitable base as defined hereinbefore for process a, of a quinazoline derivative of the Formula I wherein $Q^1$, $Q^2$ or $R^1$ contains a hydroxy group or a primary or secondary amino group as appropriate.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a (1-6C)alkyl chloride, bromide or iodide or a substituted (1-6C)alkyl chloride, bromide or iodide, conveniently in the presence of a suitable base as defined hereinbefore, in a suitable inert solvent or diluent as defined hereinbefore and at a temperature in the range, for example, 10 to 140° C., conveniently at or near ambient temperature. An analogous procedure may be used to introduce optionally substituted (2-6C)alkanoyloxy, (2-6C)alkanoyl amino and (1-6C)alkanesulfonylamino groups into $Q^1$, $Q^2$ or $R^1$.

Conveniently for the production of those compounds of the Formula I wherein $Q^1$, $Q^2$ or $R^1$ contains a (1-6C)alkylamino or substituted (1-6C)alkylamino group, a reductive animation reaction may be employed using formaldehyde or a (2-6C) alkanolaldehyde (for example acetaldehyde or propionaldehyde). For example, for the production of those compounds of the Formula I wherein $Q^1$, $Q^2$ or $R^1$ contains an N-methyl group, the corresponding compound containing a N—H group may be reacted with formaldehyde in the presence of a suitable reducing agent. A suitable reducing agent is, for example, a hydride reducing agent, for example formic acid, an alkali metal aluminium hydride such as lithium aluminium hydride, or, suitably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride and sodium cyanoborohydride. When the reducing agent is formic acid the reaction is conveniently carried out using an aqueous solution of the formic acid. The reaction is performed at a temperature in the range, for example, 10 to 100° C., such as 70 to 90° C. or, conveniently, at or near ambient temperature. Conveniently, when the reducing agent is formic acid, protecting groups such as tert-butoxycarbonyl on the NH group to be alkylated (for example present from the synthesis of the starting material) may be removed in-situ during the reaction.

Process (g) For the preparation of those compounds of the Formula I wherein $R^1$ is substituted by a group T, wherein T is selected from (1-6C)alkylamino, di-[(1-6C)alkyl]amino, (2-6C)alkanoylamino, (1-6C)alkylthio, (1-6C)alkylsulfinyl and (1-6C)alkylsulfonyl, the reaction of a compound which is of formula (I) except that the group $R^1$ is replaced with a group $R^{1''}$-Lg wherein Lg is a displaceable group (for example chloro or bromo), and $R^{1''}$ is a group $R^1$ except that it has Lg in place of the group T, and further that any functional group is protected if necessary, with a compound of the formula TH, wherein T is as defined above except that any functional group is protected if necessary;

and whereafter any protecting group that is present is removed by conventional means. The reaction is conveniently carried out in the presence of a suitable base. The reaction may conveniently be performed in a suitable inert solvent of diluent. Suitable bases, solvents and diluents are for example those described under process (a). The reaction is suitable performed at a temperature of for example, from 10 to 150° C., for example 30 to 60° C.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group.

Process (h) By reacting a compound of the formula VI:

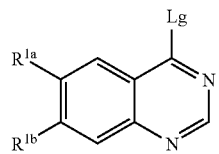

formula VI wherein $R^{1a}$ and $R^{1b}$ have any of the meanings defined hereinbefore except that any functional group is protected if necessary and Lg is a displaceable group as hereinbefore defined, with an aniline of the formula VII:

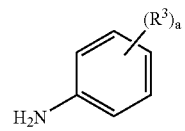

formula VII wherein $R^3$ and a have any of the meanings defined hereinbefore except that any functional group is protected if necessary, and wherein the reaction is conveniently performed in the presence of a suitable acid, and whereafter any protecting group that is present is removed by conventional means.

Suitable displaceable groups represented by Lg are as hereinbefore defined, in particular halogeno such as chloro.

The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxane, an aromatic solvent such as toluene, or a dipolar aprotic solvent such as $\underline{N},\underline{N}$-dimethylformamide, $\underline{N},\underline{N}$-dimethylacetamide, $\underline{N}$-methylpyrrolidin-2-one acetonitrile or dimethylsulfoxide. The reaction is conveniently carried out at a temperature in the range, for example, 10 to 250° C., conveniently in the range 40 to 120° C. or where a solvent or diluent is used at the reflux temperature. Conveniently, the compound of formula VI may be reacted with a compound of the formula VII in the presence of a protic solvent such as isopropanol, conveniently in the presence of an acid, for example hydrogen chloride gas in diethyl ether or dioxane, or hydrochloric acid, for example a 4M solution of hydrogen chloride in dioxane, under the conditions described above. Alternatively, this reaction may be conveniently carried out in an aprotic solvent, such as dioxane or a dipolar aprotic solvent such as $\underline{N},\underline{N}$-dimethylacetamide or acetonitrile in the presence of an acid, for example hydrogen chloride gas in diethyl ether or dioxane, or hydrochloric acid. The compound of the formula VI, wherein Lg is halogeno, may be reacted with a compound of the formula VII in the absence of an acid. In this reaction displacement of the halogeno leaving group Lg results in the formation of the acid HLg in-situ and autocatalysis of the reaction. Conveniently the reaction is carried out in a suitable inert organic solvent, for example isopropanol, dioxane or $\underline{N},\underline{N}$-dimethylacetamide. Suitable conditions for this reaction are as described above.

Alternatively, the compound of formula VI may be reacted with a compound of the formula VII in the presence of a suitable base. Suitable bases for this reaction are as hereinbefore defined under Process (a). This reaction is conveniently performed in an inert solvent or diluent, for example those mentioned above in relation to this process (i);

Process (i)

For the preparation of those compounds of the Formula I wherein $Q^1$ is a nitrogen containing heterocyclyl group linked to the —Z— group by a ring nitrogen, the coupling of a compound of the Formula I, as hereinbefore defined, except that the group of sub-formula (i) is a group of sub-formula (x) H-Q$^1$-X$^2$—O—, and any functional group is protected if necessary, with a compound of formula Q$^2$-X$^1$—Z-Lg, wherein Z, Q$^2$ and X$^1$ are as defined above and Lg is a leaving group as hereinbefore defined (such as —OH or halogeno such as chloro); and whereafter any protecting group that is present is removed by conventional means.

This reaction is particularly suitable when Z is C(O) and Lg is —OH, so the compound of formula Q$^2$-X$^1$—Z-Lg is a carboxylic acid of the formula Q$^2$-X$^1$—C(O)—OH.

The coupling reaction is conveniently carried out in the presence of a suitable coupling agent, such as a carbodiimide (for example 1-[3-(Dimethylamino)propyl]-3-ethylcarbodiimide), or a suitable peptide coupling agent, for example O-(7-azabenzotriazol-1-yl)-N,N,N',N'-tetramethyluronium hexafluoro-phosphate (HATU). The coupling reaction is conveniently carried out in an inert solvent such as, for example, a halogenated solvent such as methylene chloride, or a dipolar aprotic solvent such as N,N-dimethylformamide, N,N-dimethylacetamide, 1-methyl-2-pyrrolidinone. Suitably the coupling reaction is carried out in the presence of a suitable base, such as an organic amine, for example di-isopropylethylamine or 4-dimethylaminopyridine. The coupling reaction is suitably performed at −25° C. to 150° C., conveniently at ambient temperature.

This reaction is also particularly suitable when Z is —O—C(O)— and Lg is chloro, so the compound of formula Q$^2$-X$^1$—Z-Lg is a chloroformate of the formula Q$^2$-X$^1$—O—C(O)—Cl.

Process (j)

For the preparation of those compounds of the Formula I wherein Q$^1$ is a nitrogen containing heterocyclyl group linked to the —Z— group by a ring nitrogen, and Z is a group of formula —NR$^{10}$—C(O)— (where R$^{10}$ is preferably H); said process comprising the coupling of a compound of the Formula I, as hereinbefore defined, except that the group of sub-formula (i) is a group of sub-formula (x) H-Q$^1$-X$^2$—O—, and any functional group is protected if necessary, with a compound of formula Q$^2$-X$^1$—N=C=O, wherein Q$^2$ and X$^1$ are as defined above; and whereafter any protecting group that is present is removed by conventional means.

The coupling reaction is conveniently carried out in an inert solvent such as, for example, a halogenated solvent such as methylene chloride. The coupling reaction is suitably performed at −25° C. to 150° C., conveniently at ambient temperature.

Suitably, after any of these processes, any protecting groups are removed to produce a quinazoline derivative of Formula I, or a pharmaceutically acceptable salt thereof.

Suitable methods for removal of protecting groups are well known and are discussed herein. For example for the production of those compounds of the Formula I wherein R$^{1a}$ or R$^{1b}$ contains a primary or secondary amino group, the cleavage of the corresponding compound of Formula I wherein R$^{1a}$ or R$^{1b}$ contains a protected primary or secondary amino group.

Suitable protecting groups for an amino group are, for example, any of the protecting groups disclosed hereinbefore for an amino group. Suitable methods for the cleavage of such amino protecting groups are also disclosed hereinbefore. In particular, a suitable protecting group is a lower alkoxycarbonyl group such as a tert-butoxycarbonyl group which may be cleaved under conventional reaction conditions such as under acid-catalysed hydrolysis, for example in the presence of trifluoroacetic acid.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

When a pharmaceutically-acceptable salt of a quinazoline derivative of the Formula I is required, for example an acid-addition salt, it may be obtained by, for example, reaction of said quinazoline derivative with a suitable acid using a conventional procedure. To facilitate isolation of the compound during preparation, the compound may be prepared in the form of a salt that is not a pharmaceutically acceptable salt. The resulting salt can then be modified by conventional techniques to give a pharmaceutically acceptable salt of the compound. Such techniques include, for example ion exchange techniques or re-precipitation of the compound in the presence of a pharmaceutically acceptable counter ion. For example re-precipitation in the presence of a suitable acid such as HCl to give a hydrochloride acid addition salt.

As mentioned hereinbefore some of the compounds according to the present invention may contain one of more chiral centers and may therefore exist as stereoisomers (for example when Q$^1$ contains a pyrrolidin-3-yl group). Stereoisomers may be separated using conventional techniques, e.g. chromatography or fractional crystallisation. The enantiomers may be isolated by separation of a racemate for example by fractional crystallisation, resolution or HPLC. The diastereomers may be isolated by separation by virtue of the different physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent. Examples of suitable chiral synthesis and separation of isomers are described in the Examples. When a specific stereoisomer is isolated it is suitably isolated substantially free for other stereoisomers, for example containing less than 20%, particularly less than 10% and more particularly less than 5% by weight of other stereoisomers.

In the section above the expression "inert solvent" refers to a solvent which does not react with the starting materials, reagents, intermediates or products in a manner which adversely affects the yield of the desired product.

Preparation of Starting Materials

Compounds of Formula II are commercially available or may be prepared using conventional techniques or analogous processes to those described in the prior art. In particular those patents and applications listed hereinbefore, such as WO96/15118, WO 01/66099 and EP 566 226. For example, the compounds of Formula II may be prepared in accordance with Reaction Scheme 1:

Reaction Scheme 1

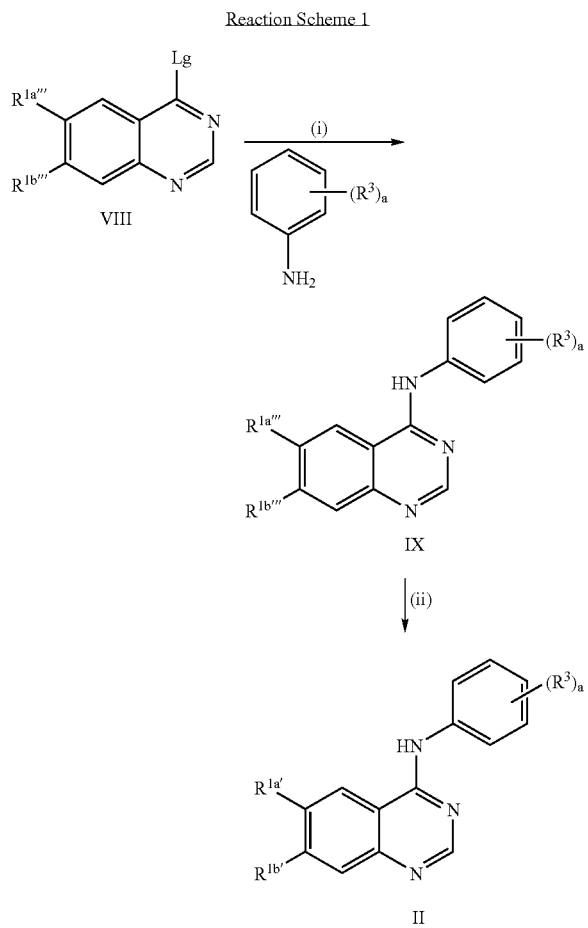

wherein $R^3$, and a are as hereinbefore defined, one of $R^{1a'''}$ or $R^{1b'''}$ is a group O-Pg where Pg is a hydroxy protecting group, and the other is a group $R^1$ is as defined herein before, except that any functional groups are protected if necessary, and $R^{1a'}$ and $R^{1b'}$ are as defined above in relation to formula (II), except that any functional groups are protected if necessary.

(i) Reaction is suitably carried out in an inert protic solvent (such as an alkanol for example iso-propanol), an aprotic solvent (such as dioxane) or a dipolar aprotic solvent (such as N,N-dimethylacetamide) in the presence of an acid, for example hydrogen chloride gas in diethyl ether or dioxane, or hydrochloric acid, under analogous conditions to those described above under process (i).

Alternatively the reaction may be carried out in one of the above inert solvents conveniently in the presence of a base, for example potassium carbonate. The above reactions are conveniently carried out at a temperature in the range, for example, 0 to 150° C., suitably at or near the reflux temperature of the reaction solvent.

(ii) Cleavage of Pg may be performed under standard conditions for such reactions. For example when Pg is an alkanoyl group such as acetyl, it may be cleaved by heating in the presence of a methanolic ammonia solution.

Compounds of formula VIII are known or can be prepared using known processes for the preparation of analogous compounds. If not commercially available, compounds of the formula (VII) may be prepared by procedures which are selected from standard chemical techniques, techniques which are analogous to the synthesis of known, structurally similar compounds, or techniques which are analogous to the procedures described in the Examples. For example, standard chemical techniques are as described in Houben Weyl. By way of example the compound of the formula VIII in which the group $R^{1b}$ is a group $R^1$, and this is methoxy, Lg is chloro and Pg is acetyl may be prepared using the process illustrated in Reaction Scheme 2:

Reaction Scheme 2

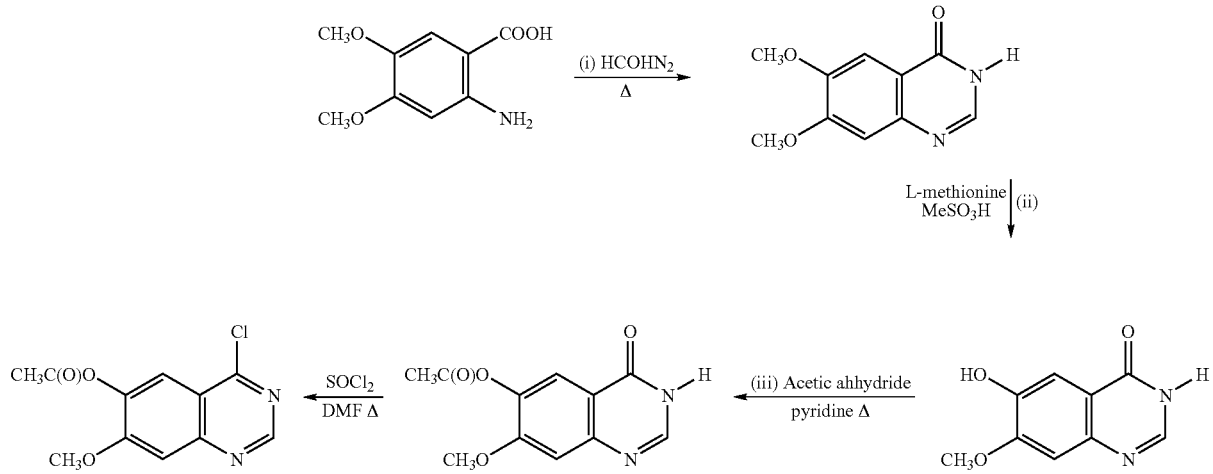

Reaction Scheme 2 may be generalised by the skilled man to apply to compounds within the present specification which are not specifically illustrated (for example to introduce a substituent other than methoxy at the 7-position in the quinazoline ring).

Compounds of the Formula III are commercially available or may be prepared using standard techniques.

Compounds of the Formula IV may be prepared using process (e) above, starting with a compound prepared, for example using Process (a).

Compounds of the formula V may be prepared using, for example process (a) or process (d) in which the group represented by $R^1$ is appropriately functionalised with a suitable displaceable group Lg such as chloro or bromo.

Compounds of the formula VI may be prepared using conventional methods well known in the art. For example the hydroxy protecting group, Pg, in a compound of the formula VII as hereinbefore described in Reaction Scheme 1 is removed to give the compound of the formula X:

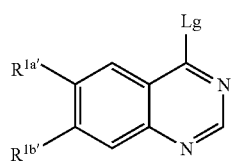

X wherein $R^{1a'}$ and $R^{1b'}$ are as defined above in relation to formula (II). The protecting group Pg may be removed from the compound of formula X using conventional techniques.

The compound of the formula X may then be coupled with a compound of the Formula III as hereinbefore defined using analogous conditions to those described in Process (a) or Process (d).

Certain novel intermediates utilised in the above processes are provided as a further feature of the present invention together with the process for their preparation. In particular, any intermediates which include a complete sub-group (i) are novel.

Biological Assays

The following assays may be used to measure the effects of the compounds of the present invention as inhibitors of the erb-tyrosine kinases, as inhibitors in-vitro of the proliferation of KB cells (human naso-pharangeal carcinoma cells) and as inhibitors in vivo on the growth in nude mice of xenografts of LoVo tumour cells (colorectal adenocarcinoma).

a) Protein Tyrosine Kinase Phosphorylation Assays

This test measures the ability of a test compound to inhibit the phosphorylation of a tyrosine containing polypeptide substrate by EGFR tyrosine kinase enzyme.

Recombinant intracellular fragments of EGFR, erbB2 and erbB4 (accession numbers X00588, X03363 and L07868 respectively) were cloned and expressed in the baculovirus/Sf21 system. Lysates were prepared from these cells by treatment with ice-cold lysis buffer (20 mM N-2-hydroxyethylpiperizine-N'-2-ethanesulfonic acid (HEPES) pH7.5, 150 mM NaCl, 10% glycerol, 1% Triton X-100, 1.5 mM $MgCl_2$, 1 mM ethylene glycol-bis(β-aminoethyl ether) N',N',N',N'-tetraacetic acid (EGTA), plus protease inhibitors and then cleared by centrifugation.

Constitutive kinase activity of the recombinant protein was determined by its ability to phosphorylate a synthetic peptide (made up of a random co-polymer of Glutamic Acid, Alanine and Tyrosine in the ratio of 6:3:1). Specifically, Maxisorb™ 96-well immunoplates were coated with synthetic peptide (0.2 μg of peptide in a 100 μl phosphate buffered saline (PBS) solution and incubated at 4° C. overnight). Plates were washed in PBS-T (phosphate buffered saline with 0.5% Tween 20) then in 50 mM HEPES pH 7.4 at room temperature to remove any excess unbound synthetic peptide. EGFR, ErbB2 or ErbB4 tyrosine kinase activity was assessed by incubation in peptide coated plates for 20 minutes at 22° C. in 100 mM HEPES pH 7.4, adenosine trisphosphate (ATP) at Km concentration for the respective enzyme, 10 mM $MnCl_2$, 0.1 mM $Na_3VO_4$, 0.2 mM DL-dithiothreitol (DTT), 0.1% Triton X-100 with test compound in DMSO (final concentration of 2.5%). Reactions were terminated by the removal of the liquid components of the assay followed by washing of the plates with PBS-T.

The immobilised phospho-peptide product of the reaction was detected by immunological methods. Firstly, plates were incubated for 90 minutes at room temperature with anti-phosphotyrosine primary antibodies that were raised in the mouse (4G10 from Upstate Biotechnology). Following extensive washing, plates were treated with Horseradish Peroxidase (BRP) conjugated sheep anti-mouse secondary antibody (NXA931 from Amersham) for 60 minutes at room temperature. After further washing, HRP activity in each well of the plate was measured colorimetrically using 22'-Azino-di-[3-ethylbenzthiazoline sulfonate (6)] diammonium salt crystals (ABTS™ from Roche) as a substrate.

Quantification of colour development and thus enzyme activity was achieved by the measurement of absorbance at 405 nm on a Molecular Devices ThermoMax microplate reader. Kinase inhibition for a given compound was expressed as an $IC_{50}$ value. This was determined by calculation of the concentration of compound that was required to give 50% inhibition of phosphorylation in this assay. The range of phosphorylation was calculated from the positive (vehicle plus ATP) and negative (vehicle minus ATP) control values.

b) EGFR Driven KB Cell Proliferation Assay

This assay measures the ability of a test compound to inhibit the proliferation of KB cells (human naso-pharangeal carcinoma obtained from the American Type Culture Collection (ATCC).

KB cells (human naso-pharangeal carcinoma obtained from the ATCC were cultured in Dulbecco's modified Eagle's medium (DMEM) containing 10% foetal calf serum, 2 mM glutamine and non-essential amino acids at 37° C. in a 7.5% $CO_2$ air incubator. Cells were harvested from the stock flasks using Trypsin/ethylaminediaminetetraacetic acid (EDTA). Cell density was measured using a haemocytometer and viability was calculated using trypan blue solution before being seeded at a density of $1.25 \times 10^3$ cells per well of a 96 well plate in DMEM containing 2.5% charcoal stripped serum, 1 mM glutamine and non-essential amino acids at 37° C. in 7.5% $CO_2$ and allowed to settle for 4 hours.

Following adhesion to the plate, the cells are treated with or without EGF (final concentration of 1 ng/ml) and with or without compound at a range of concentrations in dimethylsulfoxide (DMSO) (0.1% final) before incubation for 4 days. Following the incubation period, cell numbers were determined by addition of 50 μl of 3-(4,5-Dimethylthiazol-2-yl)-2,5-diphenyltetrazolium bromide (MTT) (stock 5 mg/ml) for 2 hours. MTT solution was then tipped off, the plate gently tapped dry and the cells dissolved upon the addition of 100 μl of DMSO.

Absorbance of the solubilised cells was read at 540 nm using a Molecular Devices ThermoMax microplate reader. Inhibition of proliferation was expressed as an $IC_{50}$ value. This was determined by calculation of the concentration of compound that was required to give 50% inhibition of proliferation. The range of proliferation was calculated from the positive (vehicle plus EGF) and negative (vehicle minus EGF) control values.

c) Clone 24 Phospho-erbB2 Cell Assay

This immunofluorescence end point assay measures the ability of a test compound to inhibit the phosphorylation of erbB2 in a MCF7 (breast carcinoma) derived cell line which was generated by transfecting MCF7 cells with the full length erbB2 gene using standard methods to give a cell line that overexpresses full length wild type erbB2 protein (hereinafter 'Clone 24' cells).

Clone 24 cells were cultured in Growth Medium (phenol red free Dulbecco's modified Eagle's medium (DMEM) containing 10% foetal bovine serum, 2 mM glutamine and 1.2 mg/ml G418) in a 7.5% $CO_2$ air incubator at 37° C. Cells were harvested from T75 stock flasks by washing once in PBS (phosphate buffered saline, pH7.4, Gibco No. 10010-015) and harvested using 2 mls of Trypsin (1.25 mg/ml)/ethylaminediaminetetraacetic acid (EDTA) (0.8 mg/ml) solution. The cells were resuspended in Growth Medium. Cell density was measured using a haemocytometer and viability was calculated using Trypan Blue solution before being further diluted in Growth Medium and seeded at a density of $1 \times 10^4$ cells per well (in 100 ul) into clear bottomed 96 well plates (Packard, No. 6005182).

3 days later, Growth Medium was removed from the wells and replaced with 100 ul Assay Medium (phenol red free DMEM, 2 mM glutamine, 1.2 mg/ml G418) either with or without erbB inhibitor compound. Plates were returned to the incubator for 4 hrs and then 20 µl of 20% formaldehyde solution in PBS was added to each well and the plate was left at room temperature for 30 minutes. This fixative solution was removed with a multichannel pipette, 100 µl of PBS was added to each well and then removed with a multichannel pipette and then 50 µl PBS was added to each well. Plates were then sealed and stored for up to 2 weeks at 4° C.

Immunostaining was performed at room temperature. Wells were washed once with 200 µl PBS/Tween 20 (made by adding 1 sachet of PBS/Tween dry powder (Sigma, No. P3563) to 1 L of double distilled $H_2O$) using a plate washer then 200 µl Blocking Solution (5% Marvel dried skimmed milk (Nestle) in PBS/Tween 20) was added and incubated for 10 minutes. Blocking Solution was removed using a plate washer and 200 µl of 0.5% Triton X-100/PBS was added to permeabalise the cells. After 10 minutes, the plate was washed with 200 µl PBS/Tween 20 and then 200 µl Blocking Solution was added once again and incubated for 15 minutes. Following removal of the Blocking Solution with a plate washer, 30 µl of rabbit polyclonal anti-phospho ErbB2 IgG antibody (epitope phospho-Tyr 1248, SantaCruz, No. SC-12352-R), diluted 1:250 in Blocking Solution, was added to each well and incubated for 2 hours. Then this primary antibody solution was removed from the wells using a plate washer followed by two 200 µl PBS/Tween 20 washes using a plate washer. Then 30 µl of Alexa-Fluor 488 goat anti-rabbit IgG secondary antibody (Molecular Probes, No. A-11008), diluted 1:750 in Blocking Solution, was added to each well. From now onwards, wherever possible, plates were protected from light exposure, at this stage by sealing with black backing tape. The plates were incubated for 45 minutes and then the secondary antibody solution was removed from the wells followed by two 200 ul PBS/Tween 20 washes using a plate washer. Then 100 µl PBS was added to each plate, incubated for 10 minutes and then removed using a plate washer. Then a further 100 µl PBS was added to each plate and then, without prolonged incubation, removed using a plate washer. Then 50 µl of PBS was added to each well and plates were resealed with black backing tape and stored for up to 2 days at 4° C. before analysis.

The Fluorescence signal is each well was measured using an Acumen Explorer Instrument (Acumen Bioscience Ltd.), a plate reader that can be used to rapidly quantitate features of images generated by laser-scanning. The instrument was set to measure the number of fluorescent objects above a pre-set threshold value and this provided a measure of the phosphorylation status of erbB2 protein. Fluorescence dose response data obtained with each compound was exported into a suitable software package (such as Origin) to perform curve fitting analysis. Inhibition of erbB2 phosphorylation was expressed as an $IC_{50}$ value. This was determined by calculation of the concentration of compound that was required to give 50% inhibition of erbB2 phosphorylation signal.

d) In Vivo Xenograft Assay

This assay measures the ability of a test compound to inhibit the growth of a LoVo tumour (colorectal adenocarcinoma obtained from the ATCC) in Female Swiss athymic mice (Alderley Park, nu/nu genotype).

Female Swiss athymic (nu/nu genotype) mice were bred and maintained in Alderley Park in negative pressure Isolators (PFI Systems Ltd.). Mice were housed in a barrier facility with 12 hr light/dark cycles and provided with sterilised food and water ad libitum. All procedures were performed on mice of at least 8 weeks of age. LoVo tumour cell (colorectal adenocarcinoma obtained from the ATCC) xenografts were established in the hind flank of donor mice by sub cutaneous injections of $1 \times 10^7$ freshly cultured cells in 100 µl of serum free media per animal. On day 5 post-implant, mice were randomised into groups of 7 prior to the treatment with compound or vehicle control that was administered once daily at 0.1 ml/10 g body weight. Tumour volume was assessed twice weekly by bilateral Vernier calliper measurement, using the formula (length×width)×√(length×width)×(π/6), where length was the longest diameter across the tumour, and width was the corresponding perpendicular. Growth inhibition from start of study was calculated by comparison of the mean changes in tumour volume for the control and treated groups, and statistical significance between the two groups was evaluated using a Students t test.

e) hERG-Encoded Potassium Channel Inhibition Assay

This assay determines the ability of a test compound to inhibit the tail current flowing through the human ether-a-go-go-related-gene (hERG)-encoded potassium channel.

Human embryonic kidney (HEK) cells expressing the hERG-encoded channel were grown in Minimum Essential Medium Eagle (EMEM; Sigma-Aldrich catalogue number M2279), supplemented with 10% Foetal Calf Serum (Labtech International; product number 4-101-500), 10% M1 serum-free supplement (Egg Technologies; product number 70916) and 0.4 mg/ml Geneticin G418 (Sigma-Aldrich; catalogue number G7034). One or two days before each experiment, the cells were detached from the tissue culture flasks with Accutase (TCS Biologicals) using standard tissue culture methods. They were then put onto glass coverslips resting in wells of a 12 well plate and covered with 2 ml of the growing media.

For each cell recorded, a glass coverslip containing the cells was placed at the bottom of a Perspex chamber containing bath solution (see below) at room temperature (~20° C.). This chamber was fixed to the stage of an inverted, phase-contrast microscope. Immediately after placing the coverslip in the chamber, bath solution was perfused into the chamber from a gravity-fed reservoir for 2 minutes at a rate of ~2 ml/min. After this time, perfusion was stopped.

A patch pipette made from borosilicate glass tubing (GC120F, Harvard Apparatus) using a P-97 micropipette puller (Sutter Instrument Co.) was filled with pipette solution (see hereinafter). The pipette was connected to the headstage of the patch clamp amplifier (Axopatch 200B, Axon Instruments) via a silver/silver chloride wire. The headstage ground was connected to the earth electrode. This consisted of a silver/silver chloride wire embedded in 3% agar made up with 0.85% sodium chloride.

The cell was recorded in the whole cell configuration of the patch clamp technique. Following "break-in", which was done at a holding potential of −80 mV (set by the amplifier), and appropriate adjustment of series resistance and capacitance controls, electrophysiology software (Clampax, Axon Instruments) was used to set a holding potential (−80 mV) and to deliver a voltage protocol. This protocol was applied every 15 seconds and consisted of a 1 s step to +40 mV followed by a 1 s step to −50 mV. The current response to each imposed voltage protocol was low pass filtered by the amplifier at 1 kHz. The filtered signal was then acquired, on line, by digitising this analogue signal from the amplifier with an analogue to digital converter. The digitised signal was then captured on a computer running Clampex software (Axon Instruments). During the holding potential and the step to +40 mV the current was sampled at 1 kHz. The sampling rate was then set to 5 kHz for the remainder of the voltage protocol.

The compositions, pH and osmolarity of the bath and pipette solution are tabulated below.

| Salt | Pipette (mM) | Bath (mM) |
|---|---|---|
| NaCl | — | 137 |
| KCl | 130 | 4 |
| $MgCl_2$ | 1 | 1 |
| $CaCl_2$ | — | 1.8 |
| HEPES | 10 | 10 |
| glucose | — | 10 |
| $Na_2ATP$ | 5 | — |
| EGTA | 5 | — |

| Parameter | Pipette | Bath |
|---|---|---|
| pH | 7.18-7.22 | 7.40 |
| pH adjustment with | 1M KOH | 1M NaOH |
| Osmolarity (mOsm) | 275-285 | 285-295 |

The amplitude of the hERG-encoded potassium channel tail current following the step from +40 mV to −50 mV was recorded on-line by Clampex software (Axon Instruments). Following stabilisation of the tail current amplitude, bath solution containing the vehicle for the test substance was applied to the cell. Providing the vehicle application had no significant effect on tail current amplitude, a cumulative concentration effect curve to the compound was then constructed.

The effect of each concentration of test compound was quantified by expressing the tail current amplitude in the presence of a given concentration of test compound as a percentage of that in the presence of vehicle.

Test compound potency ($IC_{50}$) was determined by fitting the percentage inhibition values making up the concentration-effect to a four parameter Hill equation using a standard data-fitting package. If the level of inhibition seen at the highest test concentration did not exceed 50%, no potency value was produced and a percentage inhibition value at that concentration was quoted.

Although the pharmacological properties of the compounds of the Formula I vary with structural change as expected, in general activity possessed by compounds of the Formula I, may be demonstrated at the following concentrations or doses in one or more of the above tests (a), (b) and (c):—

Test (a): —$IC_{50}$ in the range, for example, 0.001-10 μM;
Test (b): —$IC_{50}$ in the range, for example, 0.001-10 μM;
Test (c): —$IC_{50}$ in the range, for example, 0.01-10 μM;
Test (d): —activity in the range, for example, 1-200 mg/kg/day;

By way of example, using Test (a) (for the inhibition of tyrosine kinase protein phosphorylation) and Test (b) described above, representative compounds described in the Examples herein gave the $IC_{50}$ results shown below in Table VI.

TABLE VI

| Example | Compound Number | $IC_{50}$ (nM) Test (a) (inhibition of tyrosine kinase protein phosphorylation) | $IC_{50}$ (nM) Test (b) (EGFR driven KB cell proliferation assay) |
|---|---|---|---|
| 1 | 1 (Table 1) | <1 | 17 |
| 10 | 10 (Table 1) | 14 | 16 |
| 33 | 33 (Table 2) | 15 | 47 |
| 34 | 34 (Table 2) | 43 | 87 |
| 60 | 60 (Table 3) | <1 | 30 |
| 96 | 96 (Table 5) | <1 | 17 |

According to a further aspect of the invention there is provided a pharmaceutical composition which comprises a quinazoline derivative of the Formula I, or a pharmaceutically-acceptable thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixrs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

We have found that the compounds of the present invention possess anti-proliferative properties such as anti-cancer properties that are believed to arise from their erbB family receptor tyrosine kinase inhibitory activity, particularly inhibition of the EGF receptor (erbB1) tyrosine kinase. Furthermore, certain of the compounds according to the present invention possess substantially better potency against the EGF receptor tyrosine kinase, than against other tyrosine kinase enzymes, for example erbB2. Such compounds possess sufficient potency against the EGF receptor tyrosine kinase that they may be used in an amount sufficient to inhibit EGF receptor tyrosine kinase whilst demonstrating little, or significantly lower, activity against other tyrosine kinase enzymes such as erbB2. Such compounds are likely to be useful for the selective inhibition of EGF receptor tyrosine kinase and are likely to be useful for the effective treatment of, for example EGF driven tumours.

Accordingly, the compounds of the present invention are expected to be useful in the treatment of diseases or medical conditions mediated alone or in part by erbB receptor tyrosine kinases (especially EGF receptor tyrosine kinase), i.e. the compounds may be used to produce an erbB receptor tyrosine kinase inhibitory effect in a warm-blooded animal in need of such treatment. Thus the compounds of the present invention provide a method for the treatment of malignant cells characterised by inhibition of one or more of the erbB family of receptor tyrosine kinases. Particularly the compounds of the invention may be used to produce an anti-proliferative and/or pro-apoptotic and/or anti-invasive effect mediated alone or in part by the inhibition of erbB receptor tyrosine kinases. Particularly, the compounds of the present invention are expected to be useful in the prevention or treatment of those tumours that are sensitive to inhibition of one or more of the erbB receptor tyrosine kinases, such as EGF and/or erbB2 and/or erbB4 receptor tyrosine kinases (especially EGF receptor tyrosine kinase) that are involved in the signal transduction steps which drive proliferation and survival of these tumour cells. Accordingly the compounds of the present invention are expected to be useful in the treatment of psoriasis, benign prostatic hyperplasia (BPH), atherosclerosis and restenosis and/or cancer by providing an anti-proliferative effect, particularly in the treatment of erbB receptor tyrosine kinase sensitive cancers. Such benign or malignant tumours may affect any tissue and include non-solid tumours such as leukaemia, multiple myeloma or lymphoma, and also solid tumours, for example bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancers.

According to this aspect of the invention there is provided a compound of the Formula I, or a pharmaceutically acceptable salt thereof, for use as a medicament.

According to a further aspect of the invention there is provided a compound of the Formula I, or a pharmaceutically acceptable salt thereof, for use in the production of an anti-proliferative effect in a warm-blooded animal such as man.

Thus according to this aspect of the invention there is provided the use of a quinazoline derivative of the Formula I, or a pharmaceutically-acceptable salt thereof, as defined hereinbefore in the manufacture of a medicament for use in the production of an anti-proliferative effect in a warm-blooded animal such as man.

According to a further feature of this aspect of the invention there is provided a method for producing an anti-proliferative effect in a warm-blooded animal, such as man, in need of such treatment which comprises administering to said animal an effective amount of a quinazoline derivative of the Formula I, or a pharmaceutically acceptable salt thereof, as hereinbefore defined.

According to a further aspect of the invention there is provided the use of a quinazoline derivative of the Formula I, or a pharmaceutically-acceptable salt thereof, as defined hereinbefore in the manufacture of a medicament for use in the prevention or treatment of those tumours which are sensitive to inhibition of erbB receptor tyrosine kinases, such as EGFR and/or erbB2 and/or erbB4 (especially EGFR), that are involved in the signal transduction steps which lead to the proliferation of tumour cells.

According to a further feature of this aspect of the invention there is provided a method for the prevention or treatment of those tumours which are sensitive to inhibition of one or more of the erbB family of receptor tyrosine kinases, such as EGFR and/or erbB2 and/or erbB4 (especially EGFR), that are involved in the signal transduction steps which lead to the proliferation and/or survival of tumour cells which comprises administering to said animal an effective amount of a quinazoline derivative of the Formula I, or a pharmaceutically-acceptable salt thereof, as defined hereinbefore.

According to a further feature of this aspect of the invention there is provided a compound of the Formula I, or a pharmaceutically acceptable salt thereof, for use in the prevention or treatment of those tumours which are sensitive to inhibition of erbB receptor tyrosine kinases, such as EGFR and/or erbB2 and/or erbB4 (especially EGFR), that are involved in the signal transduction steps which lead to the proliferation of tumour cells.

According to a further aspect of the invention there is provided the use of a quinazoline derivative of the Formula I, or a pharmaceutically-acceptable salt thereof, as defined hereinbefore in the manufacture of a medicament for use in providing a EGFR and/or erbB2 and/or erbB4 (especially an EGFR) tyrosine kinase inhibitory effect.

According to a further feature of this aspect of the invention there is provided a method for providing a EGFR and/or an erbB2 and or an erbB4 (especially an EGFR) tyrosine kinase inhibitory effect which comprises administering to said animal an effective amount of a quinazoline derivative of the Formula I, or a pharmaceutically-acceptable salt thereof, as defined hereinbefore.

According to a further feature of this aspect of the invention there is provided a compound of the Formula I, or a pharmaceutically acceptable salt thereof, for use in providing a EGFR and/or erbB2 and/or erbB4 (especially an EGFR) tyrosine kinase inhibitory effect.

According to a further feature of the present invention there is provided the use of a quinazoline derivative of the Formula I, or a pharmaceutically-acceptable salt thereof, as defined hereinbefore in the manufacture of a medicament for use in providing a selective EFGR tyrosine kinase inhibitory effect.

According to a further feature of this aspect of the invention there is provided a method for providing a selective EGFR tyrosine kinase inhibitory effect which comprises administering to said animal an effective amount of a quinazoline derivative of the Formula I, or a pharmaceutically-acceptable salt thereof, as defined hereinbefore.

According to a further feature of this aspect of the invention there is provided a compound of the Formula I, or a pharmaceutically acceptable salt thereof, for use in providing a selective EGFR kinase inhibitory effect.

By "a selective EGFR kinase inhibitory effect" is meant that the quinazoline derivative of Formula I is more potent against EGFR tyrosine kinase than it is against other kinases. In particular some of the compounds according to the invention are more potent against EGFR receptor tyrosine kinase than it is against other tyrosine kinases such as other erb-B receptor tyrosine kinases, particularly erbB2 receptor tyrosine kinase. For example a selective EGFR kinase inhibitor according to the invention is at least 5 times, preferably at least 10 times more potent against EGFR tyrosine kinase than it is against erbB2 receptor tyrosine kinase, as determined from the relative $IC_{50}$ values in suitable assays (for example the by comparing the $IC_{50}$ value from the Clone 24 phospho-erbB2 cell assay (a measure of the erb-B2 tyrosine kinase inhibitory activity in cells) with the $IC_{50}$ from the KB cell assay (a measure of the EGFR tyrosine kinase inhibitory activity in cells) for a given test compound as described above).

According to a further aspect of the present invention there is provided the use of a quinazoline derivative of the Formula I, or a pharmaceutically-acceptable salt thereof, as defined hereinbefore in the manufacture of a medicament for use in the treatment of a cancer (for example a cancer selected from leukaemia, multiple myeloma, lymphoma, bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancer).

According to a further feature of this aspect of the invention there is provided a method for treating a cancer (for example a cancer selected from leukaemia, multiple myeloma, lymphoma, bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancer) in a warm-blooded animal, such as man, in need of such treatment, which comprises administering to said animal an effective amount of a quinazoline derivative of the Formula I, or a pharmaceutically-acceptable salt thereof, as defined hereinbefore.

According to a further aspect of the invention there is provided a compound of the Formula I, or a pharmaceutically acceptable salt thereof, for use in the treatment of a cancer (for example selected from leukaemia, multiple myeloma, lymphoma, bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancer).

As mentioned above the size of the dose required for the therapeutic or prophylactic treatment of a particular disease will necessarily be varied depending upon, amongst other things, the host treated, the route of administration and the severity of the illness being treated.

The anti-proliferative treatment defined hereinbefore may be applied as a sole therapy or may involve, in addition to the quinazoline derivative of the invention, conventional surgery or radiotherapy or chemotherapy. Such chemotherapy may include one or more of the following categories of anti-tumour agents: —

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5c-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example other inhibitors of the epidermal growth factor family (for example EGFR family tyrosine kinase inhibitors such as N-(3-chloro-4-fluorophenyl)-7-methoxy-6-(3- morpholinopropoxy)quinazolinfamine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy) quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a quinazoline derivative of the Formula I as defined hereinbefore and an additional anti-tumour agent as defined hereinbefore for the conjoint treatment of cancer.

Although the compounds of the Formula I are primarily of value as therapeutic agents for use in warm-blooded animals (including man), they are also useful whenever it is required to inhibit the effects of the erbB receptor tyrosine protein kinases. Thus, they are useful as pharmacological standards for use in the development of new biological tests and in the search for new pharmacological agents.

The invention will now be illustrated by the following non limiting examples in which, unless stated otherwise:

(i) temperatures are given in degrees Celsius (° C.); operations were carried out at room or ambient temperature, that is, at a temperature in the range of 18-25° C.;

(ii) organic solutions were dried over anhydrous magnesium sulfate; evaporation of solvent was carried out using a rotary evaporator under reduced pressure (6004000 Pascals; 4.5-30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC and/or analytical LCMS, and reaction times are given for illustration only;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm) relative to tetramethylsilane (TMS) as an internal standard, determined at 300 or 400 MHz using perdeuterio dimethyl sulfoxide (DMSO-$d_6$) as solvent unless otherwise indicated; the following abbreviations have been used: s, singlet; d, doublet; t, triplet; q, quartet; m, multiplet; b, broad;

(viii) chemical symbols have their usual meanings; SI units and symbols are used;

(ix) solvent ratios are given in volume:volume (v/v) terms; and (x) mass spectra (MS) were run with an electron energy of 70 electron volts in the chemical ionization (CI) mode using a direct exposure probe and ionization was effected by electrospray; values for m/z are given; generally, only ions which indicate the parent mass are reported; and unless otherwise stated, the mass ion quoted is $(MH)^+$; alternatively, mass spectra (MS) were run using a Waters or Micromass electrospray LC-MS (where stated) in positive or negative ion mode; values for m/z are again given; generally, only ions which indicate the parent mass are reported; and unless otherwise stated, the mass ion quoted is again $(MH)^+$;

(xi) unless stated otherwise compounds containing an asymmetrically substituted carbon and/or sulfur atom have not been resolved;

(xii) where a synthesis is described as being analogous to that described in a previous example the amounts used are the millimolar ratio equivalents to those used in the previous example;

(xvi) the following abbreviations have been used:

| | |
|---|---|
| DMSO | dimethylsulphoxide; |
| THF | Tetrahydrofuran; |
| HATU | O-(7-azabenzotriazol-1-y1)-N,N,N',N'-tetramethyluroniumhexafluorophosphate |
| DIPEA | di-isopropylethylamine |
| DMA | N,N-dimethylacetamide |
| DCM | dichloromethane |
| MeOH | methanol |
| AcOH | acetic acid |
| TBTU | O-(1H-Benzotriazol-1-yl)-N,N,N',N'-tetramethyluronium hexaflurophosphate |
| EDCI | 1-(3-Dimethylaminopropyl)-3-ethylcarbodiimide |
| LCMS | liquid chromatography mass spectrometer | xvii) where a synthesis is described as leading to an acid addition salt (e.g. HCl salt), the specific stoichiometry of the salt was not confirmed.

EXAMPLE 1

Preparation of Compound No 1 in Table 1

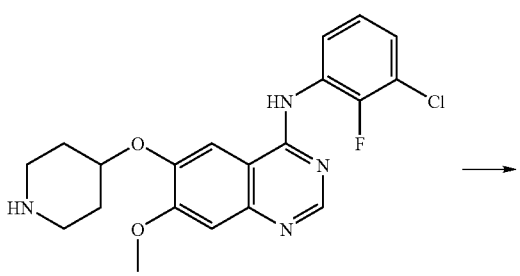

-continued

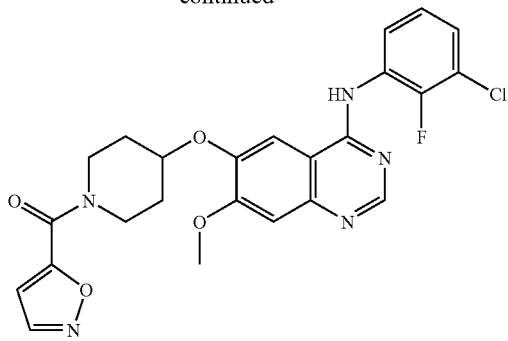

HATU (0.31 g) was added to a solution of N-(3-chloro-2-fluorophenyl)-7-methoxy-6-(piperidin-4-yloxy)quinazolin-4-amine dihydrochloride (300 mg), diisopropylethylamine (0.45 ml) and isoxazole-5-carboxylic acid (0.1 g) in methylene chloride (9 ml). The resulting mixture was stirred at room temperature for 2.5 hrs. Methylene chloride (20 ml) was added and the organics washed with aqueous sodium hydroxide (2M, 30 ml) and water (30 ml). The crudes were then purified by flash column chromatography eluting with methanol/methylene chloride (2.5/97.5). Fractions containing the desired product were evaporated to a white foam which was triturated with diethyl ether (20 ml) to give N-(3-chloro-2-fluorophenyl)-6-{[1-(isoxazol-5-ylcarbonyl)piperidin-4-yl]oxy}-7-methoxyquinazolin-4-amine as a white solid (0.110 g). $^1$H NMR Spectrum: (DMSO $d_6$ 373K) 1.88 (m, 2H), 2.09 (m, 2H), 3.61 (m, 2H), 3.84 (m, 2H), 3.96 (s, 3H), 4.78 (m, 1H), 6.87 (s, 1H), 7.29 (m, 1H), 7.29 (s, 1H), 7.42 (m, 1H), 7.59 (m, 1H), 7.93 (s, 1H), 8.39 (s, 1H), 8.64 (s, 1H), 9.28 (br s, 1H); Mass Spectrum: (M+H)$^+$ 498.

Preparation of Starting Material

The 6-(piperidin-4-yloxy)-4-(3-chloro-2-fluoroanilino)-7-methoxyquinazoline dihydrochloride starting material was prepared as follows:

6-Acetoxy-4-chloro-7-methoxyquinazoline, (Example 25-5 of in WO01/66099; 10.0 g, 39.6 mmole) was added in portions to a stirred 7N methanolic ammonia solution (220 ml) cooled to 10° C. in an ice/water bath. After stirring for one hour the precipitate was filtered, washed with diethylether and dried thoroughly under high vacuum to give 4-chloro-6-hydroxy-7-methoxyquinazoline (5.65 g, 67.8%); $^1$H NMR Spectrum: (DMSO ds) 3.96 (s, 3H); 7.25 (s, 1H); 7.31 (s, 1H); 8.68 (s, 1H); Mass Spectrum: (M+H)$^+$ 211

Di-tert-butylazodicarboxylate (9.22 g) in methylene chloride (20 ml) was added slowly to a stirred suspension of 4-chloro-6-hydroxy-7-methoxyquinazoline (5.63 g), 4-hydroxy-1-tert-butoxycarbonylpiperidine (8.06 g) and triphenylphosphine (10.5 g) in methylene chloride (100 ml) at 5° C. under an atmosphere of nitrogen. The reaction mixture was allowed to warm to room temperature for 16 hours. The reaction mixture was then evaporated under vacuum and adsorbed onto silica and the product was eluted with isohexane/ethyl acetate/triethylamine (75/24/1 followed by 70/29/1). The fractions containing the desired product were combined and evaporated under vacuum to give tert-butyl 4-[(4-chloro-7-methoxyquinazolin-6-yl)oxy]piperidine-1-carboxylate as a white solid (10.3 g); $^1$H NMR Spectrum: (DMSO $d_6$) 1.40 (s, 9H), 1.56-1.69 (m, 2H), 1.93-2.04 (m, 2H), 3.20-3.31 (m, 2H), 3.60-3.70 (m, 2H), 4.00 (s, 3H), 4.89 (m, 1H), 7.45 (s, 1H), 7.50 (s, 1H), 8.86 (s, 1H); Mass Spectrum: (M+H)$^+$ 394.

4.0M HCl in Dioxane (4.0 ml) was added to a suspension of tert-butyl 4-[(4-chloro-7-methoxyquinazolin-6-yl)oxy]piperidine-1-carboxylate (2.62 g) and 3-chloro-2-fluoroaniline (1.08 g) in iso-propanol (50 ml). The reaction mixture was stirred and heated at 100° C. for 2 hours. The yellow precipitate was filtered hot and washed with iso-propanol followed by diethylether and dried under vacuum to give 6-(piperidin-4-yloxy)-4-(3-chloro-2-fluoroanilino)-7-methoxyquinazoline as a di-hydrochloride salt (2.38 g); $^1$H NMR Spectrum: (DMSO $d_6$) 1.84-1.99 (m, 2H), 2.22-2.33 (m, 2H), 3.12-3.33 (m, 4H), 4.00 (s, 3H), 5.08 (m, 1H), 7.34 (t, 1H), 7.40 (s, 1H), 7.50 (t, 1H), 7.62 (t, 1H), 8.80 (s, 1H), 8.84-8.94 (m, 2H), 8.99-9.11 (m, 1H); Mass Spectrum: (M+H)$^+$ 403.

EXAMPLE 2

Preparation of Compound No 3 in Table 1

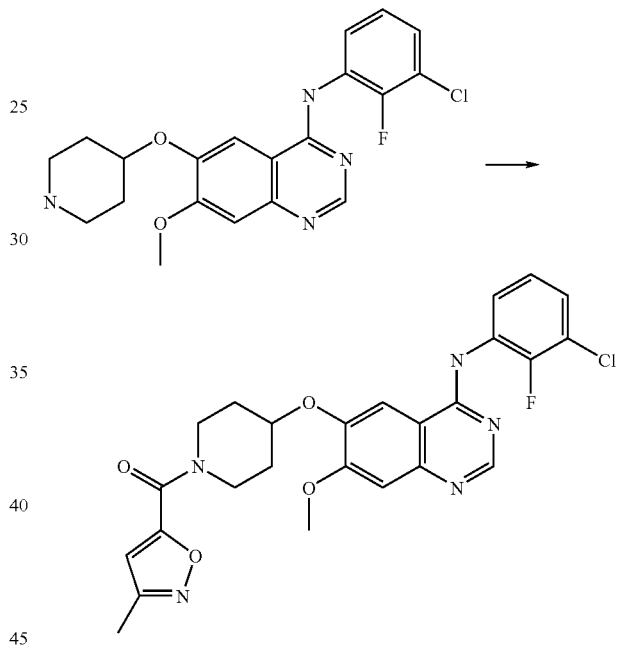

HATU (0.31 g) was added to a solution of N-(3-chloro-2-fluorophenyl)-7-methoxy-6-(piperidin-4-yloxy)quinazolinamine dihydrochloride (300 mg), diisopropylethylamine (0.45 ml) and 3-methyl-5-isoxazolecarboxylic acid (0.126 g) in methylene chloride (9 ml). The resulting mixture was stirred at room temperature for 2.5 hrs. Methylene chloride (20 ml) was added and the organics washed with aqueous sodium hydroxide (2M, 30 ml) and water (30 ml). The crudes were then purified by flash column chromatography eluting with methanol/methylene chloride (2.5/97.5). Fractions containing the desired product were evaporated to a white foam which was triturated with diethyl ether (20 ml) to give N-(3-chloro-2-fluorophenyl)-7-methoxy-6-({1-[(3-methylisoxazol-5-yl)carbonyl]piperidin-4-yl}oxy)quinazolinamine as a white solid (0.145 g). $^1$H NMR Spectrum: (DMSO $d_6$ 373K) 1.89 (m, 2H), 2.10 (m, 2H), 2.35 (s, 3H), 3.64 (m, 2H), 3.88 (m, 2H), 3.99 (s, 3H), 4.82 (m, 1H), 6.73 (s, 1M), 7.29 (m, 1H), 7.29 (s, 1H), 7.42 (m, 1H), 7.59 (m, 1H), 7.93 (s, 1H), 8.39 (s, 1H), 9.28 (br s, 1H); Mass Spectrum: (M+H)$^+$ 512.

The staring material was prepared in the manner described in Example 1 above.

EXAMPLE 3

Preparation of Compound No 4 in Table 1

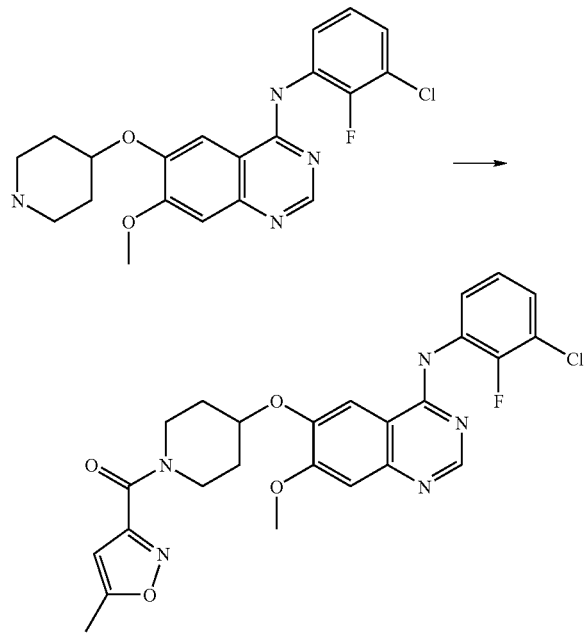

HATU (0.31 g) was added to a solution of N-(3-chloro-2-fluorophenyl)-7-methoxy-6-(piperidin-4-yloxy)quinazolin-4-amine dihydrochloride (300 mg), diisopropylethylamine (0.45 ml) and 5-methyl-3-isoxazolecarboxylic acid (0.127 g) in methylene chloride (9 ml). The resulting mixture was stirred at room temperature for 2.5 hrs. Methylene chloride (20 ml) was added and the organics washed with aqueous sodium hydroxide (2M, 30 ml) and water (30 ml). The crudes were then purified by flash column chromatography eluting with methanol/methylene chloride (2.5/97.5). Fractions containing the desired product were evaporated to a white foam which was triturated with diethyl ether (20 ml) to give N-(3-chloro-2-fluorophenyl)-7-methoxy-6-({1-[(5-methylisoxazol-3-yl)carbonyl]piperidin-4-yl}oxy)quinazolin-4-amine as a white solid (0.115 g). $^1$H NMR Spectrum: (DMSO d$_6$ 373K) 1.87 (m, 2H), 2.08 (m, 2H), 2.48 (s, 3H), 3.61 (m, 2H), 3.89 (m, 2H), 3.96 (s, 3H), 4.80 (m, 1H), 6.40 (s, 1H), 7.22 (m, 1H), 7.22 (s, 1H), 7.42 (m, 1H), 7.59 (m, 1H), 7.90 (s, 1H), 8.39 (s, 1H), 9.26 (br s, 1H); Mass Spectrum: (M+H)$^+$ 512.

The staring material was prepared in the manner described in Example 1 above.

EXAMPLE 4

Preparation of Compound No 5 in Table 1

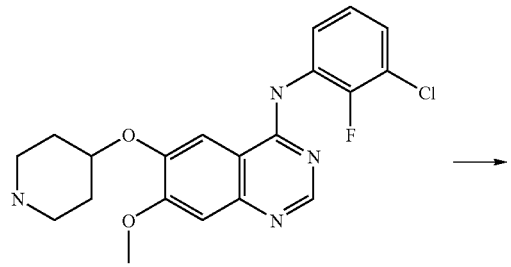

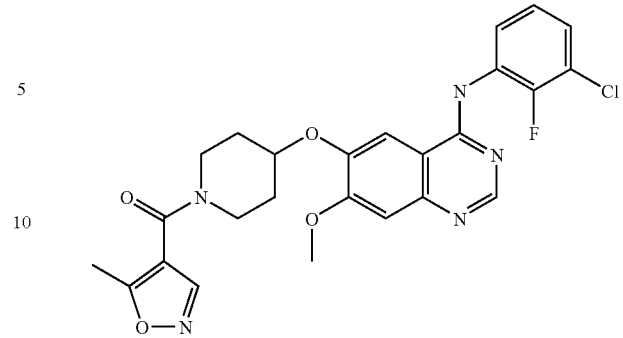

HATU (0.31 g) was added to a solution of N-(3-chloro-2-fluorophenyl)-7-methoxy-6-(piperidin-4-yloxy)quinazolin-4-amine dihydrochloride (300 mg), diisopropylethylamine (0.45 ml) and 5-methyl-4-isoxazolecarboxylic acid (0.127 g) in methylene chloride (9 ml). The resulting mixture was stirred at room temperature for 2.5 hrs. Methylene chloride (20 ml) was added and the organics washed with aqueous sodium hydroxide (2M, 30 ml) and water (30 ml). The crudes were then purified by flash column chromatography eluting with methanol/methylene chloride (2.5/97.5). Fractions containing the desired product were evaporated to a white foam which was triturated with diethyl ether (20 ml) to give N-(3-chloro-2-fluorophenyl)-7-methoxy-6-({1-[(5-methylisoxazol-4-yl)carbonyl]piperidin-4-yl}oxy)quinazolin-4-amine as a white solid (0.138 g). $^1$H NMR Spectrum: (DMSO d$_6$ 373K) 1.83 (m, 2H), 2.08 (m, 2H), 2.40 (s, 3H), 3.52 (m, 2H), 3.80 (m, 2H), 3.97 (s, 3H), 4.79 (m, 1H), 7.24 (m, 1H), 7.24 (s, 1H), 7.42 (m, 1H), 7.59 (m, 1H), 7.89 (s, 1H), 8.39 (s, 1H), 8.59 (s, 1H), 9.27 (br s, 1H); Mass Spectrum: (M+H)$^+$ 512.

The staring material was prepared in the manner described in Example 1 above.

EXAMPLE 5

Preparation of Compound No 6 in Table 1

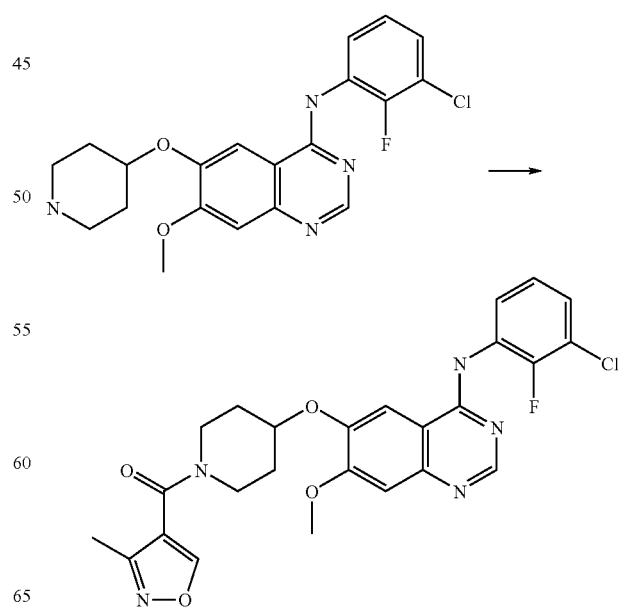

HATU (0.31 g) was added to a solution of N-(3-chloro-2-fluorophenyl)-7-methoxy-6-(piperidin-4-yloxy)quinazolin-4-amine dihydrochloride (300 mg), diisopropylethylamine (0.45 ml) and 3-methyl-4-isoxazolecarboxylic acid (0.128 g) in methylene chloride (9 ml). The resulting mixture was stirred at room temperature for 2.5 hrs. Methylene chloride (20 ml) was added and the organics washed with aqueous sodium hydroxide (2M, 30 ml) and water (30 ml). The crudes were then purified by flash column chromatography eluting with methanol/methylene chloride (2.5/97.5). Fractions containing the desired product were evaporated to a white foam which was triturated with diethyl ether (20 ml) to give N-(3-chloro-2-fluorophenyl)-7-methoxy-6-({1-[(3-methylisoxazol-4-yl)carbonyl]piperidin-4-yl}oxy)quinazolin-4-amine as a white solid (0.068 g). $^1$H NMR Spectrum: (DMSO d$_6$ 373K) 1.86 (m, 2H), 2.02 (m, 2H), 2.30 (s, 3H), 3.52 (m, 2H), 3.82 (m, 2H), 3.96 (s, 3H), 4.79 (m, 1H), 7.22 (m, 1H), 7.22 (s, 1H), 7.40 (m, 1H), 7.58 (m, 1H), 7.89 (s, 1H), 8.39 (s, 1H), 9.00 (s, 1H), 9.25 (br s, 1H); Mass Spectrum: (M+H)$^+$ 512

The staring material was prepared in the manner described in Example 1 above.

EXAMPLE 6

Preparation of Compound No. 7 in Table 1

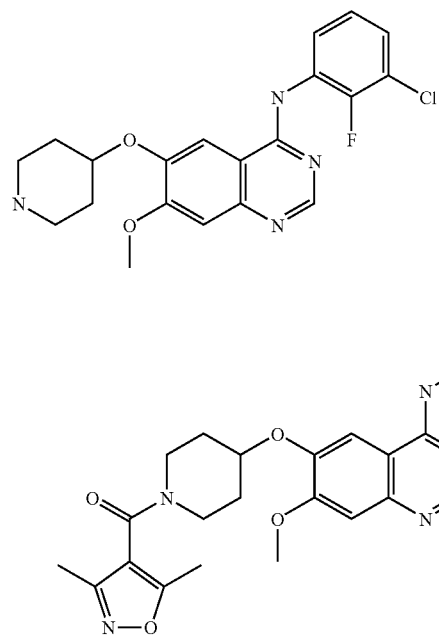

HATU (0.31 g) was added to a solution of N-(3-chloro-2-fluorophenyl)-7-methoxy-6-(piperidin-4-yloxy)quinazolin-4-amine dihydrochloride (300 mg), diisopropylethylamine (0.45 ml) and 3,5-dimethyl-4-isoxazolecarboxylic acid (0.141 g) in methylene chloride (9 ml). The resulting mixture was stirred at room temperature for 2.5 hrs. Methylene chloride (20 ml) was added and the organics washed with aqueous sodium hydroxide (2M, 30 ml) and water (30 ml). The crudes were then purified by flash column chromatography eluting with methanol/methylene chloride (2.5/97.5). Fractions containing the desired product were evaporated to a white foam which was triturated with diethyl ether (20 ml) to give N-(3-chloro-2-fluorophenyl)-6-({1-[(3,5-dimethylisoxazol-4-yl)carbonyl]piperidin-4-yl}oxy)-7-methoxyquinazolin-4-amine as a white solid (0.107 g). $^1$H NMR Spectrum: (DMSO d$_6$ 373K) 1.80 (m, 2H), 2.01 (m, 2H), 2.20 (s, 3H), 2.40 (s, 3H), 3.47 (m, 2H), 3.75 (m, 2H), 3.96 (s, 3H), 4.76 (m, 1H), 7.23 (m, 1H), 7.23 (s, 1H), 7.40 (m, 1H), 7.58 (m, 1H), 7.89 (s, 1H), 8.39 (s, 1H), 9.25 (br s, 1H); Mass Spectrum: (M+H)$^+$ 526.

The staring material was prepared in the manner described in Example 1 above.

EXAMPLE 7

Preparation of Compound No 2 in Table 1

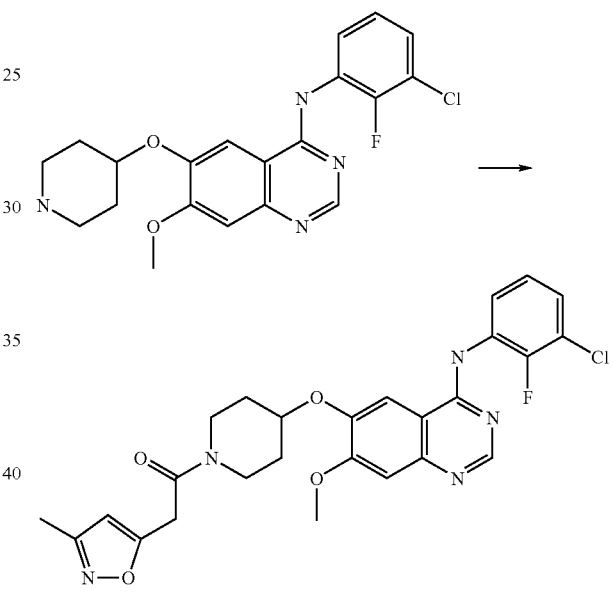

HATU (0.31 g) was added to a solution of N-(3-chloro-2-fluorophenyl)-7-methoxy-6-(piperidin-4-yloxy)quinazolin-4-amine dihydrochloride (300 mg), diisopropylethylamine (0.45 ml) and 3-methyl-5-isoxazoleacetic Acid (0.135 g) in methylene chloride (9 ml). The resulting mixture was stirred at room temperature for 2.5 hrs. Methylene chloride (20 ml) was added and the organics washed with aqueous sodium hydroxide (2M, 30 ml) and water (30 ml). The crudes were then purified by flash column chromatography eluting with methanol/methylene chloride (2.5/97.5). Fractions containing the desired product were evaporated to a white foam which was triturated with diethyl ether (20 ml) to give N-(3-chloro-2-fluorophenyl)-7-methoxy-6-({1-[(3-methylisoxazol-5-yl)acetyl]piperidin-4-yl}oxy)quinazolin-4-amine as a white solid (0.269 g). $^1$H NMR Spectrum: (DMSO d$_6$ 373K) 1.79 (m, 2H), 1.98 (m, 2H), 2.23 (s, 3H), 3.50 (m, 2H), 3.79 (m, 2H), 3.92 (s, 2H), 3.97 (s, 3H), 4.77 (m, 1H), 6.18 (s, 1H), 7.24 (m, 2H), 7.42 (m, 1H), 7.59 (m, 1H), 7.89 (s, 1H), 8.39 (s, 1H), 9.28 (br s, 1H); Mass Spectrum: (M+H)$^+$ 526.

The staring material was prepared in the manner described in Example 1 above.

EXAMPLES 8 to 31

Preparation of Compound Nos. 8 to 31 in Table 1

Generic Process

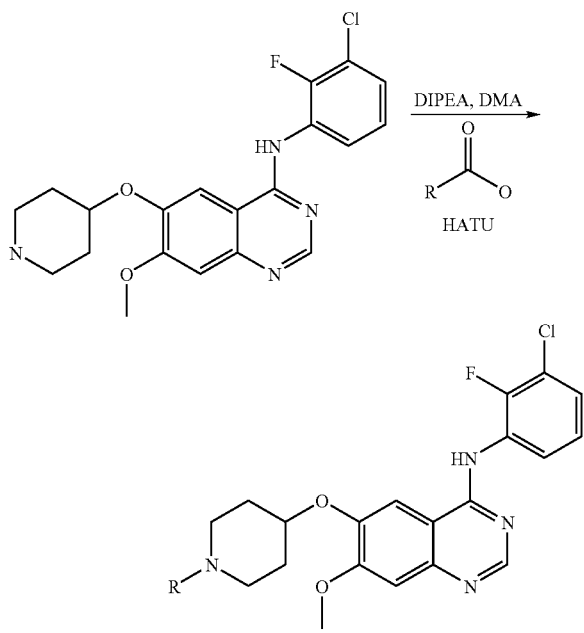

Solid HATU (119 mg, 0.815 mmol) and DIPEA (0.171 ml, 0.96 mmol) were dissolved in anhydrous DMA (0.5 ml) were added to a solution of (3-chloro-2-fluorophenyl)-[7-méthoxy-6-(piperidin-4-yloxy)-quinazolin-4-yl]-amine.dihydrochloride (100 mg, 0.24 mmol), and the carboxylic acid (0.36 mmol) in DMA (0.5 ml) at room temperature. The resulting solution was allowed to stir at room temperature overnight. The crude reaction mixtures were purified using mass-triggered preparative LCMS.

The fractions containing the desired compound were evaporated in a Genevac and the residue taken up in 10% (v/v) MeOH in DCM (0.4 ml), diluted with 6 ml of 15% (v/v) $Et_2O$ in pentane and left at 4° C. overnight. The resulting precipitates were collected by filtration and dried to a constant weight to afford the desired amides as amorphous or crystalline solids.

Standard Conditions for Purification by Mass-Triggered Preparative LCMS

Column: ThermoHypersil Keystone B-Basic 5µ 21 mm×100 mm

Eluant: 7.5 minutes Gradient from 20% to 95% of acetonitrile in water (buffer 2 g/l of $(NH_4)_2CO_3$, pH 8.9).

Flow rate: 25 ml/min.

The staring material was prepared in the manner described in Example 1 above.

| Example/ Compound No. | R | MH+ | NMR δ en ppm (DMSO + TFAd) | Yield |
|---|---|---|---|---|
| 8 | | 508.2 | 1.82–2.01 (m, 2 H); 2.04–2.28 (m, 2 H); 3.35–3.46 (m, 1 H); 3.58–3.75 (m, 2 H); 3.96–4.10 (m, 1 H); 4.05 (s, 3 H); 4.95 (M, 1 H); 7.39 (s, 1 H); 7.41 (dd, 1 H); 7.58(dd, 1 H); 7.69 (dd, 1 H); 8.15 (dd, 1 H); 8.17 (s, 1 H); 8.69 (d, 1 H); 8.93 (s, 1 H); 9.02 (d, 1 H); 9.14 (s, 1 H). | 37 |
| 9 | | 527.1 | 1.64–1.74 (m, 2 H); 1.98–2.09 (m, 2 H); 3.37–3.57 (m, 2 H); 3.80–3.94 (m, 2 H); 4.02 (dd, 2 H); 4.04 (s, 3 H); 4.85 (bs, 1 H); 6.97 (s, 1 H); 6.98 (dd, 1 H); 7.37 (s, 1 H); 7.37–7.44 (m, 2 H); 7.59 (dd, 1 H); 7.68 (dd, 1 H); 8.12 (s, 1 H); 8.92 (s, 1 H). | 35 |
| 10 | | 508.1 | 1.80–1.95 (m, 2 H); 2.05–2.25 (m, 2 H); 3.38–3.47 (m, 1 H); 3.62–3.75 (m, 2 H); 3.94–4.04 (m, 1 H); 4.06 (s, 3 H); 4.94 (bs, 1 H); 7.39 (s, 1 H); 7.41 (dd, 1 H); 7.59 (ddd, 1 H); 7.75–7.71 (m, 2 H); 7.80 (d, 1 H); 8.15 (ddd, 1 H); 8.17 (s, 1 H); 8.73 (d, 1 H); 8.92 (s, 1 H). | 30 |

-continued
| Example/ Compound No. | R | MH+ | NMR δ en ppm (DMSO + TFAd) | Yield |
|---|---|---|---|---|
| 11 | 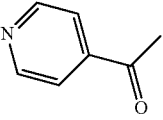 | 508.2 | 1.81–1.90 (m, 1 H); 1.90–1.99 (m, 1 H); 2.03–2.13 (m, 1 H); 2.18–2.26 (m, 1 H); 3.26–3.34 (m, 1 H); 3.47–3.56 (m, 1 H); 3.65–3.74 (m, 1 H); 3.94–4.03 (m, 1 H); 4.05 (s, 3 H); 4.94 (bs, 1 H); 7.37 (s, 1 H); 7.41 (dd, 1 H); 7.58 (ddd, 1 H); 7.69 (ddd, 1 H); 8.16 (s, 1 H); 8.19 (d, 2 H); 8.92 (s, 1 H); 8.19 (d, 2 H); 8.92 (s, 1 H); 9.08 (d, 2 H). | 31 |
| 12 | 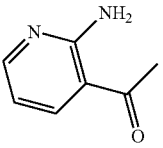 | 523.2 | 1.71–2.01 (m, 2 H): 2.01–2.33 (m, 2 H); 3.27–3.46 (m, 1 H); 3.48–3.72 (m, 2 H); 3.88–4.03 (m, 1 H); 4.05 (s, 3 H); 4.92 (bs, 1 H); 6.99 (dd, 1 H); 7.38 (s, 1 H); 7.41 (dd, 1 H); 7.58 (ddd, 1 H); 7.69 (ddd, 1 H); 8.03–8.10 (m, 2 H); 8.15 (s, 1 H); 8.92 (s, 1 H). | 19 |
| 13 | 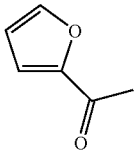 | 497.2 | 1.79–1.92 (m, 2 H); 2.10–223 (m,2 H); 3.58–3.77 (m, 2 H); 3.9114 4.09 (m, 2 H); 4.06 (s, 3 H); 4.93 (bs, 1 H); 6.63 (dd, 1 H); 7.03 (d, 1 H); 7.38 (s, 1 H); 7.41 (dd, 1 H); 7.59 (ddd, 1 H); 7.69 (ddd, 1 H); 7.83 (dd, 1 H); 8.17 (s, 1 H); 8.92 (s, 1 H). | 28 |
| 14 | 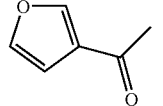 | 497.1 | 1.77–1.88 (m, 2 H); 2.09–2.18 (m, 2 H); 3.54–3.63 (m, 2 H); 3.86–3.98 (m, 2 H); 4.05 (s, 3 H); 4.92 (bs, 1 H); 6.70 (dd, 1 H); 7.38 (s, 1 H); 7.41 (ddd, 1 H); 7.59 (ddd, 1 H); 7.68 (ddd, 1 H); 7.73 (dd, 1 H); 8.06 (s, 1 H); 8.16 (s, 1 H); 8.92 (s, 1 H). | 33 |
| 15 | 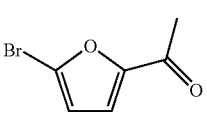 | 575.1 | 1.79–1.90 (m, 2 H); 2.11–2.21 (m, 2 H); 3.59–3.74 (m, 2 H); 3.91–4.02 (m, 2 H); 4.05 (s, 3 H); 4.92 (bs, 1 H); 6.76 (d, 1 H); 7.07 (d, 1 H); 7.37 (s, 1 H); 7.41 (dd, 1 H); 7.59 (dd, 1 H); 7.69 (dd, 1 H); 8.16 (s, 1 H); 8.92 (s, 1 H). | 41 |
| 16 | 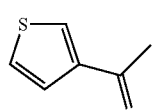 | 513.1 | 1.77–1.90 (m, 2 H); 2.06–2.21 (m, 2 H); 3.44–3.64 (3, 2 H); 3.65–4.11 (m, 2 H); 4.06 (s, 3 H); 4.92 (bs, 1 H); 7.27 (dd, 1 H); 7.37 (s, 1 H); 7.41 (dd, 1 H); 7.59 (ddd, 1 H); 7.62 (dd, 1 H); 7.69 (ddd, 1 H); 7.83 (dd, 1 H); 8.16 (s, 1 H); 8.92 (s, 1 H). | 37 |

| Example/ Compound No. | R | MH+ | NMR δ en ppm (DMSO + TFAd) | Yield |
|---|---|---|---|---|
| 17 | 3-amino-1H-pyrazol-4-yl ketone | 512.2 | 1.82–1.94 (m, 2 H); 2.11–2.23 (m, 2 H); 3.56–3.68 (m, 2 H); 3.92–4.02 (m, 2 H); 4.06 (s, 3 H); 4.95 (bs, 1 H); 7.39 (s, 1 H); 7.41 (dd, 1 H); 7.59 (ddd, 1 H); 7.68 (ddd, 1 H); 8.19 (s, 1 H); 8.33 (s, 1 H); 8.93 (s, 1 H). | 37 |
| 18 | quinolin-2-yl ketone | 558.2 | 1.81–1.97 (m, 2 H); 2.10–2.18 (m, 1 H); 2.19–2.29 (m, 1 H); 3.44–3.55 (m, 1 H); 3.70–3.80 (m, 2 H); 4.02–4.11 (m, 1 H); 4.06 (s, 3 H); 4.96 (bs, 1 H); 7.38 (s, 1 H); 7.41 (dd, 1 H); 7.59 (ddd, 1 H); 7.68 (dd, 1 H); 7.72 (ddd, 1 H); 7.78 (d, 1 H); 7.88 (ddd, 1 H); 8.08 (d, 1 H); 8.10 (d, 1 H); 8.17 (d, 1 H); 8.10 (d, 1 H); 8.17 (s, 1 H); 8.59 (d, 1 H); 8.92 (s, 1 H). | 22 |
| 19 | benzofuran-2-yl ketone | 547.2 | 1.84–1.95 (m, 2 H); 2.16–2.26 (m, 2 H); 3.64–3.84 (m, 2 H); 3.96–4.10 (m, 2 H); 4.06 (s, 3 H); 4.96 (bs, 1 H); 7.35 (dd, 1 H); 7.38 (s, 1 H); 7.42 (ddd, 1 H); 7.45 (s, 1 H); 7.46 (ddd, 1 H); 7.59 (ddd, 1 H); 7.67 (d, 1 H); 7.69 (ddd, 1 H); 7.76 (d, 1 H); 8.18 (s, 1 H); 8.92 (s, 1 H). | 31 |
| 20 | benzothiophen-2-yl ketone | 563.2 | 1.84–1.97 (m, 2 H); 2.15–2.26 (m, 2 H); 3.65–3.80 (m, 2 H); 3.97–4.05 (m, 2 H); 4.06 (s, 3 H); 4.96 (bs, 1 H); 7.38 (s, 1 H); 7.41 (ddd, 1 H); 7.44–7.50 (m, 2 H); 7.59 (ddd, 1 H); 7.69 (ddd, 1 H); 7.79 (s, 1 H); 7.94 (dd, 1 H); 8.03 (dd, 1 H); 8.18 (s, 1 H); 8.93 (s, 1 H). | 43 |
| 21 | quinolin-3-yl ketone | 558.2 | 1.89–2.02 (m, 2 H); 2.07–2.19 (m, 1 H); 2.20–2.31 (m, 1 H); 3.47–3.60 (m, 1 H); 3.67–3.86 (m, 2 H); 4.01–4.14 (m, 1 H); 4.07 (s, 3 H); 4.98 (bs, 1 H); 7.40 (s, 1 H); 7.41 (dd, 1 H); 7.58 (dd, 1 H); 7.68 (dd, 1 H); 7.99 (dd, 1 H); 8.18 (s, 1 H); 8.19 (s, 1 H); 8.31 (d, 1 H); 8.40 (d, 1 H); 8.93 (s, 1 H); 9.26 (s, 1 H); 9.49 (d, 1 H). | 28 |
| 22 | 1H-indol-3-yl ketone | 546.2 | 1.79–1.89 (m, 2 H); 2.13–2.22 (m, 2 H); 3.55–3.66 (m, 2 H); 3.98–4.09 (m, 2 H); 4.06 (s, 3 H); 4.92 (bs, 1 H); 713 (dd, 1 H); 7.18 (dd, 1 H); 7.38 (s, 1 H); 7.41 (dd, 1 H); 7.47 (d, 1 H); 7.59 (ddd, 1 H); 7.69 (ddd, 1 H); 7.73 (d, 1 H); 7.75 (s, 1 H); 8.16 (s, 1 H); 8.92 (s, 1 H). | 36 |

-continued

| Example/ Compound No. | R | MH+ | NMR δ en ppm (DMSO + TFAd) | Yield |
|---|---|---|---|---|
| 23 | (3-thienyl-CH2-C(=O)-) | 527.2 | 1.57–1.74 (m, 2 H); 1.91–2.00 (m, 1 H); 2.00–2.08 (m, 1 H); 3.37–3.57 (m, 2 H); 3.74–3.86 (m, 1 H); 3.76 (d, 1 H); 3.81 (d, 1 H); 3.85–3.95 (m, 1 H); 4.04 (s, 3 H); 4.82 (bs, 1 H); 7.03 (dd, 1 H); 7.30 (d, 1 H); 7.36 (s, 1 H); 7.41 (ddd, 1 H); 7.49 (dd, 1 H); 7.58 (ddd, 1 H); 7.68 (ddd, 1 H); 8.11 (s, 1 H); 8.91 (s, 1 H). | 39 |
| 24 | 5-bromo-2-thienyl-C(=O)- | 591.1 | 1.81–1.93 (m, 2 H); 2.11–2.22 (m, 2 H); 3.61–3.74 (m, 2 H); 3.89–3.98 (m, 2 H); 4.05 (s, 3 H); 4.93 (bs, 1 H); 7.26 (bs, 1 H); 7.33 (bs, 1 H); 7.37 (s, 1 H); 7.41 (dd, 1 H); 7.59 (dd, 1 H); 7.69 (bs, 1 H); 8.16 (s, 1 H); 8.92 (s, 1 H). | 43 |
| 25 | 2,6-dichloro-4-pyridyl-C(=O)- | 578.2 | 1.80–1.95 (m, 2 H); 2.03–2.12 (m, 1 H); 2.13–2.22 (m, 1 H); 3.26–3.36 (m, 1 H); 3.48–3.58 (m, 1 H): 3.60–3.70 (m, 1 H); 3.87–3.98 (m, 1 H); 4.05 (s, 3 H); 4.91 (bs, 1 H); 7.38 (s, 1 H); 7.42 (dd, 1 H); 7.58 (dd, 1 H); 7.69 (dd, 1 H); 7.72 (s, 2 H); 8.14 (s, 1 H); 8.92 (s, 1 H). | 39 |
| 26 | 5-methyl-2-thienyl-C(=O)- | 527.2 | 1.79–1.91 (m, 2 H); 2.10–2.21 (m, 2 H); 2.49 (s, 3 H); 3.19–3.72 (m, 2 H); 3.91–4.02 (m, 2 H); 4.06 (s, 3 H); 4.93 (bs, 1 H); 6.83 (dd, 1 H); 7.27 (d, 1 H); 7.38 (s, 1 H); 7.41 (ddd, 1 H); 7.59 (ddd, 1 H); 7.68 (ddd, 1 H); 8.17 (s, 1 H); 8.93 (s, 1 H). | 18 |
| 27 | 1-methyl-2-pyrrolyl-C(=O)- | 510.2 | 1.76–1.87 (m, 2 H); 2.09–2.20 (m, 2 H); 3.53–3.66 (m, 2 H7); 3.71 (s, 3 H:); 3.49–406 (m, 2 H); 4.06 (s, 3 H); 4.91 (bs, 1 H); 6.05 (dd, 1 H); 6.38 (dd, 1 H); 6.90 (dd, 1 H); 7.38 (s, 1 H); 7.42 (ddd, 1 H); 7.59 (ddd, 1 H); 7.69 (ddd, 1 H); 8.16 (s, 1 H); 8.92 (s, 1 H). | 35 |
| 28 | 1-methyl-2-indolyl-C(=O)- | 560.3 | 1.83–1.95 (m, 2 H); 2.12–2.26 (m, 2 H); 3.64–3.75 (m, 2 H); 3.82 (s, 3 H); 3.95–4.10 (m, 2 H); 4.07 (s, 3 H); 4.96 (bs, 1 H); 6.74 (s, 1 H); 7.12 (dd, 1 H); 7.27 (dd, 1 H); 7.39 (s, 1 H); 7.41 (dd, 1 H); 7.52 (d, 1 H); 7.59 (ddd, 1 H); 7.63 (d, 1 H); 7.69 (ddd, 1 H); 8.19 (s, 1 H); 8.93 (s, 1 H). | 33 |

-continued

| Example/ Compound No. | R | MH+ | NMR δ en ppm (DMSO + TFAd) | Yield |
|---|---|---|---|---|
| 29 | 2-chloropyridin-4-yl acetyl | 542.2 | 1.78–1.94 (m, 2 H); 2.02–2.13 (m, 1 H); 2.13–2.23 (m, 1 H); 3.25–3.38 (m, 1 H); 3.47–3.57 (m, 1 H); 3.61–3.71 (m, 1 H); 3.88–4.00 (m, 1 H); 4.05 (s, 3 H); 4.91 (bs, 1 H); 7.37 (s, 1 H); 7.41 (dd, 1 H); 7.50 (d, 1 H); 7.58 (dd, 1 H); 7.65 (s, 1 H); 7.69 (dd, 1 H); 8.15 (s, 1 H); 8.53 (d, 1 H); 8. | 14 |
| 30 | 1-(4-nitro-1H-pyrazol-1-yl)acetyl | 556.2 | 1.71–1.81 (m, 1 H); 1.85–1.96 (m, 1 H); 2.04–2.13 (m, 1 H); 2.14–2.23 (m, 1 H); 3.42–3.56 (m, 2 H); 3.75–3.91 (m, 2 H); 4.06 (s, 3 H); 4.91 (bs, 1 H); 5.36 (s, 2 H); 7.38 (s, 1 H); 7.42 (ddd, 1 H); 7.59 (ddd, 1 H); 7.69 (ddd, 1 H); 8.16 (s, 1 H); 8.27 (s, 1 H); 8.81 (s, 1 H); 8.93 (s, 1 H). | 30 |
| 31 | 3-nitro-1H-pyrazol-5-yl acetyl | 542.2 | 1.82–1.98 (m, 2 H); 2.11–2.23 (m, 2 H); 3.64–3.74 (m, 2 H); 3.85–3.99 (m, 2 H); 4.05 (s, 3 H); 3.94 (bs, 1 H); 7.38 (s, 1 H); 7.41 (dd, 1 H); 7.42 (s, 1 H); 7.59 (ddd, 1 H); 7.69 (ddd, 1 H); 8.17 (s, 1 H); 8.93 (s, 1 H). | 54 |

EXAMPLE 32

Preparation of Compound No 32 in Table II

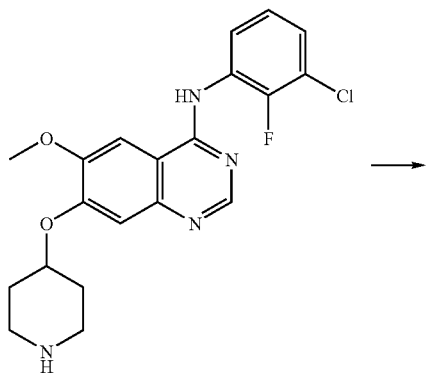

→

-continued

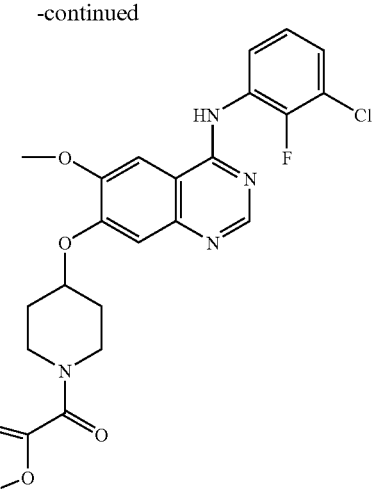

HATU (0.31 g) was added to a solution of N-(3-chloro-2-fluorophenyl)-6-methoxy-7-(piperidin-4-yloxy)quinazolin- 4-amine dihydrochloride (300 mg), diisopropylethylamine (0.45 ml) and isoxazole-5-carboxylic acid (0.110 g) in methylene chloride (9 ml). The resulting mixture was stirred at room temperature for 2.5 hrs. Methylene chloride (20 ml) was added and the organics washed with aqueous sodium hydroxide (2M, 30 ml) and water (30 ml). The crudes were then purified by flash column chromatography eluting with methanol/methylene chloride (2.5/97.5). Fractions containing the desired product were evaporated to a white foam which was triturated with diethyl ether (20 ml) to give N-(3-chloro-2-fluorophenyl)-7-{[1-(isoxazol-5-ylcarbonyl)piperidin-4-yl]oxy}-6-methoxyquinazolin-4-amine as a white solid (0.045 g). $^1$H NMR Spectrum: (DMSO $d_6$ 373K) 1.86 (m, 2H), 2.10 (m, 2H), 3.59 (m, 2H), 3.88 (m, 2H), 3.98 (s, 3H), 4.92 (m, 1H), 6.87 (s, 1H), 7.26 (m, 1H), 7.38 (s, 1H), 7.42 (m, 1H), 7.59 (m, 1H), 7.83 (s, 1H), 8.39 (s, 1H), 8.62 (s, 1H), 9.30 (br s, 1H); Mass Spectrum: (M+H)$^+$ 498.

Preparation of the Starting Material

Step 1

7-(benzyloxy)-N-(3-chloro-2-fluorophenyl)-6-methoxyquinazolin-4-amine hydrochloride 4.0M HCl in Dioxane (4.0 ml) was added to a stirred suspension of 7-(benzyloxy)-4-chloro-6-methoxyquinazoline (60 g, 0.2 mol) [prepared as described in WO98/13354, Example 1] and 3-chloro-2-fluoroaniline (31.96 g, 0.22 mol) in acetonitrile (1200 mL). The reaction mixture was heated at 80° C. for 1 hour then left to stand O/N. Acetonitrile (500 mL) was added and the resulting precipitate filtered, washed with Acetonitrile (3×500 mL) and dried under vacuum to give 7-(benzyloxy)-N-(3-chloro-2-fluorophenyl)-6-methoxyquinazolin-4-amine hydrochloride 2 as a beige solid (85.45 g, 96%); $^1$H NMR Spectrum: (DMSO $d_6$) 4.02 (s, 3H), 5.35 (s, 2H), 7.30-7.60 (m, 9H), 7.65 (m, 1H), 8.38 (s, 1H), 8.85 (s, 1H), 11.8 (s, 1H); Mass Spectrum: (M+H)$^+$ 410.27.

Step 2

4-[(3-chloro-2-fluorophenyl)amino]-6-methoxyquinazolin-7-ol

A solution of 7-(benzyloxy)-N-(3-chloro-2-fluorophenyl)-6-methoxyquinazolin-4-amine hydrochloride 2 (85.45 g, 0.192 mol) in trifluoroacetic acid (300 mL) was heated at 80° C. for 1 hour. The reaction mixture was the evaporated to dryness and the residues re-dissolved in methanol (200 mL). This solution was then added dropwise to a stirred aqueous solution of saturated sodium bicarbonate (500 mL). The resulting precipitate was collected by filtration, washed with acetonitrile and dried under vacuum. The crude solids were then purified by hot (100° C.) trituration with a mixture of butanone (500 mL) and MeOH (100 mL), filtered and dried to 4-[(3-chloro-2-fluorophenyl)amino]-6-methoxyquinazolin-7-ol 3 as a cream solid (45 g, 73%); $^1$H NMR Spectrum: (DMSO $d_6$): 3.98 (s, 3H), 7.10 (s, 1H), 7.25-7.30 (m, 1H), 7.40-7.50 (m, 1H), 7.50-7.60 (m, 1H), 7.80 (s, 1H), 8.30 (s, 1H), 9.55 (s, 1H), 10.32 (s, 1H); Mass Spectrum: (M+H)$^+$ 319.98

Step 3 tert-butyl 4-({4-[(3-chloro-2-fluorophenyl)amino]-6-methoxyquinazolin-7-yl}oxy)piperidine-1-carboxylate 4-[(3-chloro-2-fluorophenyl)amino]-6-methoxyquinazolin-7-ol (3, 500 mg, 1.565 mmol) was dissolved in DMA (20 ml). tert-Butyl(4-methanesulfonyloxy)piperidine-1-carboxylate (436.6 mg, 1.565 mmol) and cesium fluoride (236.3 mg, 1.565 mmol) were added, and the mixture was heated to 60° C. with stirring. After 18 hours, tert-butyl 4-methanesulfonyloxypiperidine-1-carboxylate and cesium fluoride were again added in the same quantities to the reaction mixture and heating was continued at 60° C. for a further 18 hours. The solvent was evaporated, and the residue was partitioned between saturated aqueous sodium bicarbonate solution (50 mL) and EtOAc (2×50 mL). The organics were combined, dried over MgSO$_4$ and evaporated. The crudes were then purified by column chromatography eluting with increasingly polar mixtures of methylene chloride/EtOAc (100/0 to 0/100). The fractions containing the desired product were combined and evaporated under vacuum to give tert-butyl 4-({4-[(3-chloro-2-fluorophenyl)amino]-6-methoxyquinazolin-7-yl}oxy)piperidine-1-carboxylate as a colourless foam (757 mg, 96%); $^1$H NMR Spectrum: (DMSO-$d_6$): 1.52 (s, 9H), 1.60-1.80 (m, 2H), 2.02-2.20 (m, 2H), 3.20-3.45 (m, 2H), 3.75-3.92 (m, 2H), 4.05 (s, 3H), 4.95 (m, 1H), 7.32-7.45 (m, 2H), 7.55-7.70 (m, 2H), 7.92 (s, 1H), 8.50 (s, 1H), 9.73 (s, 1H); Mass Spectrum: (M+H)$^+$ 503.08.

Step 5

N-(3-chloro-2-fluorophenyl)-6-methoxy-7-(piperidin-4-yloxy)quinazolin-4-amine dihydrochloride

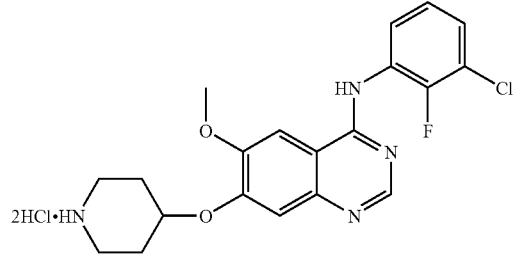

Trifluoroacetic acid (50 mL) was added to a solution of tert-butyl 4-({4-[(3-chloro-2-fluorophenyl)amino]-6-methoxyquinazolin-7-yl}oxy)piperidine-1-carboxylate (750 m g, 1.49 mmol) in methylene chloride (1 mL) and Triethylsilane (1 mL) and the solution stirred for 1 hour. The reaction mixture was then evaporated under reduced pressure and the residues re-dissolved in EtOAc (5 mL). This solution was then treated with 1M HCl/Diethylether (1 mL) followed by more Diethylether (50 mL) to give a heavy white precipitation. The resulting solids were collected following centrifugation and dried under vacuum to give N-(3-chloro-2-fluorophenyl)-6-methoxy-7-(piperidin-4-yloxy)quinazolin-4-amine dihydrochloride 5 as an white solid (750 mg); $^1$H NMR Spectrum: (DMSO-$d_6$): 2.00-2.20 (m, 2H), 2.25-2.45 (m, 2H), 3.15-3.50 (m, 4H), 4.15 (s, 3H), 5.02 (m, 1H), 7.48 (m, 1H), 7.60-7.85 m, 3H), 8.35 (s, 1H), 8.85 (s, 1H), 9.56 (bs, 2H); Mass Spectrum: (M+H)$^+$ 403.08.

EXAMPLE 33

Preparation of Compound No 33 in Table II

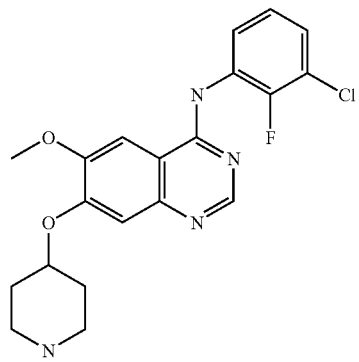

→

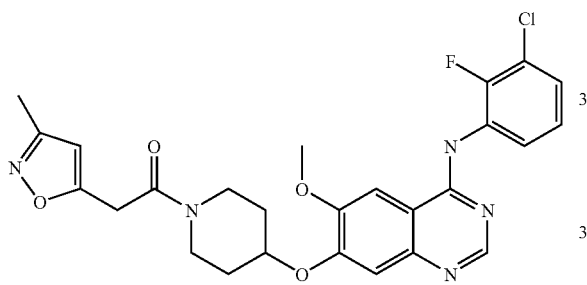

HATU (0.31 g) was added to a solution of N-(3-chloro-2-fluorophenyl)-6-methoxy-7-(piperidin-4-yloxy)quinazolin-4-amine dihydrochloride 5 (300 mg), diisopropylethylamine (0.45 ml) and 3-methyl-5-isoxazoleacetic acid (0.135 g) in methylene chloride (9 ml). The resulting mixture was stirred at room temperature for 2.5 hrs. Methylene chloride (20 ml) was added and the organics washed with aqueous sodium hydroxide (2M, 30 ml) and water (30 ml). The crudes were then purified by flash column chromatography eluting with methanol/methylene chloride (4/96). Fractions containing the desired product were evaporated to a white foam which was triturated with diethyl ether (20 ml) to give N-(3-chloro-2-fluorophenyl)-6-methoxy-7-({1-[(3-methylisoxazol-5-yl)carbonyl]piperidin-4-yl}oxy)quinazolin-4-amine as a white solid (0.224 g). $^1$H NMR Spectrum: (DMSO $d_6$) 1.54-1.76 (m, 2H), 2.05 (m, 2H), 2.22 (s, 3H), 3.32 (m, 1H), 3.47 (m, 1H), 3.82 (m, 1H), 3.93 (m, 1H), 3.96 (s, 3H), 4.00 (s, 2H), 4.92 (m, 1H), 6.23 (s, 1H), 7.29 (m, 1H), 7.36 (s, 1H), 7.48 (m, 1H), 7.53 (m, 1H), 7.83 (s, 1H), 8.39 (s, 1H), 9.63 (br s, 1H); Mass Spectrum: $(M+H)^+$ 526.

The staring material was prepared in the manner described in Example 32 above.

EXAMPLES 34 TO 58

Preparation of Compound Numbers 34 to 58 of Table II

Generic Process

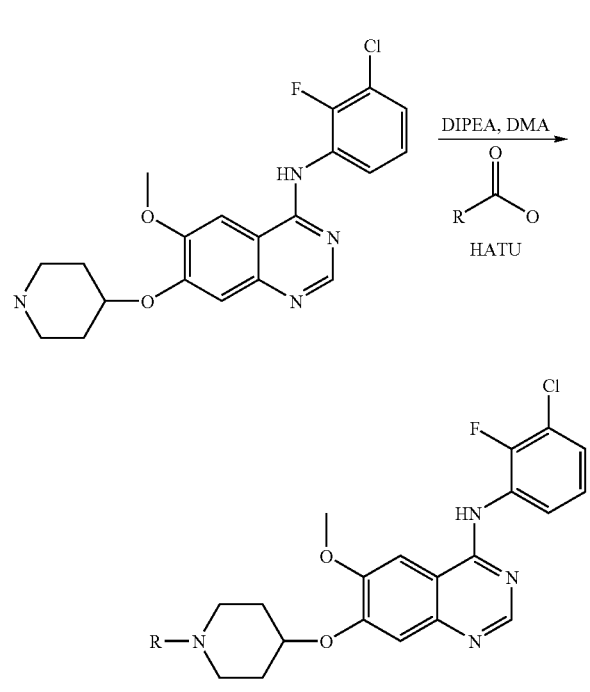

Solid HATU (119 mg, 0.815 mmol) and DIPEA (0.171 ml, 0.96 mmol) were dissolved in anhydrous DMA (0.5 ml) were added to a solution of (3-chloro-2-fluorophenyl)-[6-methoxy-7-(piperidinyloxy)-quinazolin-4-yl]-amine.dihydrochloride (100 mg, 0.24 mmol), and the carboxylic acid (0.36 mmol) in DMA (0.5 ml) at room temperature. The resulting solution was allowed to stir at room temperature overnight. The crude reaction mixtures were purified using mass-triggered preparative LCMS.

The fractions containing the desired compound were evaporated in a Genevac and the residue taken up in 10% (v/v) MeOH in DCM (0.4 ml), diluted with 6 ml of 15% (v/v) Et$_2$O in pentane and left at 4° C. overnight. The resulting precipitates were collected by filtration and dried to a constant weight to afford the desired amides as amorphous or crystalline solids.

The staring material was prepared in the manner described in Example 32 above.

Standard Conditions for Purification by Mass-Triggered Preparative LCMS

Column: ThermoHypersil Keystone B-Basic 5µ 21 mm×100 mm

Eluant: 7.5 minutes Gradient from 20% to 95% of acetonitrile in water (buffer 2 g/l of (NH$_4$)$_2$CO$_3$, pH 8.9).

Flow rate: 25 ml/min.

| Example Compound No. | R | MH+ | NMR δ en ppm (DMSO + TFAd) | Yield |
|---|---|---|---|---|
| 34 | pyridin-3-yl-C(O)-CH2- | 508.1 | 1.84–2.01 (m, 2 H); 2.04–2.29 (m, 2 H); 3.35–3.48 (m, 1 H); 3.56–3.71 (m, 2 H); 3.99–4.12 (m, 1 H); 4.04 (s, 3 H); 5.02 (bs, 3 H); 7.40 (ddd, 1 H); 7.55 (s, 1 H); 7.58 (ddd, 1 H); 7.67 (ddd, 1 H); 8.14 (s, 1 H); 8.17 (dd, 1 H); 8.71 (s, 1 H); 8.92 (d, 1 H); 9.04 (d, 1 H); 9.16 (s, 1 H). | 67 |
| 35 | thiophen-2-yl-CH2-C(O)-CH2- | 527.1 | 1.64–1.75 (m, 2 H); 2.00–2.11 (m, 2 H); 3.36–3.44 (m, 1 H); 3.49–3.56 (m, 1 H); 3.83–3.90 (m, 1 H); 3.91–3.99 (m, 1 H); 5.02 (bs, 5 H); 4.91 (bs, 1 H); 6.95–7.01 (m, 2 H); 3.36–3.43 (m, 2 H); 7.46 (s, 1 H); 7.57 (dd, 1 H); 7.66 (dd, 1 H); 8.11 (s, 1 H); 8.90 (s, 1 H). | 15 |
| 36 | pyridin-2-yl-C(O)-CH2- | 508.1 | 1.80–1.95 (m, 2 H); 2.06–2.16 (m, 1 H); 2.17–2.27 (m, 1 H); 3.39–3.49 (m, 3.99–4.11 (m, 1 H); 4.04 (s, 1 H); 3.62–3.73 (m, 2 H); 3 H); 5.02 (bs, 1 H); 7.40 (dd, 1 H); 7.51 (s, 1 H); 7.58 (dd, 1 H); 7.64–7.74 (m, 2 H); 7.82–7.87 (m, 1 H); 8.13 (s, 1 H); 8.16–8.23 (m, 1 H); 8.73–8.78 (m, 1 H); 8.98 (s, 1 H). | 37 |
| 37 | 2-amino-pyridin-3-yl-C(O)- | 523.1 | 1.76–2.31 (m, 4 H); 3.30–3.46 (m, 1 H); 3.47–3.68 (m, 2 H); 3.94–4.11 (m, 1 H); 4.03 (m, 3 H); 4.99 (bs, 1 H); 6.99 (dd, 1 H); 7.41 (dd, 1 H); 7.54 (s, 1 H); 7.58 (ddd, 1 H); 7.67 (ddd, 1 H); 8.05 (dd, 1 H); 8.09 (dd, 1 H); 8.13 (s, 1 H); 8.92 (s, 1 H). | 9 |
| 38 | 1H-pyrrol-2-yl-C(O)- | 496.1 | 1.77–1.87 (m, 2 H); 2.12–2.22 (m, 2 H); 3.59–3.70 (m, 2 H); 4.04 (s, 3 H); 4.06–4.16 (m, 2 H); 4.95–5.02 (m, 1 H) 6.14 (dd, 1 H); 6.54 (d, 1 H); 6.92 (bs, 1 H); 7.41 (dd, 1 H); 7.50 (s, 1 H); 7.58 (ddd, 1 H); 7.67 (ddd, 1 H); 8.12 (s, 1 H); 8.93 (s, 1 H). | 20 |
| 39 | thiophen-2-yl-C(O)- | 513.1 | 1.79–1.91 (m, 2 H); 2.12–2.23 (m, 2 H); 3.57–3.69 (m, 2 H); 3.95–4.07 (m, 2 H); 4.04 (s, 3 H); 4.99 (bs, 1 H); 7.14 (dd, 1 H); 7.41 (ddd, 1 H); 7.47 (dd, 1 H); 7.50 (s, 1 H); 7.58 (ddd, 1 H); 7.68 (ddd, 1 H); 7.76 (dd, 1 H); 8.12 (s, 1 H); 8.92 (s, 1 H). | 11 |

-continued

| Example Compound No. | R | NMR MH+ δ en ppm (DMSO + TFAd) | Yield |
|---|---|---|---|
| 40 | 2-acetylfuran | 497.1 1.77–1.90 (m, 2 H); 2.11–2.21 (m, 2 H); 3.54–3.74 (m, 2 H); 3.94–4.08 (m, 2 H); 4.03 (s, 3 H); 4.99 (bs, 1 H); 6.64 (dd, 1 H); 7.04 (d, 1 H); 7.41 (dd, 1 H); 7.49 (s, 1 H); 7.58 (ddd, 1 H); 7.68 (ddd, 1 H); 7.84 (s, 1 H); 8.11 (s, 1 H); 8.92 (s, 1 H). | 5 |
| 41 | 4-acetylquinoline | 558.2 1.59–1.70 (m, 0.5 H); 1.81–1.97 (m, 1 H); 1.98–2.13 (m, 1.5 H); 2.28–2.40 9 m, 1 H); 3.20–3.34 (m, 1 H); 3.37–3.48 (m, 1 H); 3.68–3.76 (m, 0.5 H); 3.77–3.85 (m, 0.5 H); 4.01 (s, 1.5 H); 4.04 (1.5 H); 4.14–4.22 (m, 0.5 H); 4.23–4.32 (m, 0.5); 5.01 (bs, 1 H); 7.40 (dd, 1 H); 7.50–7.61 (m, 2 H); 7.64–7.70 (dd, 1 H); 7.99-8.06(m, 1 H); 8.10-8.26(m, 4 H); 8.36 (d, 1 H);8.91(s, 1 H); 8.45(s, 0.5 H); 8.46(s, 0.5 H). | |
| 42 | 3-acetylfuran | 497.1 1.74–1.88 (m, 2 H); 2.08–2.20 (m, 2 H); 3.48–3.59 (m, 2 H); 3.84–4.06 (m, 2 H); 4.03 (s, 3 H); 4.97 (bs, 1 H); 6.71 (s, 1 H); 7.41 (dd, 1 H); 7.51 (s, 1 H); 7.58 (ddd, 1 H); 7.67 (ddd, 1 H); 7.74 (s, 1 H); 8.07 (s, 1 H); 8.17 (s, 1 H); 8.91 (s, 1 H). | 89 |
| 43 | 5-bromo-2-acetylfuran | 577.1 1.79–1.91 (m, 2 H); 2.12–2.22 (m, 2 H); 3.53–3.74 (m, 2 H); 3.95–4.05 (m, 2 H); 4.03 (m, 3 H); 4.99 (bs, 1 H); 6.77 (d, 1 H); 7.08 (d, 1 H); 7.41 (dd, 1 H); 7.50 (s, 1 H); 7.58 (ddd, 1 H); 7.68 (ddd, 1 H); 8.12 (s, 1 H); 8.92 (s, 1 H). | 48 |
| 44 | 3-acetylthiophene | 513.1 1.77–1.90 (m, 2 H); 2.06–2.21 (m, 2 H); 3.44–3.64 (3, 2 H); 3.65–4.11 (m, 2 H); 4.06 (s, 3 H); 4.92 (bs, 1 H); 7.27 (dd, 1 H); 7.37 (s, 1 H); 7.41 (dd, 1 H); 7.59 (ddd, 1 H); 7.62 (dd, 1 H); 7.69 (ddd, 1 H); 7.83 (dd, | 47 |
| 45 | 2-acetylbenzofuran | 547.1 1.80–1.93 (m, 2 H); 2.14–2.24 (m, 2 H); 3.54–3.84 (m, 2 H); 3.97–4.10 (m, 2 H); 4.01 (s, 3 H); 5.00 (bs, 1 H); 7.32 (dd, 1 H); 7.37 (dd, 1 H); 7.41 (s, 1 H); 7.43 (dd, 1 H); 7.48 (s, 1 H); 7.55 (ddd, 1 H); 7.61–7.66 (m, 2 H); 7.73 (d, 1 H); 8.09 (s, 1 H); 8.89 (s, 1 H). | 53 |

-continued

| Example Compound No. | R | MH+ | NMR δ en ppm (DMSO + TFAd) | Yield |
|---|---|---|---|---|
| 46 | quinoline-3-yl-C(=O)- | 558.2 | 1.88–2.01 (m, 2 H); 2.06–2.33 (m, 2 H); 3.46 (3.85 (m, 3 H); 4.04 (s, 3 H); 4.09–4.22 (m, 1 H); 5.05 (bs, 1 H); 7.41 (dd, 1 H); 7.56 (s, 1 H); 7.58 (dd, 1 H); 7.68 (ddd, 1 H); 7.97 (s, 1 H); 8.14 (s, 1 H); 8.16 (dd, 1 H); 8.30 (d, 1 H); 8.37 (d, 1 H); 8.92 (s, 1 H); 9.20 (s, 1 H); 9.44 (d, 1 H). | 42 |
| 47 | 1H-indol-3-yl-C(=O)- | 546.2 | 1.80–1.89 (m, 2 H); 2.14–2.22 (m, 2 H); 3.54–3.63 (m, 2 H); 4.02–4.11 (m, 2 H); 4.04 (s, 3 H); 4.98 (bs, 1 H); 7.14 (dd, 1 H); 7.19 (dd, 1 H); 7.40 (dd, 1 H); 7.48 (d, 1 H); 7.50 (s, 1 H); 7.58 (dd, 1 H); 7.67 (ddd, 1 H); 7.73 (d, 1 H); 7.76 (s, 1 H); 8.13 (s, 1 H); 8.92 (s, 1 H). | 15 |
| 48 | thiophen-3-yl-CH2-C(=O)- | 527.1 | 1.55–1.71 (m, 2 H); 1.93–2.09 (m, 2 H); 3.29–3.40 (m, 1 H); 3.41–3.50 (m, 1 H); 3.73–3.85 (m, 1 H); 3.75 (d, 1 H); 3.80 (d, 1 H); 3.89–3.99 (m, 1 H); 4.00 (s, 3 H); 4.88 (bs, 1 H); 7.02 (d, 1 H); 7.28 (d, 1 H); 7.39 (dd, 1 H); 7.44 (s, 1 H); 7.48 (dd, 1 H); 7.52–7.59 (m, 2 H); 7.60–7.68 (m, 2 H); 8.09 (s, 1 H); 8.90 (s, 1 H). | 43 |
| 49 | 3-chloro-benzothiophen-2-yl-C(=O)- | 597.1 | 1.80–1.94 (m, 2 H); 2.08–2.30 9 m, 2 H); 3.34–3.58 (m, 1 H); 3.60–3.79 (m, 2 H); 3.99–4.13 (m, 1 H); 4.03 (s, 3 H); 5.01 (bs, 1 H); 7.40 (dd, 1 H); 7.49 (s, 1 H); 7.55–7.63 (m, 3 H); 7.67 (dd, 1 H); 7.89 (dd, 1 H); 8.12 (s, 1 H); 8.13 (d, 1 H); 8.81 (s, 1 H). | 27 |
| 50 | 5-chloro-1H-indol-2-yl-C(=O)- | 580.2 | 1.82–1.95 (m, 2 H); 2.16–2.26 (m, 2 H): 3.63–3.83 (m, 2 H); 4.04 (s, 3 H); 4.08–4.19 (m, 2 H); 5.03 (bs, 1 H); 6.94 (s, 1 H); 7.21 (dd, 1 H); 7.41 (dd, 1 H); 7.47 (d, 1 H); 7.51 (s, 1 H); 7.58 (ddd, 1 H); 7.65–7.70 (m, 2 H); 8.13 (s, 1 H); 8.92 (s, 1 H). | 31 |
| 51 | 5-bromo-thiophen-2-yl-C(=O)- | 593.1 | 1.81–1.92 (m,2 H);2.11–2.22 (m, 2 H); 3.57–3.69 (m, 2 H); 3.93–4.04 (m, 2 H); 4.03 (s, 3 H); 4.99 (bs, 1 H); 7.26 (d, 1 H); 7.33 (d, 1 H); 7.41 (dd, 1 H); 7.50 (s, 1 H); 7.58 (dd, 1 H); 7.68 (ddd, 1 H); 8.12 (s, 1 H); 8.92 (s, 1 H). | 35 |

-continued

| Example Compound No. | R | MH+ | NMR δ en ppm (DMSO + TFAd) | Yield |
|---|---|---|---|---|
| 52 | 2,6-dichloropyridin-4-yl ketone | 578.1 | 1.80–1.94 (m, 2 H); 2.03–2.12 (m, 1 H); 2.13–2.22 (m, 1 H); 3.28–3.38 (m, 1 H); 3.45–3.65 (m, 2 H); 3.96–4.03 (m, 1 H); 4.03 (s, 3 H); 4.98 (bs, 1 H); 7.41 (dd, 1 H); 7.50 (s, 1 H); 7.58 (ddd, 1 H); 7368 (ddd, 1 H); 7.72 (s, 2 H); 8.11 (s, 1 H); 8.91 (s, 1 H). | 41 |
| 53 | 5-methylthiophen-2-yl ketone | 527.2 | 1.78–1.88 (m, 2 H); 2.11–2.21 (m, 2 H); 2.48 (s, 3 H); 3.56–3.67 (m, 2 H); 3.96–4.06 (m, 2 H); 4.03 (s, 3 H); 4.98 (bs, 1 H); 6.84 (d, 1 H); 7.27 (d, 1 H); 7.40 (dd, 1 H); 7.49 (s, 1 H); 7.58 (dd, 1 H); 7.68 (ddd, 1 H); 7.12 (s, 1 H); 7.92 (s, 1 H). | 21 |
| 54 | 1-methylpyrrol-2-yl ketone | 510.2 | 1.77–1.88 (m, 2 H); 2.11–2.21 (m, 2 H); 3.51–3.62 (m, 2 H); 3.71 (s, 3 H); 3.99–4.09 (m, 2 H); 4.03 (s, 3 H); 4.97 (bs, 1 H); 6.06 (dd, 1 H); 6.38 (dd, 1 H); 6.90 (bs, 1 H); 7.41 (dds, 1 H); 7.50 (s, 1 H); 7.58 (ddd, 1 H); 7.67 (ddd, 1 H); 8.12 (s, 1 H); 8.92 (s, 1 H). | 34 |
| 55 | 1-methylindol-2-yl ketone | 560.2 | 1.82–1.93 (m, 2 H); 2.11–2.27 (m, 2 H); 3.58–3.69 (m, 2 H); (s, 3 H); 3.93–4.16 (m, 2 H); 4.04 (s, 3 H); 5.02 (bs, 1 H); 6.74 (s, 1 H); 7.12 (dd, 1 H); 7.27 (dd, 1 H); 7.41 (dd, 1 H); 7.51 (s, 1 H); 7.53 (d, 1 H); 7.58 (dd, 1 H); 7.63 (d, 1 H); 7.67 (dd, 1 H); 8.12 (s, 1 H); 8.92 (s, 1 H). | 34 |
| 56 | 2-chloropyridin-4-yl ketone | 542.1 | 1.80–1.95 (m, 2 H); 2.03–2.13 (m, 1 H); 2.14–2.25 (m, 1 H); 3.29–3.39 (m, 1 H); 3.48–3.65 (m, 2 H); 3.97–4.07 (m, 1 H); 4.03 (s, 3 H); 4.99 (bs, 1 H); 7.41 (dd, 1 H); 7.50 (bs, 2 H); 7.58 (ddd, 1 H); 7.64 (s, 1 H); 7.67 (dd, 1 H); 8.12 (s, 1 H); 8.53 (d, 1 H); 8.92 (s, 1 H). | 20 |
| 57 | 4-nitropyrazol-1-yl acetone | 556.2 | 1.69–1.79 (m, 1 H); 1.85–1.95 (m, 1 H); 2.06–2.24 (m, 2 H); 3.37–3.46 (m, 1 H); 3.46–3.56 (m, 1 H); 3.76–3.85 (m, 1 H); 3.86–3.95 (m, 1 H); 4.03 (s, 3 H); 4.98 (bs, 1 H); 5.36 (s, 2 H); 7.41 (ddd, 1 H); 7.52 (s, 1 H); 7.58 (ddd, 1 H); 7.68 (ddd, 1 H); 8.12 (s, 1 H); 8.27 (s, 1 H); 8.80 (s, 1 H); 8.27 (s, 1 H); 8.80 (s, 1 H); 8.92 (s, 1 H). | 10 |

-continued

| Example Compound No. | R | NMR MH+ δ en ppm (DMSO + TFAd) | Yield |
|---|---|---|---|
| 58 | ![R group: O2N-pyrazole-C(=O)-] | 542.1 1.83–1.99 (m, 2 H); 2.15–2.24 (m, 2 H); 3.61–3.75 (m, 2 H); 3.98–4.07 (m, 2 H); 4.04 (s, 3 H); 5.03 (bs, 1 H); 7.40 (dd, 1 H); 7.42 (s, 1 H); 7.52 (s, 1 H); 7.58 (dd, 1 H); 7.67 (dd, 1 H); 8.14 (s, 1 H); 8.93 (s, 1 H). | 21 |

EXAMPLES 59 TO 85

Preparation of Compound Numbers 59 to 85 of Table III

Generic Process

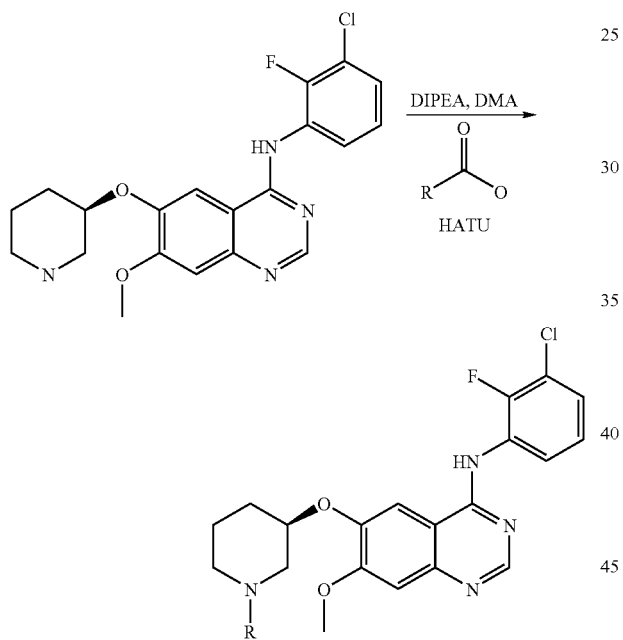

Solid HATU (119 mg, 0.815 mmol) and DIPEA (0.171 ml, 0.96 mmol) were dissolved in anhydrous DMA (0.5 ml) were added to a solution of N-(3-chloro-2-fluorophenyl)-7-methoxy-6-[(3R)-piperidin-3-yloxy]-quinazolin-4-yl-amine dihydrochloride (100 mg, 0.24 mmol), and the carboxylic acid (0.36 mmol) in DMA (0.5 ml) at room temperature. The resulting solution was allowed to stir at room temperature overnight. The crude reaction mixtures were purified using mass-triggered preparative LCMS.

The fractions containing the desired compound were evaporated in a Genevac and the residue taken up in 10% (v/v) MeOH in DCM (0.4 ml), diluted with 6 ml of 15% (v/v) Et$_2$O in pentane and left at 4° C. overnight. The resulting precipitates were collected by filtration and dried to a constant weight to afford the desired amides as amorphous or crystalline solids.

Standard Conditions for Purification by Mass-Triggered Preparative LCMS

Column: ThermoHypersil Keystone B-Basic 5μ 21 mm×100 mm

Eluant: 7.5 minutes Gradient from 20% to 95% of acetonitrile in water (buffer 2 g/l of (NH$_4$)$_2$CO$_3$, pH 8.9).

Flow rate: 25 ml/min.

Preparation of Starting Material

N-(3-chloro-2-fluorophenyl)-7-methoxy-6-[(3R)-piperidin-3-yloxy]quinazoline hydrochloride

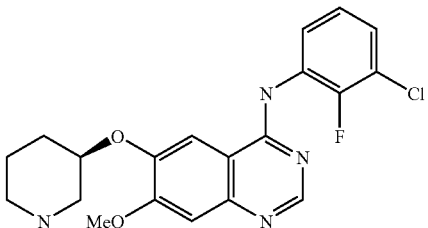

HCl (1.77 ml, 4M solution in dioxane) was added to 4-chloro-7-methoxy-6-[(3R)-1-tert-butoxycarbonyl)piperidin-3-yloxy]quinazoline (1.77 g) and 3-chloro-2-fluoroaniline (0.69 g) dissolved in acetonitrile (70 ml). The mixture was heated to 70° C. overnight. HCl (1.77 ml, 4M solution in dioxane) was then added and the mixture heated a further 1.5 hours. The reaction mixture was cooled and the resulting precipitate collected by filtration to give 4-(3-chloro-2-fluoroanilino)-7-methoxy-6-[(3R)-piperidin-3-yloxy]quinazoline hydrochloride as a white solid (1.814 g, 92%); $^1$H NMR Spectrum: (DMSOd$_6$) 1.70-1.95 (m, 2H), 1.95-2.10 (m, 1H); 2.10-2.25 (m, 1H), 2.95-3.10 (m, 1H), 3.10-3.65 (m, 3H+ H$_2$O); 4.03 (s, 3H); 4.95-5.10 (m, 1H); 7.35 (m, 1M); 7.47 (s, 1H); 7.53 (m, 1H); 7.64 (m, 1H), 8.84 (s, 2H); 9.10 (bs, 2H); 12.10 (bs, 1H); Mass Spectrum: (M+H): 403.

The 4-chloro-7-methoxy-6-[(3R)-1-(tert-butoxycarbonyl)piperidin-3-yloxy]quinazoline starting material was prepared as follows:

Diethyl azodicarboxylate (5.7 ml) was added to 4-chloro-6-hydroxy-7-methoxyquinazoline (4.39 g; prepared as described in Example 1 (Preparation of starting materials)), triphenylphosphine (8.2 g) and (3S)-1-(tert-butoxycarbonyl)-3-hydroxypiperidine (Commercially Available—CAS Registry No 14390044-1) (6.29 g) in dichloromethane (130 ml) and the reaction mixture was stirred at 40° C. for 6 hours.

This was allowed to stand overnight at −18° C. then filtered. The filtrates were purified by flash column chromatography eluting with acetone/isohexane/triethylamine (17/82/1) to give 4-chloro-7-methoxy-6-[(3R)-1-(tert- butoxycarbonyl) piperidin- 3-yloxy)]quinazoline as a white solid (0.794 g, 48%); Mass Spectrum: (M+H)+394.

| Example/ Compound No. | R | NMR MH+ δ en ppm(DMSO + TFAd) | Yield |
|---|---|---|---|
| 59 | (3-pyridyl-C(O)CH2-) | 508.1 1.53-1.72(m, 1H); 1.76-1.96(m, 1H); 1.97-2.09(m, 1H); 2.11-2.23(m, 1H); 3.18-3.29(m, 0.7H); 3.38-3.53(m, 0.6H); 3.65-3.73 (m, 0.7H); 3.74-3.81(m, 0.3H); 3.84-3.93(m, 0.7H); 4.06(s, 2.1H); 3.12(s, 0.9H); 4.23-4.32(m, 0.3H); 4.33-4.42(m, 0.7H); 4.75 (bs, 7H); 4.91(bs, 0.3H); 7.37-7.45(m, 2H); 7.56(dd. 0.7H); 7.61(dd, 0.3H); 7.94 (s, 0.7H); 8.01(dd, 0.7H); 8.1 dd, 0.3H); 8.26(s, 0.3H); 8.53(d, 0.7H); 8.61 (d, 0.7H); 8.88-8.96(m, 1.6H); 8.99(s, 0.3H) 9.04 (bs, 1H) | 48 |
| 60 | (2-thienyl-CH2-C(O)-) | 527.1 1.50-1.62(m, 1H); 1.73-2.03(m, 2H); 2.07-2.19(m, 1H); 3.43-4.08(m, 6H); 4.03(s, 3H); 4.72(bs, 1H); 6.81(d, 0.5H); 6.88(dd, 0.5H); 6.95-7.01(m, 1H); 7.30(d, 0.5H); 7.33-2.46 (m, 2.5H); 7.54-7.60(m, 1H); 7.64-7.7 1(m, 1H); 8.13(s, 0.5H); 8.17(s, 0.5H); 8.92(s, 0.5H); 8.93 (s, 0.5H). | 33 |
| 61 | (2-pyridyl-C(O)CH2-) | 508.1 | 43 |
| 62 | (4-pyridyl-C(O)CH2-) | 508.1 1.50-1.60(m, 0.4H); 1.63-1.72(m, 0.6H); 1.74-1.94 (m, 1H); 1.97-2.23(m, 2H); 3.17-3.28(m, 0.6H); 3.30-3.39(m, 1H); 3.61-3.78(m, 1.4H); 4.08(s, 1.2H); 4.14 (s, 1.8H); 4.38(d, 1H); 4.75 (bs, 0.6H); 4.95(bs, 0.4H); 7.35-7.46(m, 2H); 7.56(dd, 0.6H); 7.62(dd, 0.4H); 7.68 (dd, 1H); 7.96(s, 0.6H); 8.03(d, 0.8H); 8.11(d, 1.2H); 8.26(s, 0.4H); 8.93 (s, 0.6H); 8.94(d, 0.4H); 8.98(d, 1.2H); 8.10(d, 0.8H). | 48 |

-continued

| Example/ Compound No. | R | MH+ | NMR δ en ppm(DMSO + TFAd) | Yield |
|---|---|---|---|---|
| 63 | 2-amino-pyridin-3-yl C(=O)CH group | 523.2 | 1.52-1.72(m, 1H); 1.78-1.92 (m, 1H): 1.97-2.24(m, 2H); 3.12-4.01(m, 3H); 4.08(s, 3H); 4.18-4.39(m, 1H); 4.72(m, 0.6H); 4.92(m, 0.4H); 6.71(bs, 0.6H); 7.05 (bs, 0.4H); 7.37(bs, 1H); 7.41(dd, 1H); 7.57(bs, 1H); 7.68(ddd, 1H); 7.83-7.97 (m, 2H); 8.12(bs, 0.6H); 8.24(bs, 0.4H); 8.92(s, 1H). | 57 |
| 64 | pyrrol-2-yl C(=O)CH group | 496.1 | 1.59-1.70(m, 1H); 1.88-2.00(m, 2H); 2.14-2.24(m, 1H); 3.65-3.85(m, 2H); 4.00(s, 3H); 4.02-4.09(m, 2H); 4.74(bs, 1H); 6.04(bs, 1H); 6.49(bs, 1H); 6.82(bs, 1H); 7.32(s, 1H); 7.41(ddd, 1H); 7.58(ddd, 1H); 7.68 (ddd, 1H); 8.14(s, 1H); 8.91 (s, 1H). | 31 |
| 65 | thien-2-yl C(=O)CH group | 513.1 | 1.58-1.69(m, 1H); 1.86-2.21(m, 3H); 3.42-3.71(m, 1H); 3.80-4.01(m, 2H); 4.02(s, 3H); 4.02-4.25(m, 1H); 4.78(bs, 1H); 7.04(bs, 1H); 7.33(s, 1H); 7.37-7.45 (m, 2H); 7.58(dd, 1H); 7.64 (bs, 1H); 7.68(ddd, 1H); 8.09(bs, 1H); 8.91(s, 1H). | 46 |
| 66 | furan-2-yl C(=O)CH group | 497.1 | 1.59-1.70(m, 1H); 1.87-2.05(m, 2H); 2.10-2.23(m, 1H); 3.37-3.62(m, 1H); 3.77-3.72(m, 1H); 3.96(d, 1H); 3.99(s, 3H); 4.05-4.35 (m, 1H); 4.77(bs, 1H); 6.31-6.75(bs, 1H); 6.93(bs, 1H); 7.32(s, 1H); 7.41(dd, 1H); 7.44-7.82(bs, 1H); 7.58(dd, 1H); 7.68(ddd, 1H); 8.10(bs, 1H); 8.92(s, 1H). | 48 |
| 67 | furan-3-yl C(=O)CH group | 497.1 | 1.55-1.66(m, 1H); 1.73-2.28(m, 3H); 3.23-3.43(m, 1H); 3.51-4.17(m, 3H); 4.03(s, 3H); 4.75(bs, 1H); 6.63(s, 1H); 7.35(s, 1H); 7.41(ddd, 1H); 6.46-6.83 (m, 1H); 7.58(dd, 1H); 7.68 (ddd,, 1H); 7.86-8.31(m, 2H); 8.92(s, 1H). | 45 |
| 68 | 5-bromo-furan-2-yl C(=O)CH group | 577.1 | 1.58-1.70(m, 1H); 1.88-2.22(m, 3H); 3.16-3.45(m, 1H); 3.88(dd, 1H); 3.92-4.11(m, 1H); 3.98(s, 3H); 4.29-4.54(m, 1H); 4.78(bs, 1H); 6.38-6.61(bs, 1H); 6.95 (bs, 1H); 7.29(bs, 1H); 7.41 (dd, 1H); 7.58(dd, 1H); 7.68(dd, 1H); 8.08(bs, 1H); 8.91(s, 1H). | 55 |

-continued

| Example/ Compound No. | R | MH+ | NMR δ en ppm(DMSO + TFAd) | Yield |
|---|---|---|---|---|
| 69 | thiophen-3-yl ketone | 513.1 | 1.55-1.68(m, 1H); 1.82-2.22(m, 3H); 3.18-4.25(m, 4H); 4.05(s, 3H); 4.65-4.87 (m, 1H); 7.05-7.25(bs, 1H); 7.34(bs, 2H); 7.41(dd, 1H); 7.58(bs, 1H); 7.62-7.77(bs, 1H); 7.68(dd, 1H); 7.81(bs, 0.6H); 8.23(bs, 0.4H); 8.92 (s, 1H). | 20 |
| 70 | benzofuran-2-yl ketone | 547.2 | 1.62-1.72(m, 1H); 1.95-2.18(m, 3H); 3.12-3.25(m, 1H); 3.73-3.87(m, 1H); 4.01(s, 3H): 4.28-4.40(m, 1H); 4.74(1,s, 1H); 4.83-4.95(m, 1H); 6.95-7.82(m, 10H); 8.71(bs, 1H). | 52 |
| 71 | benzothiophen-2-yl ketone | 563.1 | 1.63-1.73(m, 1H): 1.90-2.29(m, 3H); 3.15-3.42(m, 0.6H); 3.70-3.90(m, 1.4H); 4.00-4.10(m, 1H); 4.02(s, 3H); 4.22-4.44(m, 0.6): 4.534.93(m, 1.4H); 7.08-8.03(m, 10H); 8.66-8.96 (bs, 1H). | 52 |
| 72 | quinolin-3-yl ketone | 558.2 | 1.54-1.77(m, 1H); 1.89-2.24(m, 3H); 3.17-.30(m, 0.7H); 3.47-3.57(m, 0.3H); 3.57-3.63(m, 0.3H); 3.71 (d, 0.7H); 3.86(d, 0.3H); 4.05-4.13(m, 0.7H); 4.16(s, 3H); 4.24-4.33(m, 0.3H); 4.45-4.55(m, 0.7H); 4.67 (m, 0.7H); 4.92(0.3H); 7.28-8.42(m, 9H); 1.4H); 8.95(bs, 0.6H); 8.22 (s, 0.7H); 8.25(s, 0.3H). | 53 |
| 73 | 1H-indol-3-yl ketone | 546.2 | 1.59-1.68(m, 1H); 1.91-2.04(m, 2H); 2.11-2.20(m, 1H); 3.47-3.58(m, 1H); 3.84-3.97(m, 2H); 4.02(s, 4.73(bs, 1H); 7.06-7.15(m, 2H); 7.23(bs, 1H): 7.33(d, 1H); 7.41(dd, 1H); 7.58 (dd, 1H); 7.61(s, 1H); 7.64-7.70(m, 2H); 7.94-8.04(m, 1H); 8.89(s, 1H). | 35 |
| 74 | thiophen-3-yl acetone | 527.2 | 1.42-1.58(m, 1H); 1.68-1.82(m, 1H); 1.85-1.97(m, 1H); 2.02-2.15(m, 1H); 3.42-3.52(m, 1H); 3.54-3.71(m, 2.5H); 3.71-3.89 (m, 1.9H); 4.04(s, 1.2H); 4.06(s, 1.8H); 4.10(dd, 0.6H); 4.64(bs, 0.4H); 4.73 (bs, 0.6H); 6.93(d, 0.4H); 7.02(d, 0.6H); 7.15(d, 0.4H); 7.30(d, 0.6H); 7.35 (s, 0.4H); 7.36(s, 0.6H); 7.37-7.44(m, 1.4H); 7.50 (dd, 0.6H); 7.56-7.63(m, 1H); 7.66-7.72(m, 1H); 8.10(s, 0.4H); 8.14(s, 0.6H);nl8.91(s, 0.6H); 8.92(s, 0.4H). | 17 |

-continued

| Example/ Compound No. | R | MH+ | NMR δ en ppm(DMSO + TFAd) | Yield |
|---|---|---|---|---|
| 75 | 3-chlorobenzothiophene-2-carbonyl | 597.2 | 1.52-1.75(m, 1H); 1.88-2.19(m, 3H); 3.20-3.32(m, 0.6H); 3.39-3.50(m, 0.4H); 3.51-3.62(m, 0.4H); 3.67-3.79(m, 1H); 4.08(s, 3H); 4.17-4.25(m, 0.6H); 4.32-4.43(m, 1H); 4.64(bs, 0.6H); 4.91(bs, 0.4H); 7.22-7.46(m, 4H); 7.54-7.73(m, 3.2H); 7.72-7.81(bs, 0.6H); 7.81-7.84(bs, 0.4H); 8.09-8.16(bs, 0.4H); 8.20-8.26(bs, 0.4H); 8.75(bs, 0.6H); 8.92(bs, 0.4H). | 13 |
| 76 | 5-chloro-1H-indole-2-carbonyl | 580.2 | 1.62-1.72(m, 1H); 1.94-2.22(m, 3H); 3.02-5.04(m, 5H); 4.01(s, 3H); 6.29-7.90(m, 9H); 8.80(s, 1H). | 33 |
| 77 | 5-bromothiophene-2-carbonyl | 593.1 | 1.58-1.69(m, 1H); 1.85-1.97(m, 1H); (1.98-2.18(m, 2H); 3.22-3.61(bs, 1H); 3.81(d, 1H); 3.96-4.14(bs, 1H); 4.02(s, 3H); 4.14439(m, 1H); 4.76(bs, 1H); 7.02-7.20(bs, 1H); 7.24(d, 1H); 7.33(s, 1H); 7.41(dd, 1H); 7.58(dd, 1H); 7.69(dd, 1H); 7.92-8.13(bs, 1H); 8.92(s, 1H). | 43 |
| 78 | 2,6-dichloropyridine-4-carbonyl | 576.1 | 1.50-1.58(m, 0.3H); 1.62-1.70(m, 0.7H); 1.75-1.90(m, 1H); 1.92-2.23(m, 2H); 3.08(dd, 0.7H); 3.29-3.36(m, 0.3H); 3.37-3.44(m, 0.3H); 3.54-3.64(m, 1H); 3.90(d, 0.7H); 4.09(s, 2.1H); 4.14(s, 0.9H); 4.35(dd, 0.3H); 4.43(d, 0.7H); 4.75(bs, 0.7H); 4.92(bs, 0.3H); 7.37-7.45(m, 2H); 7.50-7.58(m, 2.7H); 7.61(dd, 0.3H); 7.68(ddd, 1H); 7.87(s, 0.7H); 8.23(s, 0.3H); 8.93(s, 1H). | 37 |
| 79 | 5-methylthiophene-2-carbonyl | 527.2 | 1.56-1.67(m, 1H); 1.85-2.05(m, 2H); 2.07-2.20(m, 1H): 2.37(bs, 3H); 3.40-3.70(m, 1H); 3.81-3.96(m, 2H); 4.01(s, 3H); 4.03-4.23(m, 1H); 4.75(bs, 1H); 6.61-6.77(bs, 1H); 7.19(bs, 1H); 7.32(bs, 1H); 7.41(dd, 1H); 7.58(dd, 1H); 7.69(ddd, 1H); 8.07(bs, 1H): 8.91(s, 1H). | 35 |
| 80 | 1-methyl-1H-pyrrole-2-carbonyl | 510.1 | 1.56-1.66(m, 1H); 1.83-1.94(m, 1H); 1.95-2.05(m, 1H); 2.06-2.17(m, 1H); 3.43-3.56(m, 1H); 3.62(s, 3H); 3.79-3.86(m, 1H); 3.85-3.95(m, 1H); 4.01(s, 3H); 4.13-4.24(m, 1H); 4.76(bs, 1H); 5.96(bs, 1H); 6.34(da, 1H); 6.78(bs, 1H); 7.34(s, 1H); 7.41(dd, 1H); 7.58(dd, 1H); 7.68(ddd, 1H); 8.10(bs, 1H); 8.91(s, 1H). | 59 |

-continued

| Example/ Compound No. | R | MH+ | NMR δ en ppm(DMSO + TFAd) | Yield |
|---|---|---|---|---|
| 81 | 1-methylindol-2-yl-C(=O)- | 560.1 | 1.58-1.69(m, 1H); 1.86-1.98(m, 1H); 2.00-2.13(m, 2H); 3.17-3.40(m, 1H); 3.57-3.74(m, 4H); 4.03(s, 3H); 4.15-4.39(m, 1H); 4.40-4.51(m, 1H); 4.59-4.85(m, 1H): 6.53(bs, 1H); 6.76-7.76(m, 9H); 8.79(bs, 1H). | 52 |
| 82 | 2-chloropyridin-4-yl-C(=O)- | 542.1 | 1.49-1.58(0.3H); 1.61-1.71(m, 0.7H); 1.78-1.91(m, 1H); 1.94-2.21(m, 2H); 3.06-3.15(m, 0.7H); 3.28-3.42(m, 0.6H); 3.53-3.66(m, 1H); 3.84-3.93(m, 0.7H); 4.08(s, 0.9H); 4.13(s, 2.1H); 4.31-4.44(m, 1H); 4.73(bs, 0.7H); 4.91(bs, 0.3H); 7.34-7.45(m, 3.7H); 7.48(s, 0.3H); 7.54(dd, 0.7H); 7.61(dd, 0.3H); 7.68(ddd, 1H); 7.85(s, 0.7H); 8.23(s, 0.3H); 8.33(d, 0.7H); 8.56(d, 0.3H); 8.92(s, 1H). | 23 |
| 83 | 4-nitropyrazol-1-yl-CH2-C(=O)- | 556.1 | 1.49-1.81(1.6H); 1.84-2.23(m, 2.4H); 3.35-3.44(m, 0.6H); 3.54-3.52(m, 1H); 3.75-3.90(m, 2.4H); 4.03(s, 1.2H); 4.09(s, 1.8H); 4.71(bs, 0.4H); 4.81(bs, 0.4H); 5.19-5.47(m, 2H); 7.33(s, 0.4H); 7.39(0.6H); 7.41(dd, 1H); 7.55-7.62(m, 1H); 7.65-7.72(m, 1H); 8.16(s, 1H); 8.24(s, 0.4H);8.26(s, 0.6H); 8.71(s, 0.4H);8.76(s, 0.6H); 8.91(s, 0.4H);8.92(s, 0.6H). | 51 |
| 84 | 3-methylisoxazol-5-yl-CH2-C(=O)- | 526.1 | 1.49-2.17(m, 4H); 2.19(s, 1.5H); 2.22(s, 1.5H); 3.37-3.46(m, 0.5H); 3.54-3.61(m, 1H); 3.71-3.78(m, 1H); 3.82-3.86(m, 1H); 3.86-3.99(m, 1.5H); 4.00-4.08(m, 1H); 4.03(s, 1.5H); 4.05(s, 1.5H); 4.71(bs, 0.5H); 4.76(bs, 0.5H); 6.17(s, 0.5H); 6.20(s, 0.5H); 7.34(s, 0.5H); 7.37(s, 0.5H); 7.38-7.45(m, 1H); 7.54-7.62(m, 1H); 7.66-7.72(m, 1H); 8.13(s, 0.5H); 8.15(s, 0.5H); 8.91(s, 0.5H); 8.92(s, 0.5H). | 28 |
| 85 | 3-nitro-1H-pyrazol-5-yl-C(=O)- | 542.1 | 1.64-1.73(m, 1H); 1.83-2.23(m, 3H); 3.18-3.28(m, 0.7H); 3.66-3.92(m, 1.6H); 4.01(bs, 3H); 4.08-4.18(m, 0.3H); 4.27-4.36(m, 0.7H); 4.37-4.45(m, 0.7H); 4.81(bs, 1H); 7.20(s, 0.7H); 7.26(s, 0.7H); 7.32-7.40(m, 0.6H); 7.42(dd, 1H); 7.55(dd, 0.7H); 7.56-7.63(m, 0.3H); 7.68(dd, 1H); 7.98(bs, 0.7H); 8.23(bs, 0.3H); 8.92(s, 1H). | 57 |

EXAMPLES 86 AND 87

Preparation of Compounds 86 and 87 of Table III

Compounds 86 and 88 were prepared as follows:

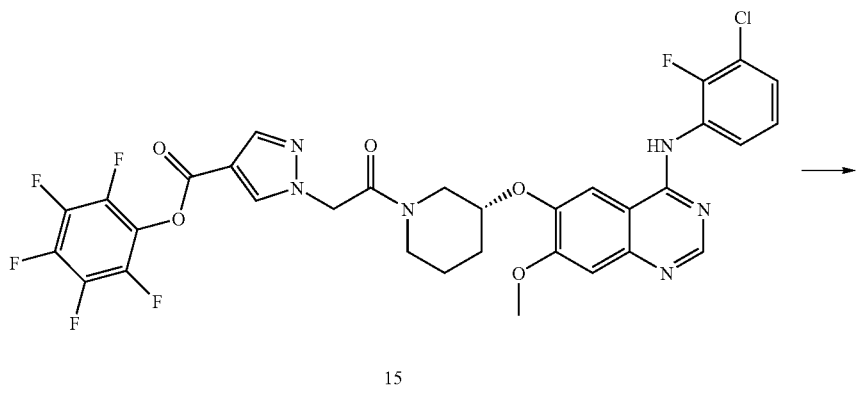

15

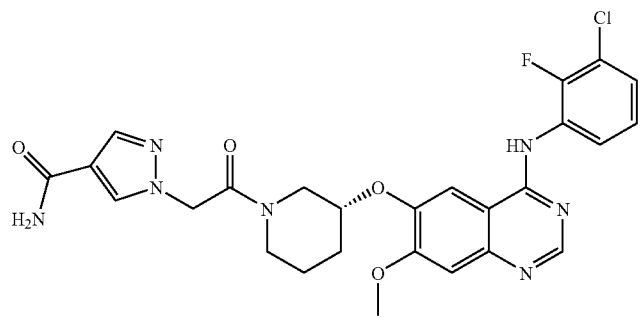

Compound 86, Table III

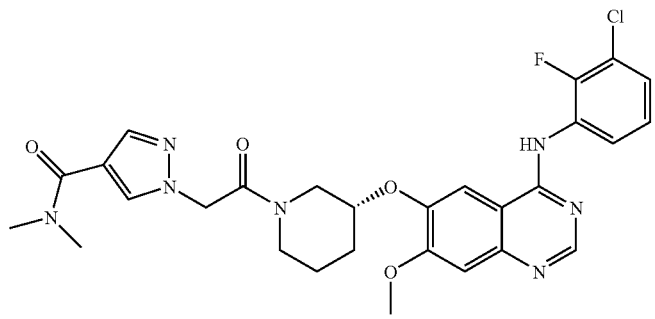

Compound 87, Table III

To a stirred solution of 15 (0.20 g, 0.28 mmol) in DMF (1 ml) at 0° C. was added concentrated aqueous ammonia (1 ml). The reaction mixture was stirred for 10 minutes, concentrated and purified by flash chromatography (elution with a gradient from 100% DCM to 5% 7N $NH_3$-MeOH in DCM) to afford Compound 86 (0.12 g, 77%) as a white solid; $^1$H NMR Spectrum: (DMSO-$d_6$): δ en ppm 1.47-1.82 (m, 2H), 1.91-2.18 (m, 2H), 3.43-3.84 (m, 4H), 3.99 (s, 3H), 4.55 and 4.73 (m, 1H), 5.11-5.33 (m, 2H), 6.99 (br s, 1H), 7.25-7.30 (m, 21H), 7.48-7.56 (m, 2H), 7.79 (s, 1H), 7.91 (m, 1H), 8.01 (s, 1H), 8.39 (s, 1H), 9.63 (s, 1H); Mass Spectrum: (M+H)$^+$ 554.13.

To a stirred solution of 15 (0.20 g, 0.28 mmol) in DMF (1 ml) at 0° C. was added a 2.0 M solution of dimethylamine in tetrahydrofuran (1.4 ml). The reaction mixture was stirred for 1 hour, concentrated and purified by flash chromatography (elution with a gradient from 100% DCM to 5% 7N $NH_3$-MeOH in DCM) to afford Compound 87 (0.042 g, 26%) as a white solid; $^1$H NMR Spectrum: (DMSO-$d_6$): δ en ppm 1.46-1.78 (m, 2H), 1.91-2.21 (m, 2H), 2.89-3.16 (m, 6H), 3.56-3.86 (m, 4H), 3.98 (s, 3H), 4.47 and 4.71 (m, 1H), 5.11-5.32 (m, 2H), 7.27-7.30 (m, 2H), 7.49 (m, 2H), 7.68 (s, 1H), 7.90-7.99 (m, 2H), 8.39 (s, 1H), 9.61 (s, 1H); Mass Spectrum: (M+H)$^+$ 582.20.

Intermediate 15 was prepared as follows:

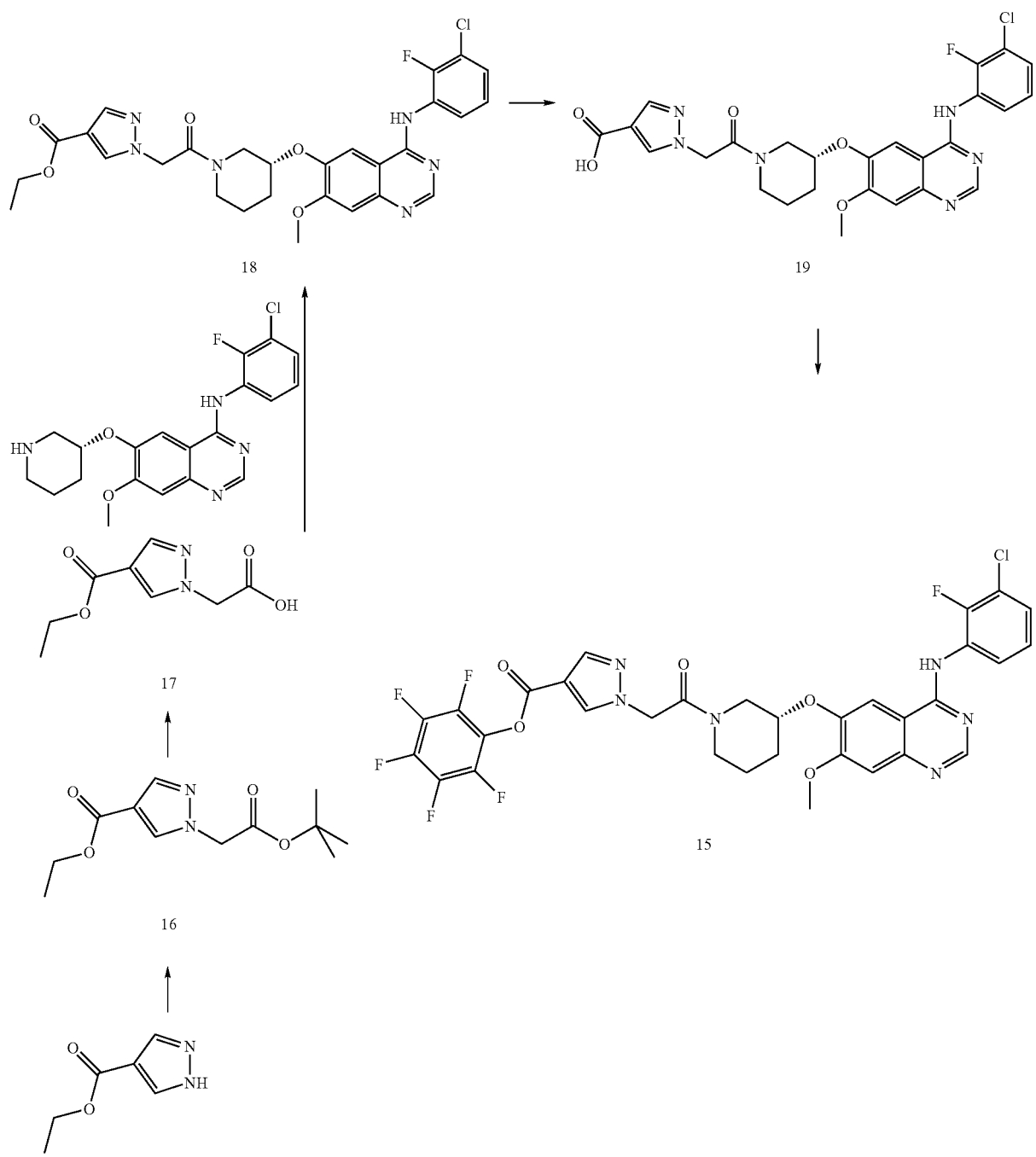

To a stirred suspension of ethyl-1H-pyrazole carboxylate (540 mg, 3.85 mmol) and potassium carbonate (800 mg, 5.78 mmol) in DMF (5 ml) at 0° C., was added tert-butyl bromoacetate (0.63 ml, 4.24 mmol) over a period of 5 minutes. The resulting suspension was stirred for 2 hours at room temperature. The reaction mixture was diluted with diethyl ether (100 ml), washed with water (3×20 ml), dried (MgSO$_4$) and concentrated to afford a beige oil which was purified by flash chromatography on silica gel (elution with pentane-DCM 50/50) to afford 16 (950 mg, 97%) as a colourless oil; $^1$H NMR Spectrum: (CDCl$_3$): δ en ppm 1.35 (t, 3H), 1.47 (s, 9H), 4.30 (q, 2H), 4.81 (s, 2H), 7.95 (s, 1H), 7.97 (s, 1H).

At 0° C., 16 (950 mg, 3.7 mmol) was added to trifluoroacetic acid (10 ml) containing 1 ml of thioanisole. The reaction mixture was allowed to warm to room temperature and stirred for 4 hours, evaporated to dryness and the residue was triturated with pentane (50 ml) and the solid collected by filtration, washed with pentane (2×50 ml) and dried to a constant weight at 40° C. to afford 17 (736 mg, 100%); $^1$H NMR Spectrum: (CDCl$_3$): δ en ppm 1.34 (t, 3H), 4.31 (q, 2H), 4.81 (s, 2H), 5.01 (s, 2H), 7.99 (s, 1H), 8.02 (s, 1H).

To a stirred solution of 17 (950 mg, 3.7 mmol), DIPEA (1.43 g, 11.1 mmol) and N-(3-chloro-2-fluorophenyl)-7-methoxy-6-[(3R)-piperidin-3-yloxy]quinazoline (1.50 g, 3.70 mmol) [prepared as described for examples 59 to 85] in DCM (5 ml) at 0° C., was added solid TBTU (1.78 g, 5.55 mmol) over a period of 5 minutes. The reaction mixture was allowed to warm to room temperature and stirred for 2 hours. The resulting yellow solution was diluted with DCM (50 ml) and washed with 2N NaOH (2×10 ml), dried (MgSO$_4$) and evaporated to dryness to afford 18 (2.1 g, 100%) as a beige foam which was used without further purification; Mass Spectrum: (M+1H)$^+$ 583.13.

To a stirred solution of 18 (2 g, 3.45 mmol) in ethanol (5 ml) was added a 1N solution of NaOH (5.6 ml, 5.6 mmol). The reaction mixture was allowed to warm to room temperature and stirred for 16 hours. The ethanol was removed by evaporation and the pH of aqueous solution decreased to 2 with a 10% w/v solution of potassium hydrogensulfate. The resulting precipitate was taken up in DCM (2 ml) and purified by flash chromatography on silica gel (elution with DCM-MeOH-AcOH 90/9/1) to afford 19 (0.761 g, 40%) as a yellow foam; H NMR Spectrum: (DMSO-d$_6$): δ en ppm 1.45-1.82 (m, 2H), 1.86-2.19 (m, 2H), 3.56-3.86 (m, 4H), 4.01 (s, 3H), 4.56 and 4.71 (m, 1H), 5.10-5.33 (m, 2H), 7.21-7.29 (m, 2H), 7.48-7.53 (m, 2H), 7.70 (s, 1H), 7.93 (s, 1H), 7.98-8.01 (m, 1H), 8.38 (s, 1H); Mass Spectrum: (M+H)$^+$ 555.12.

To a stirred solution of 19 (0.7 g, 1.26 mmol) and pentafluorophenol (0.30 g, 1.64 mol) in DMF (5 ml) at 0° C., was added solid EDCI (0.265 g, 1.39 mmol). The reaction mixture was allowed to warm to room temperature and stirred for 16 hours. The resulting solution was purified by flash chromatography on silica gel (elution with a gradient from 100% pentane to 100% DCM) to afford 15 (0.592 g, 65%) as a white foam, which was used without further purification; Mass Spectrum: (M+H)$^+$ 721.18.

EXAMPLE 88

Preparation of Compound No. 88 of Table III

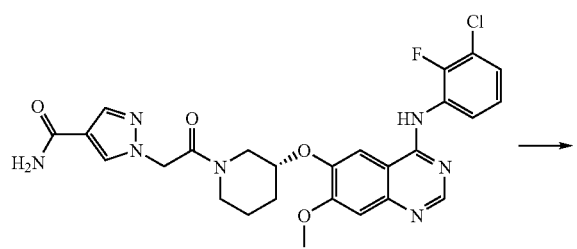

Compound 86, Table III

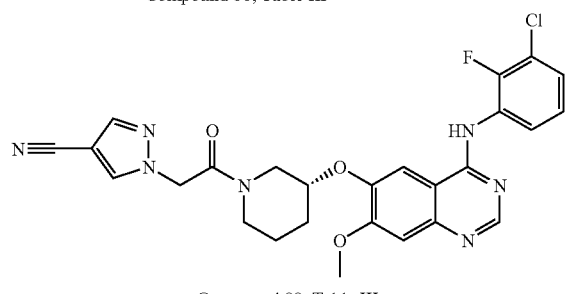

Compound 88, Table III

To a stirred solution of Compound 86 (0.08 g, 0.145 mmol—prepared as described above in Example 86) in tri- ethylamine (0.146 g, 1.45 mmol) at 0° C. was added trifluoroacetic anhydride (0.152 g, 0.725 mmol) over 5 minutes. The resulting solution was allowed to warm to room temperature and stirred for 2 hours. The solution was concentrated and the residue purified by mass-triggered preparative LCMS to afford Compound 87 (0.04 g, 53%) as a white solid; $^1$H NMR Spectrum: (DMSO-d$_6$): δ en ppm 1.53-1.99 (m, 4H), 2.08-2.15 (m, 2H), 3.56-3.96 (m, 2H), 4.01 (s, 3H), 4.47 and 4.74 (m, 1H), 5.20-5.44 (m, 2H), 7.24 (s, 1H), 7.27 (s, 1H), 7.34 (m, 1H), 7.54-7.57 (m, 2H), 7.98 (s, 1H), 8.04 (s, 1H), 8.41 (m, 1H), 8.57 (s, 1H); Mass Spectrum: (M+H)$^+$ 534.15.

EXAMPLE 89

Preparation of Compound No. 89 shown in Table IV
(phenyl 4-({4-[(3-chloro-2-fluorophenyl)amino]-7-methoxyquinazolin-6-yl}oxy)piperidine-1-carboxylate)

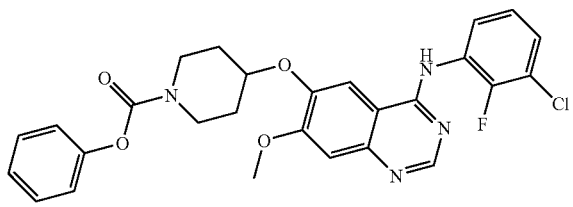

Phenyl chloroformate (43 mg, 0.25 mmol) was added dropwise to a mixture of N-(3-chloro-2-fluorophenyl)-7-methoxy-6-(piperidin-4-yloxy)quinazolin-4-amine (100 mg, 0.25 mmol) [prepared as described in Example 1] and diisopropylethylamine (50 µl, 0.30 mmol) in dichloromethane (2 ml). The mixture was stirred at room temperature for 18 hours. After evaporation of the solvents under vacuum, the residue was diluted in DMF (1 ml) and purified on an HPLC column (C18, 5 microns, 19 mm diameter, 100 mm length) of a preparative HPLC-MS system eluting with a mixture of water and acetonitrile containing 2 g/l of ammonium formate (gradient) to give the title compound as a solid (76 mg, 57%). NMR spectrum (DMSO-d6) 1.81 (m, 2H), 2.11 (m, 2H), 3.39 (m, 1H), 3.58 (m, 1H), 3.79 (m, 1H), 3.90 (m, 1H), 3.96 (s, 3H), 4.78 (m, 1H), 7.15 (d, 2H), 7.23 (m, 2H), 7.30 (m, 1H), 7.39 (m, 2H), 7.50 (m, 2H), 7.91 (s, 1H), 8.38 (s, 1H); Mass spectrum: MH$^+$ 523.

EXAMPLES 90 TO 98

Preparation of Compound Numbers 90 to 98 Shown in Table V

General Procedure:

The corresponding isocyanate (0.3 mmol) was added dropwise to a mixture of N-(3-chloro-2-fluorophenyl)-7-methoxy-6-(piperidin-4-yloxy)quinazolin-4-amine (100 mg, 0.25 mmol) [prepared as described in Example 1] in dichloromethane (2 ml). The mixture was stirred at room temperature for 18 hours. After evaporation of the solvents under vacuum, the residue was diluted in DMF (1 ml) and purified on an HPLC column (C18, 5 microns, 19 mm diameter, 100 mm length) of a preparative HPLC-MS system eluting with a mixture of water and acetonitrile containing 2 g/l of ammonium formate (gradient) to give the following compounds:

Compound 90

(4-({4-[(3-Chloro-2-fluorophenyl)amino]-7-methoxyquinazolin-6-yl}oxy)-N-phenylpiperidine-1-carboxamide)

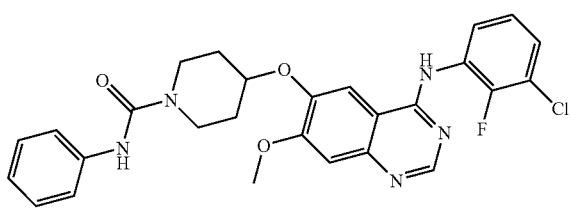

90 mg, 70%; starting isocyanate: phenyl isocyanate.

NMR spectrum (DMSO-d6) 1.72 (m, 2H), 2.06 (m, 2H), 3.39 (m, 2H), 3.86 (m, 2H), 3.95 (s, 3H), 4.75 (m, 1H), 6.93 (m, 1H); 7.30-7.20 (m, 4H), 7.55-7.45 (m, 4H), 7.89 (s, 1H), 7.38 (s, 1H), 8.57 (s, 1H), 9.60 (m, 1H); Mass spectrum: MH+ 522.

Compound 91

(N-Benzyl-4-({4-[(3-chloro-2-fluorophenyl)amino]-7-methoxyquinazolin-6-yl}oxy)piperidine-1-carboxamide)

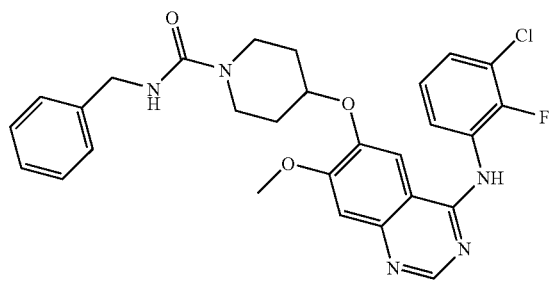

26 mg, 19%; starting isocyanate: benzyl isocyanate.

NMR spectrum (DMSO-d6) 1.63 (m, 2H), 2.01 (m, 2H), 3.22 (m, 2H), 3.78 (m, 2H), 3.94 (s, 3H), 4.26 (d, 2H), 4.72 (m, 1H), 7.30-7.10 (m, 8H), 7.51 (m, 2H), 7.86 (s, 1H), 8.37 (s, 1H); Mass spectrum: MH+ 536

Compound 92

(4-({4-[(3-Chloro-2-fluorophenyl)amino]-7-methoxyquinazolin-6-yl}oxy)-N-[4-(dimethylamino)phenyl]piperidine-1-carboxamide)

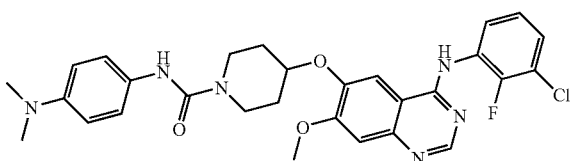

68 mg, 49%; starting isocyanate: 4-dimethylaminophenyl isocyanate.

NMR spectrum (DMSO-d6) 1.70 (m, 2H), 2.06 (m, 2H), 2.82 (s, 6H), 3.30 (m, 2H), 3.85 (m, 2H), 3.95 (s, 3H), 4.75 (m, 1H), 6.66 (d, 2H); 7.24 (m, 3H), 7.30 (m, 1H), 7.52 (m, 2H), 7.89 (s, 1H), 8.27 (s, 1H), 8.38 (s, 1H), 9.60 (s, 1H); Mass spectrum: MH+ 565

Compound 93

(4-({4-[(3-Chloro-2-fluorophenyl)amino]-7-methoxyquinazolin-6-yl}oxy)-N-(2-phenylethyl)piperidine-1-carboxamide)

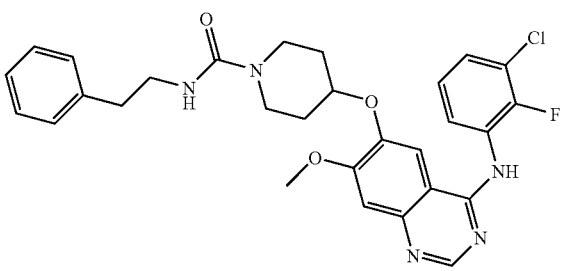

57 mg, 42%; starting isocyanate: phenethyl isocyanate.

NMR spectrum (DMSO-d6) 1.60 (m, 2H), 1.98 (m, 2H), 2.73 (t, 2H), 3.14 (m, 2H), 3.25 (m, 2H), 3.72 (m, 2H), 3.95 (s, 3H), 4.69 (m, 1H), 6.67 (m, 1H), 7.20 (m, 4H), 7.29 (m, 3H), 7.50 (m, 2H), 7.85 (s, 1H), 8.37 (m, 1H), 9.60 (s, 1H); Mass spectrum: MH+ 550.

Compound 94

(4-({4-[(3-Chloro-2-fluorophenyl)amino]-7-methoxyquinazolin-6-yl}oxy)-N-(3,4-dimethoxyphenyl)piperidine-1-carboxamide)

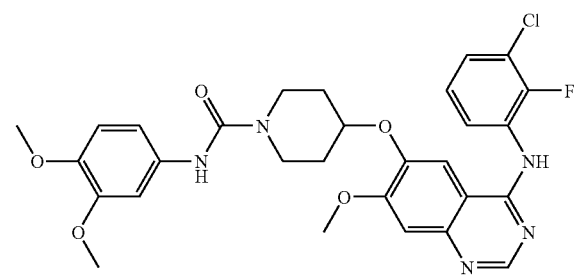

45 mg, 31%; starting isocyanate: 3,4-dimethoxyphenyl isocyanate.

NMR spectrum (DMSO-d6) 1.70 (m, 2H), 2.05 (m, 2H), 3.35 (m, 2H), 3.70 (s, 3H), 3.71 (s, 3H), 3.85 (m, 2H), 3.95 (s, 3H), 4.75 (m, 1H), 6.83 (d, 1H), 6.98 (d, 1H), 7.17 (s, 1H), 7.24 (s, 1H), 7.30 (m, 1H), 7.51 (m, 2H), 7.89 (s, 1H), 8.38 (s, 1H), 8.41 (s, 1H), 9.60 (m, 1H); Mass spectrum: MH+ 582

Compound 95

(4-({4-[(3-Chloro-2-fluorophenyl)amino]-7-methoxyquinazolin-6-yl}oxy)-N-(3-fluorophenyl)piperidine-1-carboxamide)

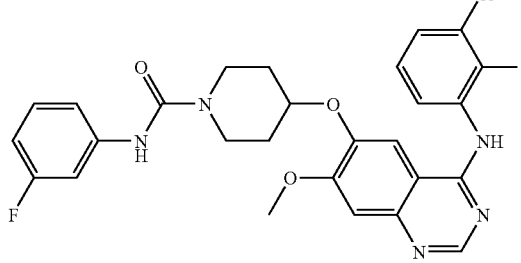

108 mg, 81%; starting isocyanate: 3-fluorophenyl isocyanate.

NMR spectrum (DMSO-d6) 1.72 (m, 2H), 2.07 (m, 2H), 3.35 (m, 2H), 3.85 (m, 2H), 3.95 (s, 3H), 4.77 (m, 1H), 6.74 (m, 1H), 7.31-7.24 (m, 4H), 7.55-7.44 (m, 3H), 7.90 (s, 1H), 8.38 (s, 1H), 8.79 (s, 1H), 9.60 (m, 1H); Mass spectrum: MH+ 540

Compound 96

(4-({4-[(3-Chloro-2-fluorophenyl)amino]-7-methoxyquinazolin-6-yl}oxy)-N-(3,5-dimethylisoxazol-4-yl)piperidine-1-carboxamide)

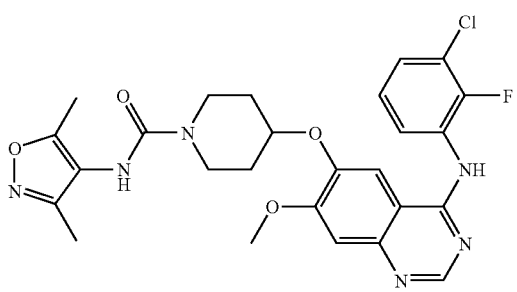

106 mg, 79%; starting isocyanate: 3,5-dimethylisoxazol-4-yl isocyanate.

NMR spectrum (DMSO-d6) 1.70 (m, 2H), 2.07 (s, 3H), 2.08 (m, 2H), 2.23 (s, 3H), 3.35 (m, 2H), 3.83 (m, 2H), 3.95 (s, 3H), 4.76 (m, 1H), 7.24 (s, 1H), 7.30 (m, 1H), 7.52 (m, 2H), 7.88 (s, 1H), 7.99 (s, 1H), 9.60 (m, 1H); Mass spectrum: MH+ 541

Compound 97

(4-({4-[(3-Chloro-2-fluorophenyl)amino]-7-methoxyquinazolin-6-yl}oxy)-N-2-thienylpiperidine-1-carboxamide)

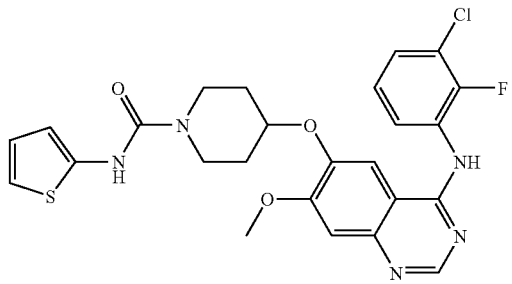

81 mg, 62%; starting isocyanate: 2-thienyl isocyanate.

NMR spectrum (DMSO-d6) 1.70 (m, 2H), 2.06 (m, 2H), 3.37 (m, 2H), 3.85 (m, 2H), 3.95 (s, 3H), 4.76 (m, 1H), 6.61 (m, 1H), 6.79 (m, 2H), 7.24 (s, 1H), 7.29 (m, 1H), 7.52 (m, 2H), 7.89 (s, 1H), 8.38 (s, 1H), 9.60 (m, 1H); 9.73 (m, 1H); Mass spectrum: MH+ 528

Compound 98

(4-({4-[(3-chloro-2-fluorophenyl)amino]-7-methoxyquinazolin-6-yl}oxy)-N-3-thienylpiperidine-1-carboxamide)

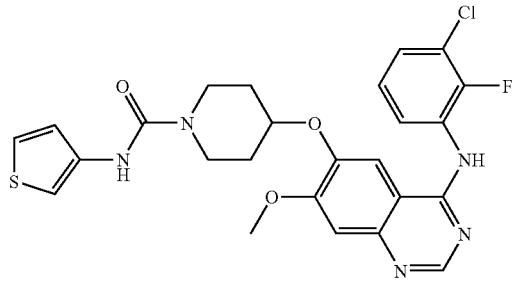

61 mg, 47%; starting isocyanate: 3-thienyl isocyanate.

NMR spectrum (DMSO-d6) 1.70 (m, 2H), 2.06 (m, 2H), 3.37 (m, 2H), 3.85 (m, 2H), 3.95 (s, 3H), 4.75 (m, 1H), 7.13 (m, 1H), 7.24 (s, 1H), 7.31-7.26 (m, 2H), 7.36 (m, 1H), 7.52 (m, 2H), 7.89 (s, 1H), 8.38 (s, 1H), 8.98 (s, 1H); Mass spectrum: MH+ 528

The invention claimed is:

1. A quinazoline derivative of the Formula I:

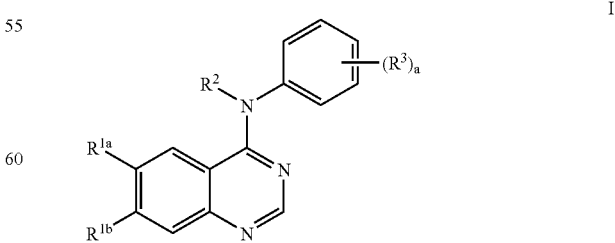

wherein:
one of $R^{1a}$ or $R^{1b}$ is a group of sub-formula (i)

$$Q^2-X^1-Z-Q^1-X^2-O-\qquad(i)$$

where $X^2$ and $X^1$ are independently selected from a direct bond or a group —$[CR^4R^5]_m$—, wherein m is an integer from 1 to 6, Z is C(O), SO$_2$, —C(O)NR$^{10}$—, —N(R$^{10}$)C(O)—, —C(O)O— or —OC(O)— where R$^{10}$ is hydrogen or (1-6C)alkyl, and each of R$^4$ and R$^5$ is independently selected from hydrogen, hydroxy, (1-4C)alkyl, halo(1-4C)alkyl, hydroxy(1-4C)alkyl, (1-4C)alkoxy(1-4C)alkyl, or R$^4$ and R$^5$ together with the carbon atom(s) to which they are attached form a (3-7)cycloalkyl ring, provided that when a group R$^4$ or R$^5$ is hydroxy, m is at least 2 and the carbon atom to which the hydroxy group is attached is not also attached to another oxygen or a nitrogen atom;

Q$^1$ is a piperidinyl ring, which is optionally substituted by one or two substituents selected from halogeno, trifluoromethyl, trifluoromethoxy, cyano, nitro, hydroxy, amino, carboxy, carbamoyl, acryloyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (2-6C)alkenylthio, (2-6C)alkynylthio, (1-6C)alkylsulfinyl, (2-6C)alkenylsulfinyl, (2-6C)alkynylsulfinyl, (1-6C)alkylsulfonyl, (2-6C)alkenylsulfonyl, (2-6C)alkynylsulfonyl, (1-6C)alkylamino, di-[(1-6C)alkyl]amino, (1-6C)alkoxycarbonyl, N,-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, sulfamoyl, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, carbamoyl(1-6C)alkyl, N-(1-6C)alkylcarbamoyl(1-6C)alkyl, N,N-di-[(1-6C)alkyl]carbamoyl(1-6C)alkyl, sulfamoyl(1-6C)alkyl, N-(1-6C)alkylsulfamoyl(1-6C)alkyl, N,N-di-[(1-6C)alkyl]sulfamoyl(1-6C)alkyl, (2-6C)alkanoyl(1-6C)alkyl, (2-6C)alkanoyloxy(1-6C)alkyl, (2-6C)alkanoylamino(1-6C)alkyl, N-(1-6C)alkyl-(2-6C)alkanoylamino(1-6C)alkyl and (1-6C)alkoxycarbonyl(1-6C)alkyl;

Q$^2$ is an isoxazolyl ring optionally substituted by one or two groups, which may be the same or different, selected from halogeno, hydroxy, nitro, amino, cyano, carbamoyl, (1-4C)alkyl, (1-4C)alkoxy, (2-4C)alkanoyl and (1-4C)alkylsulfonyl [1-4C)alkyl]amino, di[1-4C)alkyl]amino, N-[(1-4C)alkyl]carbamoyl, and N,N-di[1-4C)alkyl]carbamoyl;

and wherein any (2-4C)alkanoyl group in a substituent on Q$^2$ optionally bears one or two substituents, which may be the same or different, selected from hydroxy and (1-3C)alkyl, and wherein any (1-4C)alkyl group in a substituent on Q$^2$ optionally bears one or two substituents, which may be the same or different, selected from hydroxy, (1-4C)alkoxy and halogeno;

and the other of R$^{1a}$ or R$^{1b}$ is a group R$^1$ which is hydrogen, (1-6C)alkoxy and (1-4C)alkoxy(1-6C)alkyl, and wherein any (1-6C)alkoxy group within R$^1$ optionally bears 1, 2 or 3 substituents, which may be the same or different, selected from hydroxy, fluoro and chloro;

R$^2$ is selected from hydrogen and (1-6C)alkyl;

each R$^3$, which may be the same or different, is selected from halogeno, cyano, nitro, hydroxy, amino, carboxy, carbamoyl, sulfamoyl, trifluoromethyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, N-(1-6C)alkylsulfamoyl, and N,N-di-[(1-6C)alkyl]sulfamoyl a is 1, 2 or 3;

or a pharmaceutically acceptable salt thereof.

2. The quinazoline derivative according to claim 1 wherein X$^2$ is a direct bond.

3. The quinazoline derivative according to claim 1 wherein R$^1$ is selected from methoxy, ethoxy, isopropyloxy, cyclopropylmethoxy, 2-hydroxyethoxy, 2-fluoroethoxy, 2-methoxyethoxy, 2,2-difluoroethoxy, 2,2,2-trifluoroethoxy or 3-hydroxy-3-methylbutoxy.

4. The quinazoline derivative according to claim 3 wherein R$^1$ is methoxy.

5. The quinazoline derivative according to claim 1 wherein X$^1$ is suitably a direct bond or a (1-6C)alkylene group.

6. The quinazoline derivative according to claim 5 wherein X$^1$ is a direct bond or methylene or ethylene group.

7. The quinazoline derivative according to claim 1 wherein Z is selected from —C(O)—, —NR$^{10}$—C(O)— (wherein R$^{10}$ is H or (1-6C)alkyl), and —O—C(O)—.

8. The quinazoline derivative according to claim 7, wherein Z is —C(O)—.

9. The quinazoline derivative according to claim 7, wherein Z is selected from
—NH—C(O)— and —O—C(O)—.

10. The quinazoline derivative according to claim 1, wherein the group Q$^2$-X$^1$—Z— is linked to the piperidinyl nitrogen of Q$^1$.

11. The quinazoline derivative according to claim 1 wherein Q$^2$ is unsubstituted or substituted by a (1-4C)alkyl group, a (1-4C)alkoxy group, halogeno, amino, nitro, cyano, carbamoyl, di-[(1-4C)alkyl]amino, and N,N-di[(1-4C)alkyl]carbamoyl.

12. The quinazoline derivative according to claim 1 wherein R$^2$ is hydrogen.

13. The quinazoline derivative according to claim 1, wherein an R$^3$ is in the para position on the anilino ring, and this is selected from halogeno, cyano, nitro, hydroxy, amino, trifluoromethyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylamino and di-[(1-6C)alkyl]amino.

14. The quinazoline derivative according to claim 1 wherein the group of sub-formula (ii)

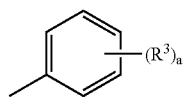

(ii)

in formula (I) is a group of sub-formula (iii)

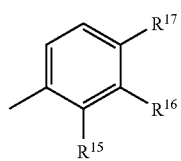

(iii)

where one of $R^{15}$ or $R^{17}$ is hydrogen and the other is halogeno, and $R^{16}$ is halogeno.

15. The quinazoline derivative according to claim 14 wherein the group of sub-formula (iii) is 3-chloro-2-fluorophenyl, or 3-chloro-4-fluorophenyl.

16. The compound according to claim 1 selected from one of the following:
   (1) N-(3-chloro-2-fluorophenyl)-6-{[1-(isoxazol-5-ylcarbonyl)piperidin-4-yl]oxy}-7-methoxyquinazolin-4-amine;
   (2) N-(3-chloro-2-fluorophenyl)-7-methoxy-6-({1-[(3-methylisoxazol-5-yl)acetyl]piperidin-4-yl}oxy)quinazolin-4-amine;
   (3) N-(3-chloro-2-fluorophenyl)-7-methoxy-6-({1-[(3-methylisoxazol-5-yl)carbonyl]piperidin-4-yl}oxy)quinazolin-4-amine;
   (4) N-(3-chloro-2-fluorophenyl)-7-methoxy-6-({1-[(5-methylisoxazol-3-yl)carbonyl]piperidin-4-yl}oxy)quinazolin-4-amine;
   (5) N-(3-chloro-2-fluorophenyl)-7-methoxy-6-({1-[(5-methylisoxazol-4-yl)carbonyl]piperidin-4-yl}oxy)quinazolin-4-amine;
   (6) N-(3-chloro-2-fluorophenyl)-7-methoxy-6-({1-[(3-methylisoxazol-4-yl)carbonyl]piperidin-4-yl}oxy)quinazolin-4-amine;
   (7) N-(3-chloro-2-fluorophenyl)-6-({1-[(3,5-dimethylisoxazol-4-yl)carbonyl]piperidin-4-yl}oxy)-7-methoxyquinazolin-4-amine;
   (8) N-(3-chloro-2-fluorophenyl)-7-{[1-(isoxazol-5-ylcarbonyl)piperidin-4-yl]oxy}-6-methoxyquinazolin-4-amine;
   (9) N-(3-chloro-2-fluorophenyl)-6-methoxy-7-({1-[(3-methylisoxazol-5-yl)acetyl]piperidin-4-yl}oxy)quinazolin-4-amine;
   (10) N-(3-chloro-2-fluorophenyl)-7-methoxy-6-({(3R)-1-[(3-methylisoxazol-5-yl)acetyl]piperidin-3-yl}oxy)quinazolin-4-amine; and
   (11) 4-({4-[(3-Chloro-2-fluorophenyl)amino]-7-methoxyquinazolin-6-yl}oxy)-N-(3,5-dimethylisoxazol-4-yl)piperidine-1-carboxamide.

17. A pharmaceutical composition which comprises a quinazoline derivative of the Formula I, or a pharmaceutically-acceptable salt thereof, as defined in claim 1 in association with a pharmaceutically-acceptable diluent or carrier.

* * * * *